US012251449B2

(12) United States Patent
Hartgerink et al.

(10) Patent No.: US 12,251,449 B2
(45) Date of Patent: Mar. 18, 2025

(54) SYNTHETIC MULTIDOMAIN PEPTIDE BIOMATERIALS THAT INHIBIT INDUCIBLE NITRIC OXIDE SYNTHASE

(71) Applicants: William Marsh Rice University, Houston, TX (US); Baylor College of Medicine, Houston, TX (US); The Board of Regents of the University of Texas System, Austin, TX (US)

(72) Inventors: Jeffrey Hartgerink, Pearland, TX (US); Andrew G. Sikora, Houston, TX (US); David Leach, Houston, TX (US); Jared M. Newton, Houston, TX (US); Simon Young, Houston, TX (US)

(73) Assignees: William Marsh Rice University, Houston, TX (US); Baylor College of Medicine, Houston, TX (US); The Board of Regents of The University of Texas System, Austin, TX (US)

( * ) Notice: Subject to any disclaimer, the term of this patent is extended or adjusted under 35 U.S.C. 154(b) by 727 days.

(21) Appl. No.: 17/127,512

(22) Filed: Dec. 18, 2020

(65) Prior Publication Data

US 2021/0205468 A1 Jul. 8, 2021

Related U.S. Application Data

(60) Provisional application No. 62/950,718, filed on Dec. 19, 2019.

(51) Int. Cl.
*A61K 47/69* (2017.01)
*A61K 31/7052* (2006.01)
*A61P 35/00* (2006.01)
*C07K 16/28* (2006.01)

(52) U.S. Cl.
CPC ...... *A61K 47/6903* (2017.08); *A61K 31/7052* (2013.01); *A61P 35/00* (2018.01); *C07K 16/2818* (2013.01); *C07K 16/2827* (2013.01)

(58) Field of Classification Search
CPC . A61K 47/6903; A61K 31/7052; A61P 35/00; C07K 16/2818; C07K 16/2827
See application file for complete search history.

(56) References Cited

U.S. PATENT DOCUMENTS

| | | | |
|---|---|---|---|
| 7,569,555 B2 | 8/2009 | Karaolis | |
| 7,592,326 B2 | 9/2009 | Karaolis | |
| 7,709,458 B2 | 5/2010 | Karaolis et al. | |
| 9,226,959 B2 | 1/2016 | Kramps et al. | |
| 9,526,762 B1 | 12/2016 | Hartgerink et al. | |
| 2005/0272662 A1 | 12/2005 | Stupp et al. | |
| 2008/0286296 A1 | 11/2008 | Ebensen et al. | |
| 2014/0135472 A1 | 5/2014 | King et al. | |
| 2014/0205653 A1 | 7/2014 | Dubensky et al. | |
| 2016/0287623 A1 | 10/2016 | Gajewski et al. | |
| 2017/0044206 A1 | 2/2017 | Altman et al. | |
| 2017/0172953 A1 | 6/2017 | Hartgerink et al. | |
| 2018/0015174 A1 | 1/2018 | Irvine et al. | |
| 2018/0354991 A1* | 12/2018 | Wilson | A61P 25/28 |
| 2020/0146975 A1 | 5/2020 | Young et al. | |
| 2021/0386907 A1 | 12/2021 | Hartgerink et al. | |
| 2023/0143731 A1* | 5/2023 | Kibbe | A61K 38/00 514/1.1 |

FOREIGN PATENT DOCUMENTS

| | | |
|---|---|---|
| WO | WO 2013/185052 | 12/2013 |
| WO | WO 2014/093936 | 6/2014 |
| WO | WO 2014/104981 | 7/2014 |
| WO | WO 2015/016718 | 2/2015 |
| WO | WO 2015/185565 | 12/2015 |
| WO | WO 2016/096577 | 6/2016 |
| WO | WO 2018/045058 | 3/2018 |
| WO | WO 2019/018572 | 1/2019 |
| WO | WO 2020/081717 | 4/2020 |

OTHER PUBLICATIONS

Leach et al."Drug-Mimicking Nanofibrous Peptide Hydrogel for Inhibition of Inducible Nitric Oxide Synthase" (ACT Biomater Sci Eng 2019 vol. 5, pp. 6755-6765; published Nov. 13, 2019). (Year: 2019).*
The Leach Dissertation, Rice University, Houston, Texas, May 2020. (Year: 2020).*
The Lopez-Silva Dissertation, Rice University, Houston, Texas, May 2020. (Year: 2020).*
Leach et al."Biomaterial-Facilitated Immunotherapy for Established Oral Cancers" (ACT Biomater Sci Eng 2021 vol. 7, pp. 415-421; published Jan. 20, 2021). (Year: 2021).*
Ablasser et al., "cGAS produces a 2′-5′-linked cyclic dinucleotide second messenger that activates STING," Nature, 498(7454):380-384, 2013.
Aduro Biotech, NCT02675439: Feb. 5, 2016 ed.; National Institutes of Health: ClinicalTrails.gov, 2017.
Ahsan, "3-Nitrotyrosine: A biomarker of nitrogen free radical species modified proteins in systemic autoimmunogenic conditions," Human Immunology, 74:1392-1399, 2013.
Aldridge et al., "Lipopolysaccharide-stimulated RAW 264.7 macrophage inducible nitric oxide synthase and nitric oxide production is decreased by an omega-3 fatty acid lipid emulsion," J. Surg. Res., 149:296-302, 2008.
Ambs et al., "p53 and vascular endothelial growth factor regulate tumor growth of NOS2-expressing human carcinoma cells," Nature Medicine, 4:1371, 1998.
Aulisa et al., "Self-assembly of multidomain peptides: sequence variation allows control over cross-linking and viscoelasticity," Biomacromolecules, 10:2694-2698, 2009.

(Continued)

*Primary Examiner* — Catherine S Hibbert
(74) *Attorney, Agent, or Firm* — Parker Highlander PLLC

(57) ABSTRACT

Provided herein are compositions comprising multi domain peptide (MDP) hydrogels where the peptides that constitute the hydrogel have at least one N6-(1-iminoethyl)-lysine side chain. Also provided are hydrogels that further comprise a STING agonist, an immune checkpoint inhibitor, and/or an anti-cancer therapy. Also provided are methods of using such compositions in the treatment of cancer.

10 Claims, 19 Drawing Sheets
(18 of 19 Drawing Sheet(s) Filed in Color)
Specification includes a Sequence Listing.

(56) References Cited

OTHER PUBLICATIONS

Bakota et al., "Injectable multidomain peptide nanofiber hydrogel as a delivery agent for stem cell secretome," Biomacromolecules. American Chemical Society, 12(5):1651-1657, 2011.

Barber, "STING: infection, inflammation and cancer," Nat Rev Immunol, 15 (12):760-770, 2015.

Berzofsky et al., "Progress on new vaccine strategies for the immunotherapy and prevention of cancer," The Journal of Clinical Investigation, 113:1515-1525, 2004.

Bonomi et al., "The Role of Inflammation in Head and Neck Cancer." In Inflammation and Cancer, Aggarwal, B. B.; Sung, B.; Gupta, S. C., Eds. Springer Basel: Basel, 2014; pp. 107-127.

Bookstaver et al., "Improving Vaccine and Immunotherapy Design Using Biomaterials," Trends in Immunology, 39:135-150, 2018.

Brudno et al., "Replenishable drug depot to combat post-resection cancer recurrence," Biomaterials, 178:373-382, 2018.

Bryan & Grisham, "Methods to detect nitric oxide and its metabolites in biological samples," Free Radical Biology and Medicine, 43:645-657, 2007.

Carrejo et al., "Multidomain peptide hydrogel accelerates healing of full-thickness wounds in diabetic mice," ACS Biomater. Sci. Eng., 4:1387-1396, 2018.

Chen & Mellman, "Oncology Meets Immunology: The Cancer-Immunity Cycle," Immunity, 39:1-10, 2013.

Collier & Segura, "Evolving the use of peptides as components of biomaterials," Biomaterials, 32:4198-4204, 2011.

Corrales et al., "Direct Activation of STING in the Tumor Microenvironment Leads to Potent and Systemic Tumor Regression and Immunity," Cell Rep., 11(7):1018-1030, 2015.

Cui et al., "Self-assembly of peptide amphiphiles: From molecules to nanostructures to biomaterials," Peptide Science, 94:1-18, 2010.

Dellacherie et al., "Macroscale biomaterials strategies for local immunomodulation," Nature Reviews Materials, 4:379-397, 2019.

Deshpande et al., "Nitric oxide modulators: An emerging class of medicinal agents," Indian J. Pharm. Sci., 74:487-497, 2012.

Dong et al., "Self-Assembly of Multidomain Peptides: Balancing Molecular Frustration Controls Conformation and Nanostructure," Journal of the American Chemical Society, 129:12468-12472, 2007.

Downey et al., "DMXAA Causes Tumor Site-Specific Vascular Disruption in Murine Non-Small Cell Lung Cancer, and like the Endogenous Non-Canonical Cyclic Dinucleotide STING Agonist, 2'3'-cGAMP, Induces M2 Macrophage Repolarization," PLOS ONE, 9(6):e99988, 2014.

Fukumura et al., "Predominant role of endothelial nitric oxide synthase in vascular endothelial growth factor-induced angiogenesis and vascular permeability," Proceedings of the National Academy of Sciences, 98:2604-2609, 2001.

Fukumura et al., "The role of nitric oxide in tumour progression," Nature Reviews Cancer, 6:521, 2006.

Gadkaree et al., "Induction of tumor regression by intratumoral STING agonists combined with anti-programmed death-L1 blocking antibody in a preclinical squamous cell carcinoma model," Head and Neck, 39(6):1086-1094, 2017.

Galler et al., "A customized self-assembling peptide hydrogel for dental pulp tissue engineering," Tissue engineering Part A, 18(1-2):176-184, 2012.

Galler et al., "Self-assembling multidomain peptide hydrogels: designed susceptibility to enzymatic cleavage allows enhanced cell migration and spreading," J Am Chem Soc., 132(9):3217-3223, 2010.

Galler, "Self-Assembling Peptide Hydrogels Targeted for Dental Tissue Regeneration," PhD Dissertation, Rice University, UMI No. 342141, 2010.

Grimm et al., "Molecular Pathways: Inflammation-Associated Nitric-Oxide Production as a Cancer-Supporting Redox Mechanism and a Potential Therapeutic Target," Clin. Cancer Res., 19:5557, 2013.

Gu & Mooney, "Biomaterials and emerging anticancer therapeutics: engineering the microenvironment," Nat. Rev. Cancer, 16:56-66, 2016.

Hanahan & Weinberg, "Hallmarks of Cancer: The Next Generation," Cell, 144:646-674, 2011.

Hanoteau et al., "Tumor microenvironment modulation enhances immunologic benefit of chemoradiotherapy," Journal for ImmunoTherapy of Cancer, 7:10, 2019.

Hanson et al., "Nanoparticle STING agonists are potent lymph node-targeted vaccine adjuvants," Clin Invest., 125(6):2532-2546, 2015.

Housman et al., "Drug resistance in cancer: an overview," Cancers, 6:1769-1792, 2014.

Ischiropoulos, "Biological selectivity and functional aspects of protein tyrosine nitration," Biochemical and Biophysical Research Communications, 305:776-783, 2003.

Ishikawa et al., "STING regulates intracellular DNA-mediated, type I interferon-dependent innate immunity," Nature, 461:788-792, 2009.

Jayaraman et al., "iNOS Expression in CD4+ T Cells Limits Treg Induction by Repressing TGFβ1: Combined iNOS Inhibition and Treg Depletion Unmask Endogenous Antitumor Immunity," Clinical Cancer Research, 20:6439-6451, 2014.

Jayaraman et al., "Tumor-Expressed Inducible Nitric Oxide Synthase Controls Induction of Functional Myeloid-Derived Suppressor Cells through Modulation of Vascular Endothelial Growth Factor Release," The Journal of Immunology, 188(11):5365, 2012.

Jenkins et al., "Roles of nitric oxide in tumor growth," Proceedings of the National Academy of Sciences, 92:4392-4396, 1995.

Judd et al., "Comparative Analysis of Tumor-Infiltrating Lymphocytes in a Syngeneic Mouse Model of Oral Cancer," Otolaryng. Head Neck, 147:493-500, 2012.

Karaolis et al., "3',5'-Cyclic diguanylic acid (c-di-GMP) inhibits basal and growth factor-stimulated human colon cancer cell proliferation," Biochem Biophys Res Commun., 329(1):40-45, 2005.

Kearney & Mooney, "Macroscale delivery systems for molecular and cellular payloads," Nat. Mater., 12:1004, 2013.

Kim et al., "Enhancement of neuronal cell adhesion by covalent binding of poly-d-lysine," Journal of Neuroscience Methods, 202:38-44, 2011.

Koshy et al., "Biomaterials for Enhancing Anti-Cancer Immunity," Current Opinions Biotechnology, 40:1-8, 2016.

Kumar et al., "Drug-triggered and cross-linked self-assembling nanofibrous hydrogels," Journal of the American Chemical Society, 137:4823-4830, 2015.

Kumar et al., "Highly angiogenic peptide nanofibers," ACS Nano, 9(1):860-868, 2015.

Kumar et al., "Treatment of hind limb ischemia using angiogenic peptide nanofibers," Biomaterials, 98:113-119, 2016.

Lam et al., "Cationic surface charge combined with either vitronectin or laminin dictates the evolution of human embryonic stem cells/microcarrier aggregates and cell growth in agitated cultures," Stem Cells Dev, 23:1688-1703, 2014.

Leach et al., "STINGel: Controlled release of a cyclic dinucleotide for enhanced cancer immunotherapy," Biomaterials, 163:67-75, 2018.

Leach et al., "Advances in immunotherapy delivery from implantable and injectable biomaterials," Acta Biomaterialia, 88:15-31, 2019.

Leach et al., "Drug-Mimicking Nanofibrous Peptide Hydrogel for Inhibition of Inducible Nitric Oxide Synthase," ACS Biomater. Sci. Eng., 5:6755-6765, 2019.

Leach et al., "Biomaterial-facilitated Immunotherapy for Established Oral Cancers," ACS Biomateri. Sci. Eng., 7:415-421, 2021.

Lei et al., "MAVS-mediated apoptosis and its inhibition by viral proteins," PLoS One, 4(5):e5466, 2009.

Li et al., "'Missing Tooth' Multidomain Peptide Nanofibers for Delivery of Small Molecule Drugs," Biomacromolecules, 17:2087-2095, 2016.

Li & Hartgerink, "Covalent Capture of Aligned Self-Assembling Nanofibers," Journal of the American Chemical Society, 139:8044-8050, 2017.

Lopez-Silva et al., "Self-Assembling Multidomain Peptides: Design and Characterization of Neutral Peptide-Based Materials with pH and Ionic Strength Independent Self-Assembly," ACS Biomater. Sci. Eng., 5:977-985, 2019.

(56) References Cited

OTHER PUBLICATIONS

Lopez-Silva et al., "Chemical functionality of multidomain peptide hydrogels governs early host immune response," Biomaterials, 231:119667, 2020.
Lu et al., "Myeloid cell-derived inducible nitric oxide synthase suppresses M1 macrophage polarization," Nat. Commun., 6:6676, 2015.
MacMicking et al., "Nitric Oxide and Macrophage Function," Annual Review of Immunology, 15:323-350, 1997.
Mannick et al., "S-Nitrosylation of mitochondrial caspases," The Journal of Cell Biology, 154:1111-1116, 2001.
Miyabe et al., "A new adjuvant delivery system 'cyclic di-GMP/ YSK05 liposome' for cancer immunotherapy," Journal of Controlled Release, 184:20-27, 2014.
Moore et al., "Enhanced Tumor Control with Combination mTOR and PD-L1 Inhibition in Syngeneic Oral Cavity Cancers," Cancer Immunol Res., 4(7):611-620, 2016.
Moore et al., "L-N6-(1-Iminoethyl)lysine: A Selective Inhibitor of Inducible Nitric Oxide Synthase," J. Med. Chem., 37:3886-8, 1994.
Moore et al., "Established T Cell-Inflamed Tumors Rejected after Adaptive Resistance Was Reversed by Combination STING Activation and PD-1 Pathway Blockade," Cancer Immunol Res, 4:1061-1071, 2016.
Moore et al., "Nanofibrous peptide hydrogel elicits angiogenesis and neurogenesis without drugs, proteins, or cells," Biomaterials, 161:154-163, 2018.
Moore & Hartgerink, "Self-Assembling Multidomain Peptide Nanofibers for Delivery of Bioactive Molecules and Tissue Regeneration," Accounts of Chemical Research, 50:714-722, 2017.
Moy et al., "Biological mechanisms of immune escape and implications for immunotherapy in head and neck squamous cell carcinoma," Eur. J. Cancer, 76:152-166, 2017.
Nathan & Hibbs, "Role of nitric oxide synthesis in macrophage antimicrobial activity," Current Opinion in Immunology, 3:65-70, 1991.
Newton et al., "Immune microenvironment modulation unmasks therapeutic benefit of radiotherapy and checkpoint inhibition," J. Immunother. Cancer, 7:216, 2019.
Pardoll, "The blockade of immune checkpoints in cancer immunotherapy," Nat Rev Cancer, 12(4):252-264, 2012.
Park et al., "Extended Release of Perioperative Immunotherapy Prevents Tumor Recurrence and Eliminates Metastases," Sci Transl Med., 10(433), 2018.
Romling et al., "Cyclic di-GMP as a second messenger," Curr Opin Microbiol., 9(2):218-228, 2006.
Samadi et al., "A multi-targeted approach to suppress tumor-promoting inflammation," Seminars in Cancer Biology, 35:S151-S184, 2015.
Schneider et al., "The effect of hydrogel charge density on cell attachment," Biomaterials, 25:3023-3028, 2004.
Sikora et al., "Targeted inhibition of inducible nitric oxide synthase inhibits growth of human melanoma in vivo and synergizes with chemotherapy," Clinical Cancer Research, 16:1834, 2010.
Sun et al., "Inhibiting myeloid-derived suppressor cell trafficking enhances T cell immunotherapy," JCI Insight, 4:e126853, 2019.
Tamura et al., "The IRF Family Transcription Factors in Immunity and Oncogenesis," Annu Rev Immunol, 26 (1):535-584, 2008.
Tang et al., "Mechanistic studies of inactivation of inducible nitric oxide synthase by amidines," Biochemistry, 54:2530-2538, 2015.
Wang & Mooney, "Biomaterial-assisted targeted modulation of immune cells in cancer treatment," Nature Materials, 17:761-772, 2018.
Wang et al., "Immune Checkpoint Inhibitor Toxicity in Head and Neck Cancer: From Identification to Management," Frontiers in Pharmacology, 10:1254, 2019.
Wickremasinghe et al., "Two-Step Self-Assembly of Liposome-Multidomain Peptide Nanofiber Hydrogel for Time-Controlled Release," Biomacromolecules, 15:3587-3595, 2014.
Wickremasinghe et al., "Controlled Angiogenesis in Peptide Nanofiber Composite Hydrogels," ACS Biomater. Sci. Eng. American Chemical Society, 1(9):845-854, 2015.
Xing et al., "Incidence rates of immune-related adverse events and their correlation with response in advanced solid tumours treated with NIVO or NIVO+IPI: a systematic review and meta-analysis," J. Immunother. Cancer, 7:341, 2019.
Yamaguchi et al., "Glioma tumourgenicity is decreased by iNOS knockout: experimental studies using the C6 striatal implantation glioma model," British Journal of Neurosurgery, 16:567-572, 2002.
Yildiz et al., "Enhanced immunostimulatory activity of cyclic dinucleotides on mouse cells when complexed with a cell-penetrating peptide or combined with CpG," Eur J Immunol., 45(4):1170-1179, 2015.
Zhang & Xu, "Metastatic melanoma cells escape from immunosurveillance through the novel mechanism of releasing nitric oxide to induce dysfunction of immunocytes," Melanoma Research, 11:559-567, 2001.

\* cited by examiner

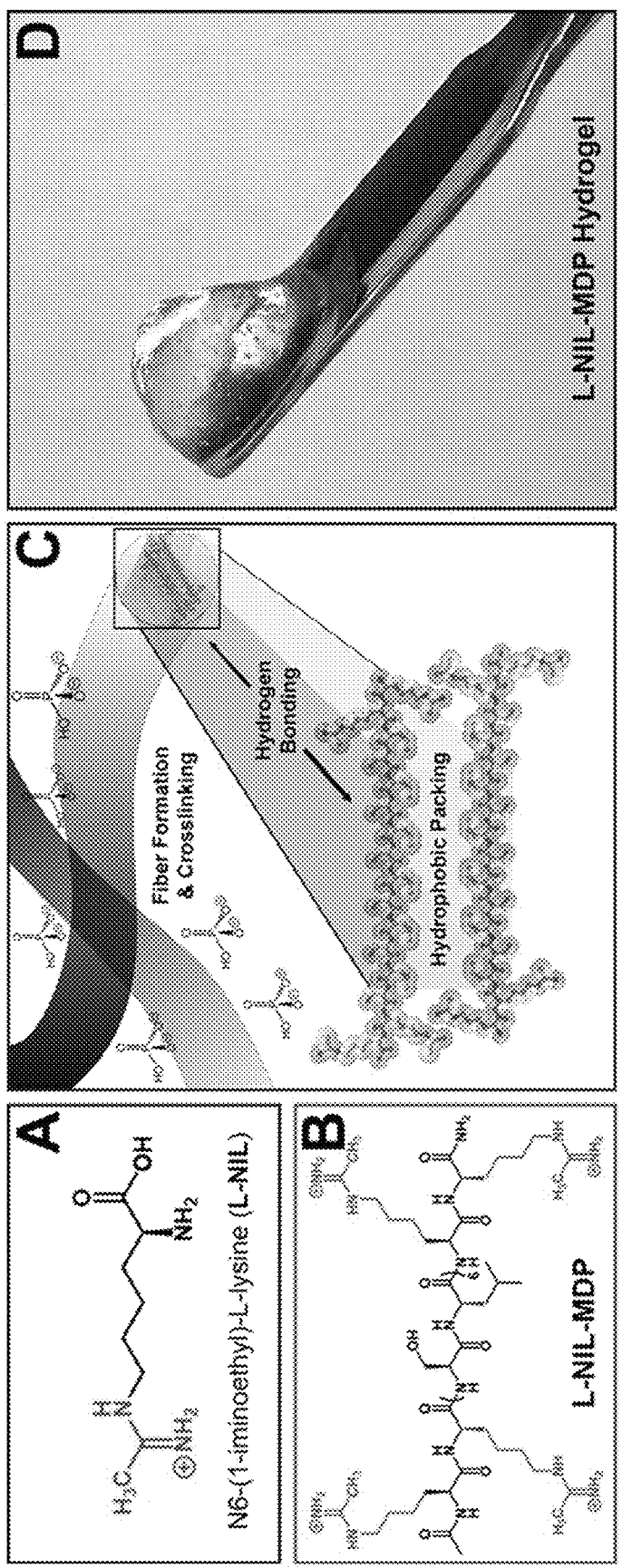
FIGS. 1A-D

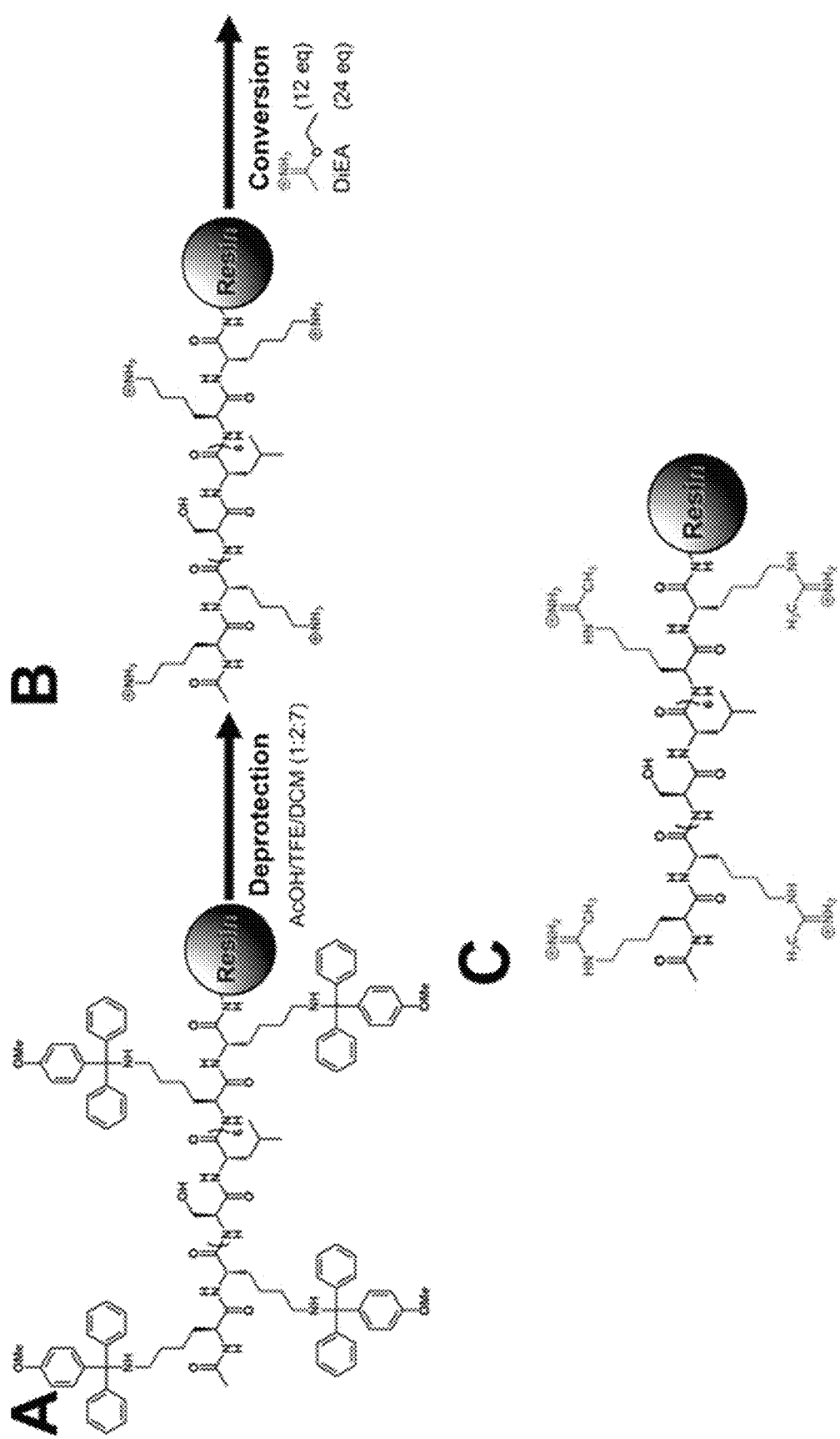
FIGS. 2A-C

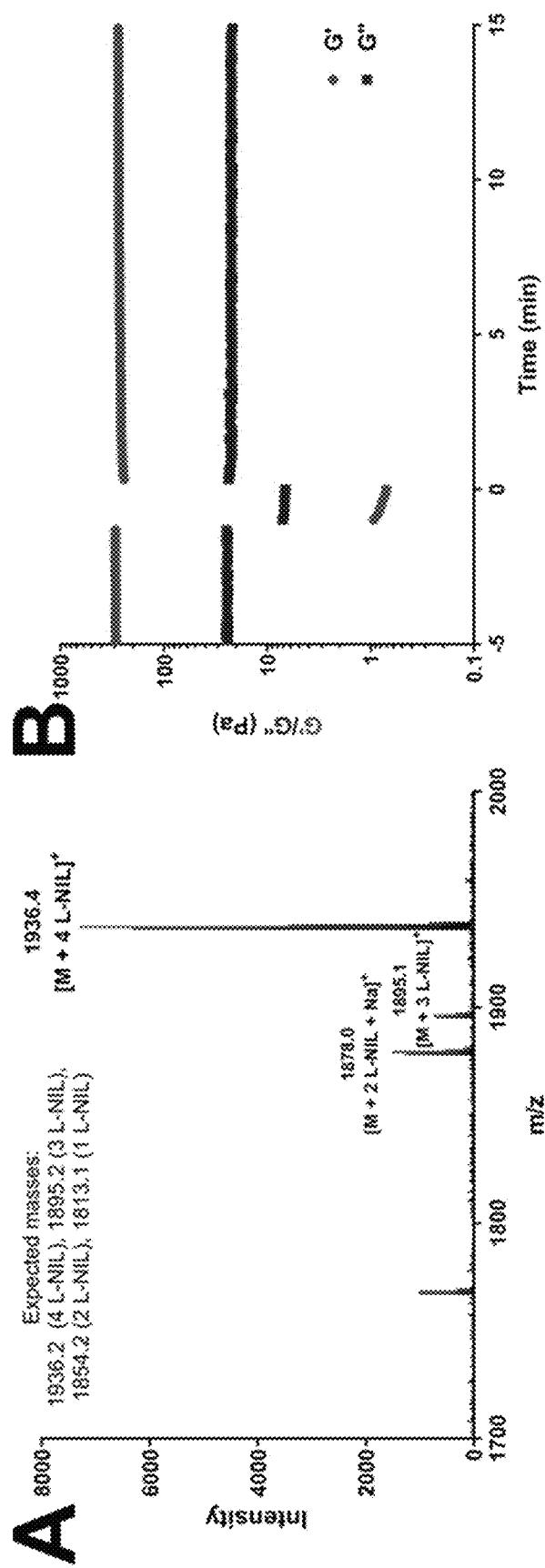
FIGS. 3A-B

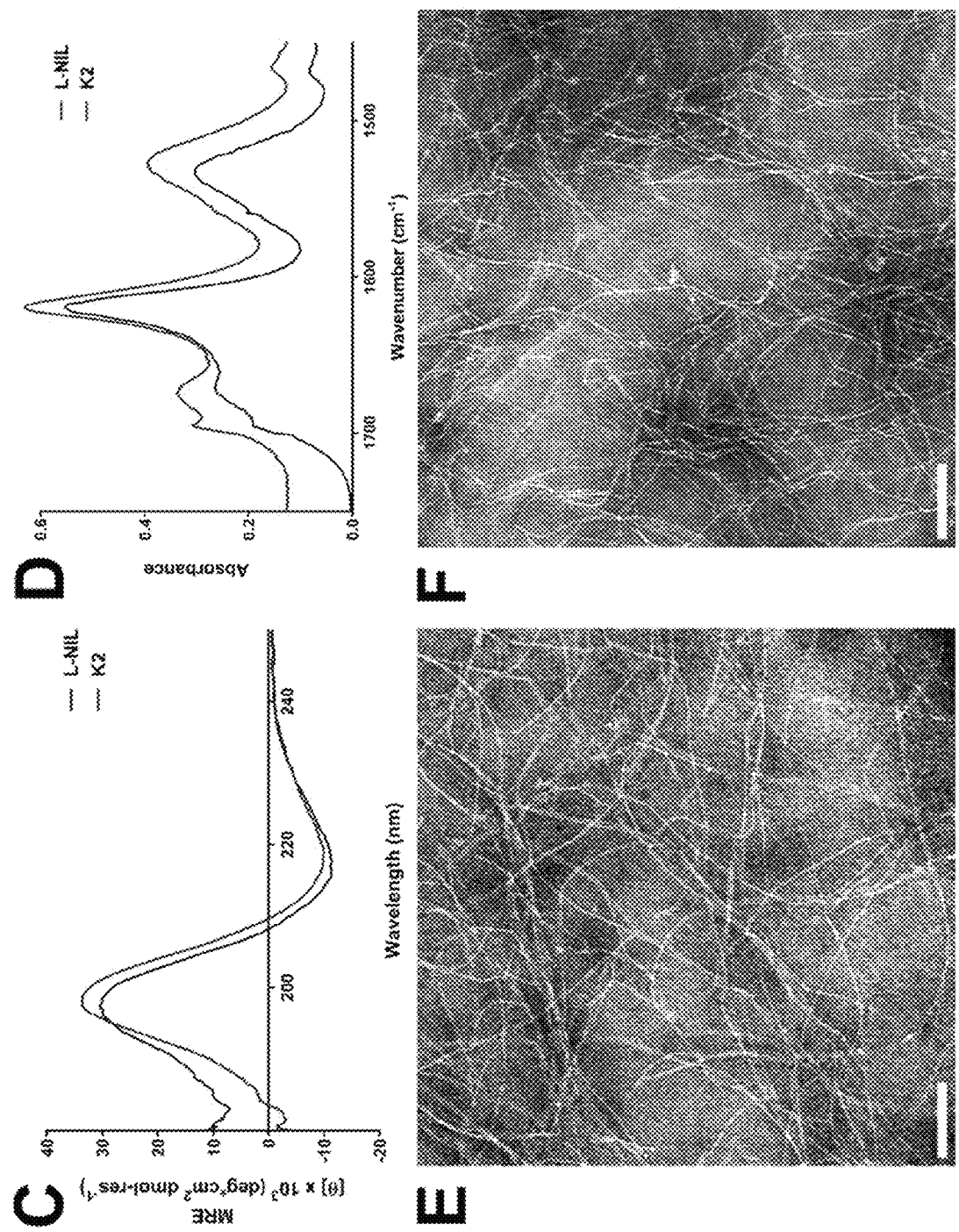
FIGS. 3C-F

SEQUENCE LISTING

```
<160> NUMBER OF SEQ ID NOS: 6

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1

Ser Leu Ser Leu Ser Leu
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic peptide

<400> SEQUENCE: 2

Lys Lys Ser Leu Ser Leu Ser Leu Lys Lys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: X is monomethoxytrityl BLOCKED lysine
<220> FEATURE:
<221> NAME/KEY: MOD_RES
<222> LOCATION: (9)..(10)
<223> OTHER INFORMATION: X is monomethoxytrityl BLOCKED lysine

<400> SEQUENCE: 3

Xaa Xaa Ser Leu Ser Leu Ser Leu Xaa Xaa
1               5                   10
```

```
<210> SEQ ID NO 4
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: X is hydroxyproline
<220> FEATURE:
<221> NAME/KEY: MOD_RES
<222> LOCATION: (9)..(10)
<223> OTHER INFORMATION: X is hydroxyproline

<400> SEQUENCE: 4

Xaa Xaa Ser Leu Ser Leu Ser Leu Xaa Xaa
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide

<400> SEQUENCE: 5

Glu Glu Ser Leu Ser Leu Ser Leu Glu Glu
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide

<400> SEQUENCE: 6

Arg Arg Ser Leu Ser Leu Ser Leu Arg Arg
1               5                   10
```

SYNTHETIC MULTIDOMAIN PEPTIDE BIOMATERIALS THAT INHIBIT INDUCIBLE NITRIC OXIDE SYNTHASE

REFERENCE TO RELATED APPLICATIONS

The present application claims the priority benefit of U.S. provisional application No. 62/950,718, filed Dec. 19, 2019, the entire contents of which is incorporated herein by reference.

STATEMENT REGARDING FEDERALLY SPONSORED RESEARCH

This invention was made with government support under Grant Nos. DE021798, DE023577, DE024173, and DE027794 awarded by the National Institutes of Health and Grant No. 1450681 awarded by the National Science Foundation. The government has certain rights in the invention.

REFERENCE TO A SEQUENCE LISTING

The instant application contains a Sequence Listing, which has been submitted in ASCII format via EFS-Web and is hereby incorporated by reference in its entirety. Said ASCII copy, created on May 8, 2024, is named RICEP0070US_ST25.txt and is 1,827 bytes in size.

BACKGROUND

The development of this disclosure was funded in part by the Welch Foundation under Grant No. C-1557.

1. FIELD

The present invention relates generally to the fields of chemistry, cell biology, and medicine. More particularly, it concerns compositions of multidomain peptide hydrogels that have iNOS inhibitory activity as well as methods of treating cancer therewith.

2. DESCRIPTION OF RELATED ART

N6-(1-iminoethyl)-L-lysine (L-NIL) and its derivatives are potent immunoregulatory drugs that selectively inhibit inducible nitric oxide synthase (iNOS), which has been shown to delay cancer tumor growth and extend subject survival in various models (Moore et al., 1994; Sikora et al., 2010). iNOS is one of the primary enzymes responsible for the in vivo synthesis of nitric oxide (NO) from L-arginine, with NO being a pervasive and multifunctional cell-signaling molecule that has many broad-ranging effects (Tang et al., 2015; Fukumura et al., 2006). The expression and activity of the enzyme iNOS is highly upregulated in many types of cancers, leading to increased synthesis of NO and promoting various conditions conducive to tumor growth, such as increased angiogenesis (Jayaraman et al., 2012; Jenkins et al., 1995), avoidance of apoptosis (Mannick et al., 2001), and immunosuppression (Fukumura et al., 2006; Zhang & Xu, 2001; Fukumura et al., 2001). The small-molecule drug L-NIL can be used to selectively inhibit iNOS and curtail aberrant NO production, thereby reducing various downstream effects such as immunosuppression of T cells, secretion of vascular endothelial growth factor (VEGF), and ultimately tumor growth.

However, the use of L-NIL or other small-molecule iNOS inhibitors in preclinical research has been hindered by the need to repeatedly deliver large drug quantities to subjects over a long period of time to achieve treatment efficacy. This is usually achieved by the addition of L-NIL to the drinking water in murine models (Sikora et al., 2010). While technically simple, this administration procedure results not only in excessive waste of valuable material (as drug-doped water must be exchanged daily), but also results in inconsistent treatment results when administered "ad libitum," or "as much as desired." Some mice will drink more or less of the doped water, thus receiving larger or smaller drug doses based on individual drinking habits. Furthermore, reliance on the oral administration route must combat issues of absorption, bioavailability, and incomplete drug distribution (Sikora et al., 2010). The development of an injectable, controlled and extended dose delivery system for L-NIL that could reduce material waste, standardize drug intake, and increase maximum dosage by bypassing the oral delivery route would therefore be highly advantageous, both financially and for clinical translation. As such, compositions and methods for the direct intratumoral delivery of iNOS inhibitors are needed in order to increase localized dosage to tumor and tumor-infiltrating immune cells while minimizing systemic side-effects.

SUMMARY

In one embodiment, provided herein are peptides comprising a first domain, a second domain, and a third domain; wherein the first and third domain are each $X_m$ and m is 1-6; wherein the first domain is positioned at the N-terminal end of the second domain; wherein the third domain is positioned at the C-terminal end of the second domain; and wherein the second domain comprises alternating hydrophobic (H) and hydrophilic (p) amino acids, wherein X is an amino acid having a side chain with nitric oxide synthase (NOS) inhibitory activity. In some aspects, X is an amino acid having a side chain selected from the group consisting of: N6-(1-iminoethyl)-lysine (L-NIL), 7-Nitroindazole (7-NI), $N^G$-monomethyl-L-arginine (L-NMMA), $N^G$-nitro-L-arginine methyl ester (L-NAME), $N^5$-(1-iminoethyl)-L-ornithine (L-NIO), N-(3-(Aminomethyl)benzyl)acetamidine (1400W), 3-[[2-[(1-iminoethyl)amino]ethyl]sulphonyl]-L-alanine (GW273629), [2-[(1-iminoethyl) amino]ethyl]-L-homocysteine (GW274150), and N-[4-[2-[[(3-Chlorophenyl)methyl]amino]ethyl]phenyl]-2-thiophenecarboxamide (ARL17477). In some aspects, X is an amino acid having an N6-(1-iminoethyl)-lysine side chain.

In some aspects, the hydrophilic (p) amino acids are polar amino acids. In certain aspects, the hydrophilic (p) amino acids are selected from the group consisting of S, T, N, and Q. In some aspects, the hydrophobic (H) amino acids are selected from the group consisting of L, I, V, A, F, Y, W, and M. In some aspects, the second domain comprises $(Hp)_n$. In some aspects, the second domain comprises $(pH)^n$. In certain aspects, n is 4-6. In certain aspects, the second domain comprises (SerLeu)$_6$ (SEQ ID NO: 1).

In some aspects, the peptides are N-terminally acetylated. In some aspects, the peptides are C-terminally amidated. In some aspects, the peptides are produced using solid-phase synthesis.

In one embodiment, provided herein are systems comprising a plurality of peptides according to any one of the present embodiments. In some aspects, the peptides are capable of self-assembling into a nanofiber. In some aspects, the system is lyophilized.

In one embodiment, provided herein are nanofibers comprising a plurality of peptides according to any one of the present embodiments.

In one embodiment, provided herein are hydrogels comprising a plurality of peptides according to any one of the present embodiments. In some aspects, the hydrogel is biocompatible. In some aspects, the hydrogel remains intact at pH 3-11. In some aspects, the hydrogel remains intact at physiological pH. In some aspects, the hydrogels further comprise a STING agonist (e.g., a cyclic dinucleotide (CDN)), an immune checkpoint inhibitor, and/or an anti-cancer drug. In some aspects, the hydrogels further comprise a cyclic dinucleotide (CDN) and an immune checkpoint inhibitor. In certain aspects, the CDN is a natural endogenous CDN, such as produced by cGAS. In certain aspects, the CDN is a synthetic CDN, such as CDN analog. In certain aspects, the CDN analog comprises a modified base or non-natural internucleoside linkage. In some aspects, the CDN is dithio-$(R_P,R_P)$-[cyclic[A(2',5')pA(3',5')p]], 2'2'-cGAMP, 2'3'-cGAMP, 3'3'-cGAMP, c-di-AMP, 2'3'-c-di-AMP, 2'3'-c-di-AM(PS)2, c-di-GMP, c-di-UMP, c-di-IMP. In some aspects, the immune checkpoint inhibitor is a PD-L1 antibody, a PD-1 antibody, or a CTLA4 antibody.

In one embodiment, provided herein are methods of treating a cancer in a patient, the method comprising administering to the patient a therapeutically effective amount of a composition according to any one of the present embodiments. In some aspects, the methods comprise administering the composition once. In some aspects, the methods comprise administering the composition two or more times. In some aspects, administering comprises intratumoral administration, administration to the tumor bed, or administration regional to the tumor. In some aspects, the methods further comprise administering a second cancer therapy. In certain aspects, the second cancer therapy is a chemotherapeutic agent, gene therapy, surgery, a radiotherapy, or an immunotherapy. In certain aspects, the second cancer therapy is surgery, and administering comprises treating a resected tumor bed with said composition. In some aspects, the cancer is a colorectal cancer, a neuroblastoma, a breast cancer, a pancreatic cancer, a brain cancer, a lung cancer, a stomach cancer, a skin cancer, a testicular cancer, a prostate cancer, an ovarian cancer, a liver cancer, an esophageal cancer, a cervical cancer, a head and neck cancer, a melanoma, or a glioblastoma. In some aspects, the cancer is a head and neck squamous cell carcinoma. In some aspects, the patient is a mammal. In some aspects, the patient is a human. In some aspects, the method improves survival of the patient. In some aspects, the method decreases the tumor volume in the patient.

In one embodiment, provided are methods of inhibiting iNOS in a patient in need thereof, the method comprising administering to the patient a therapeutically effective amount of a composition according to any one of the present embodiments. In some aspects, the methods comprise administering the composition once. In some aspects, the methods comprise administering the composition two or more times. In some aspects, administering comprises injecting the composition into the patient. In some aspects, the methods further comprise administering a second therapy. In some aspects, the patient is a mammal. In some aspects, the patient is a human.

In one embodiment, provided are methods of reducing VEGF levels in a patient in need thereof, the method comprising administering to the patient a therapeutically effective amount of a composition according to any one of the present embodiments. In some aspects, the VEGF levels are serum VEGF levels. In some aspects, the methods comprise administering the composition once. In some aspects, the methods comprise administering the composition two or more times. In some aspects, administering comprises injecting the composition into the patient. In some aspects, the methods further comprise administering a second therapy. In some aspects, the patient is a mammal. In some aspects, the patient is a human.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, the variation that exists among the study subjects, or a value that is within 10% of a stated value.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIGS. 1A-D. Chemical structures of small-molecule L-NIL and L-NIL multidomain peptide. Chemical structures of the small-molecule immunomodulatory drug L-NIL (FIG. 1A) and the designed L-NIL multidomain peptide (FIG. 1B) chemically derived from the lysine based peptide, $K_2(SL)_6K_2$(SEQ ID NO: 2), by converting the starting material's lysine side-chains to L-NIL acetamidine functional groups. (FIG. 1C) Graphic depicting the nanofibers formed by self-assembly of multidomain peptides into anti-parallel β-sheets, driven by hydrophobic packing and the formation of hydrogen-bonding networks between peptide backbones. Charged functional groups are displayed on the fiber surface and interact with phosphate counterions to extend and crosslink fibers. (FIG. 1D) Image of the hydrogel biomaterial that forms when the L-NIL-MDP is prepared at 1 wt. % in phosphate-containing buffer.

FIGS. 2A-C. L-NIL-MDP solid-phase synthesis scheme. (FIG. 2A) $K^{Mmt}_2(SL)_6K^{Mmt}_2$ (SEQ ID NO: 3) is synthesized on MBHA resin using standard solid-phase peptide chemistry. (FIG. 2B) Removal of the monomethoxytrityl protecting groups is performed using 10% acetic acid in TFE and DCM to yield deprotected $K_2(SL)_6K_2$ (SEQ ID NO: 2). (FIG. 2C) On resin conversion to L-NIL-MDP is achieved by acetimidation reaction with excess ethyl acetimidate and DiEA, followed by TFA cleavage from resin to yield free peptide.

FIGS. 3A-F. Chemical characterization data for the L-NIL-MDP biomaterial. (FIG. 3A) MALDI-mass spectrum showing successful synthesis of L-NIL-MDP, primarily composed of fully converted peptide (all four lysine side chains modified to L-NIL) with a small fraction possessing fewer modified side-chains. (FIG. 3B) Oscillatory rheology showing the successful formation of L-NIL-MDP hydrogel with a storage modulus (G') of ~300 Pa and loss modulus (G") of ~25 Pa, and with a shear recovery of ~86% 1 min after shearing event. (FIGS. 3C-D) Circular dichroism (FIG. 3C) and attenuated total reflectance Fourier transform infrared spectroscopy (FIG. 3D) spectra confirmed the formation of anti-parallel j-sheet secondary structure that closely matches spectra for the parent peptide K2-MDP, demonstrating no significant change in peptide structure upon conversion to L-NIL-MDP. (FIGS. 3E-F) Transmission electron microscopy images of (FIG. 3E) K2 MDP at 0.01 wt. % and (FIG. 3F) L-NIL-MDP at 0.02 wt. % shown at 40,000× magnification with scale bars=100 nm.

(FIG. 5A) Plot of % iNOS inhibition of RAW 264.7 cells stimulated with Lipopolysaccharide (LPS) and IFN-γ cultured in different surface conditions, showing chemical structures of key surface-exposed functional groups. (FIG. 5B) Quantification of relative inhibition activity; values are from two experiments and are mean±SD with three replicates tested per condition.

(FIG. 6A-C) L-NIL-MDP hydrogel 3 days post injection, with FIG. 6A showing a 4× panorama and FIGS. 6B-C showing representative zoomed 40× images of the core (FIG. 6B) followed by the periphery of the implant (FIG. 6C), denoted by the black boxes on the main image (same pattern follows in all series). (FIGS. 6D-F) hydrogel 7 days post injection; (FIGS. 6G-I) hydrogel 14 days post injection; (FIGS. 6J-L) hydrogel 21 days post injection. Scale bars are 1 mm in all 4× panoramas and 0.1 mm in all 40× images.

(FIGS. 7A-C) Immunostained implant images from left to right of L-NIL-MDP, K2-MDP, and R2-MDP respectively, 3 days post injection. (FIGS. 7D-F) Images from left to right of L-NIL-MDP, K2-MDP, and R2-MDP 7 days post injection. Scale bars=0.5 mm. (FIG. 7G) Quantification of relative nitrotyrosine signaling by mean pixel intensity analysis of implant areas, and statistical significance is noted as =p value ≤0.049, *=p value ≤0.005, and ****=p value ≤0.0002 (values are mean±SEM with n=3). Positive control was the staining intensity of an inflamed B16-F0 melanoma tumor section, and negative control was background staining of native subcutaneous tissue from isotype controls subtracted from all data sets. (FIG. 7H) Graph of nitrotyrosine staining intensity shown in (FIG. 7G) plotted vs. % iNOS knockdown data shown in FIGS. 5A-B for all cationic MDPs, demonstrating strong inverse correlation between the two separate data sets.

(FIG. 8A) Percent change in plasma VEGF concentration from normal levels observed in naive mice. Data shown are 5 days after treatment with 100 µL intratumoral injections of either HBSS buffer control, free L-NIL drug, K2-MDP hydrogel, or L-NIL-MDP hydrogel. In each group n=10 (except naive mice n=5), and statistical significance is noted as =p value ≤0.004, and **=p value ≤0.0002 (values are mean±SD). Significant VEGF reduction was observed in sera from mice treated with the L-NIL-MDP gel compared to all other tumor-bearing groups, restoring circulating VEGF concentrations to normal levels observed in naive healthy mice. (FIG. 8B) Raw VEGF serum levels in pg/mL representative of two experiments, with values equal to mean±SD (n=5).

(FIGS. 11A, 11C) Drug release profiles of cyclic dinucleotide ML RR-S2 CDA from various hydrogels systems, comparing commercially available alginate, hyaluronic acid (HyAcid), collagen, and Matrigel systems to synthesized MDPs $K_2(SL)_6K_2$ (SEQ ID NO: 2; STINGel), $E_2(SL)_6E_2$ (SEQ ID NO: 4), $O_5(SL)_6O_5$ (SEQ ID NO: 5), and L-NIL-MDP (SynerGel), with quantification shown in (FIG. 11B). All release data are shown as means±S.D. with n=3. Data for K2-MDP and collagen hydrogels are reproduced from our previous study for comparison (Leach et al., 2018). (FIG. 11D) Rheological storage modulus (G') of studied MDP hydrogels, showing bulk material strength was not predictive of drug release properties.

(FIGS. 12A-C) Viability of MOC1 cells cultured on L-NIL-MDP hydrogels. All cell-gel experiments were cultured under 200 µL of media and processed for live-dead viability assays at time-points of days 1, 3, and 7 (green live cell-Calcein AM; red dead cells-Ethidium-homodimer I; blue nuclei-Hoechst 33342). MOC1 cells were able to attach and easily proliferate on the L-NIL-MDP material. (FIGS. 12D-I) Masson's trichrome stained subcutaneous histology of hydrogels three days post injection in vivo. D-F are K2-MDP, G-I are L-NIL-MDP. Example areas of undegraded or non-infiltrated hydrogel have been marked by asterisks for clarity.

(FIG. 13A) Mean tumor growth until time of first mouse euthanization. (FIGS. 13B-G) Individual tumor growth curves for controls and SynerGel treated mice bearing established MOC1 oral tumors over course of study. Tumor rechallenge was at day 100 post-inoculation (indicated by dotted line). The number of tumor-bearing mice that were euthanized is listed above each plot. L-NIL-MDP+CDN (SynerGel) treated mice had decreased tumor growth. a, $p<0.01$ vs K2-MDP; b, $p<0.0001$ vs. HBSS, K2-MDP, L-NIL-MDP; #, $p<0.01$ vs. K2-MDP+CDN; c, $p<0.0001$ vs. HBSS, K2-MDP, K2-MDP+CDN and L-NIL-MDP.

(FIG. 15A) $K_2(SL)_6K_2$(SEQ ID NO: 2), (FIG. 15B) $E_2(SL)_6E_2$(SEQ ID NO: 4), (FIG. 15C) $O_5(SL)_6O_5$(SEQ ID NO: 5), (FIG. 15D) L-NIL-MDP $[K^{LNIL}(SL)_6 K^{LNIL}]$.

DETAILED DESCRIPTION

Figure 4:
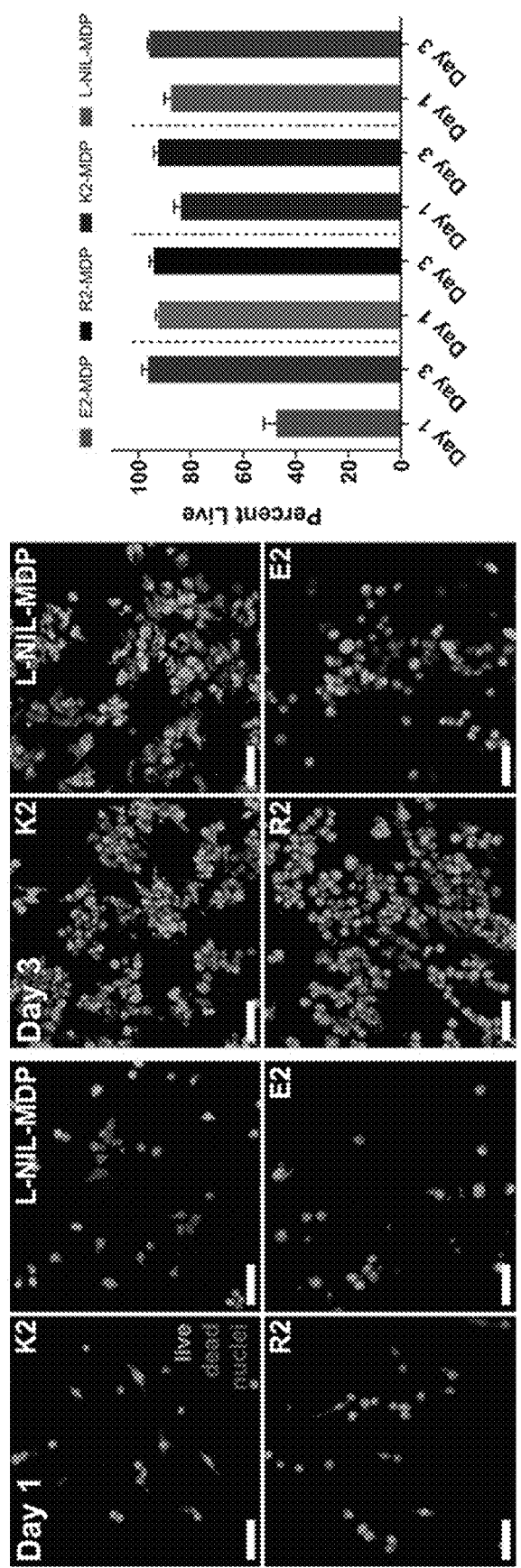
FIG. 4. Viability of cells grown on MDP hydrogels. RAW 264.7 cells were seeded on top of 70 µL hydrogel pucks under 200 µL of media (changed every two days) and processed under live-dead viability assays (green Calcein AM—live cells; red Ethidium-homodimer I—dead cells; blue Hoechst 33342- nuclei). Cells are shown to be able to attach and proliferate on all materials, though to a lesser degree on the anionic material E2 compared to the cationic materials K2, R2, and L-NIL-MDP. Day 1 images are shown on the left, day 3 images are shown in the center, and quantification of cell viability is shown on the right (values are mean±SD with n=3 images). All scale bars are 50 µm.

While small-molecule immune modulators hold promise for cancer immunotherapy, systemic delivery of such drugs is limited by a variety of factors, such as physiologic clearance and drug neutralization, which strongly limit intratumoral drug localization. As a result, these drugs often require frequent dosing schedules or high concentrations, which can promote a variety of side-effects. To address these limitations, a bioactive peptide biomaterial that provides a platform for the incorporation and continuous release of an immunomodulatory agent over many weeks is provided herein. To this end, a peptide scaffold was chemically transformed to provide the pharmacological activity of the immunomodulatory small-molecule inhibitor of inducible nitric oxide synthase (iNOS) N6-(1-iminoethyl)-L-lysine, or L-NIL, using the reactive lysine side-chains of a MultiDomain Peptide (MDP).

The resulting self-assembling L-NIL-MDP biomaterial was shown to be compatible with cell growth and degrade in vivo over three weeks. Multiple characterization assays confirmed durable L-NIL bioactivity. Significantly, single intratumoral injections of the L-NIL-MDP hydrogel alone showed sustained reduction of serum levels of vascular endothelial growth factor (VEGF), a known target of iNOS, in mice bearing B16-F0 melanoma tumors.

The L-NIL-MDP therefore possesses unique utility over the current standard of L-NIL small-molecule drug treatment, critically showing the ability to create an extended systemic response not achievable with L-NIL alone. As an immunotherapeutic biomaterial (rather than a traditional soluble small-molecule), it generates a biological effect that is durable, controlled, and inherent to the hydrogel implant that can remain in its injected location for over 3 weeks, compared to the freely diffusible drug whose effects are typically lost within 24 hours. The useful properties of the L-NIL-MDP as a bioactive carrier material can be combined with additional loaded agents, creating extended release, multi-component combination therapies. This includes loading the hydrogel during the gelation process with chemotherapy agents, STING agonists, checkpoint inhibitor antibodies, or other anti-cancer drugs (e.g., cyclophosphamides, CpG nucleotides, activated T cells, inflammatory cytokines, inflammatory chemokines) that would benefit from controlled intratumoral administration. The L-NIL-MDP material is uniquely suited to be used in creating an all-in-one, injectable combination therapy platform suitable for application to a variety of cancer disease states.

One example of a loaded hydrogel therapy provided herein is peptide-based immunotherapy termed SynerGel: an injectable, biomaterial-based platform for intratumoral delivery. This system is composed of a drug-mimicking peptide hydrogel named L-NIL-MDP, derived from an inhibitor of inducible Nitric Oxide Synthase (iNOS), N6-(1-iminoethyl)-L-lysine (L-NIL), and loaded with a cyclic dinucleotide Stimulator of Interferon Genes (STING) agonist. The biomaterial delivery vehicle combines inherent iNOS inhibition with controlled delivery of a STING agonist, allowing for immune-mediated elimination of established treatment-resistant tumors.

I. SELF-ASSEMBLING PEPTIDE HYDROGELS

Within the paradigm of cancer research, it is increasingly clear that standard drug administration strategies are insufficient to resolve advanced disease states. While monotherapies using small-molecule drugs and systemically delivered therapeutics (whether oral or intravenous) can effectively treat many classes of diseases, cancer represents a uniquely complex challenge to modem medicine that demands a complex response from researchers and clinicians (Dellacherie et al., 2019; Brudno et al., 2018). Among many obstacles that must be overcome, cancer cells are known to develop various mechanisms that promote their survival and proliferation, including avoidance of apoptosis (Hanahan et al., 2011), evasion from detection by the immune system (Berzofsky et al., 2004), inhibition of effector immune cells (Chen & Mellman, 2013), and the development of drug resistance (Housman et al., 2014). One strategy researchers are using to pursue more advanced treatment systems combines the unique strengths of anti-cancer immunotherapies and biomaterial-based delivery vehicles (Leach et al., 2019; Bookstaver et al., 2018).

The customizable nature of biomaterials makes them uniquely suited to be combined with anti-cancer immunotherapy agents (Dellacherie et al., 2019; Wang & Mooney, 2018). Current biomaterial strategies are often designed as hard implantable scaffolds for long-term therapy availability, or as soft injectable hydrogels that can localize and release agents anywhere a needle can reach (Leach et al., 2019). Biomaterials can be developed to load and deliver practically any therapeutic payload (whether small-molecules, biologics, or cells), using covalent bonds or non-covalent interactions to control the availability and release of bioactive agents (Bookstaver et al., 2018). Among the variety of biomaterial strategies currently being deployed, peptide-based biomaterials are an ideal class of materials for immunotherapy applications. Not only do they possess an easily customizable structure due to the modular nature of their amino acid building blocks, but their composition is inherently biocompatible and biodegradable, and can be tailored to generate greater or lesser degrees of immune-reactivity based on the desired application (Cui et al., 2010; Collier & Segura, 2011; Moore & Hartgerink, 2017).

Self-assembling peptides have been extensively studied because of their relationship to protein folding and assembly. These peptides can be designed to spontaneously self-assemble into fibrous nanomaterials that have a chemical composition and nanostructure that is readily interfaced with living systems and possess material properties that mimic the extracellular matrix (Lutolf & Hubbell, 2005). The resulting bio-interactive nature of these supramolecular materials is useful in biomedical applications, such as controlled drug and protein delivery, cell encapsulation, and tissue regeneration (Webber et al., 2015; Rad-Malekshahi et al., 2016; Leach et al., 2018). Several peptide designs have been created to self-assemble into nanoribbons, monolayers or nanofibers, which utilize amphiphilic and ionic domains to govern their supramolecular structure (Aggeli et al., 2003; Powers et al., 2002; Holmes et al., 2000; Cormier et al., 2013; Pochan et al., 2003; Hartgerink et al., 2001). Generally, self-assembling peptide design has required the incorporation of charged amino acids into the peptide sequence as a mechanism to control assembly and material properties by stimuli such as pH and ionic strength (Chockalingam et al., 2007; Micklitsch et al., 2011; Schneider et al., 2002).

Provided herein are peptide-based biomaterials to improve the biological presentation and inhibitory action of a small-molecule inhibitor with immunomodulatory properties called N6-(1-iminoethyl)-L-lysine, or L-NIL (FIG. 1A). Biomaterial-based L-NIL activity and extended delivery are expected to address some of the issues currently limiting the therapeutic applications of iNOS inhibition. Also contemplated are peptide-based biomaterials incorporating any of a variety of iNOS inhibitors, such as, for example,

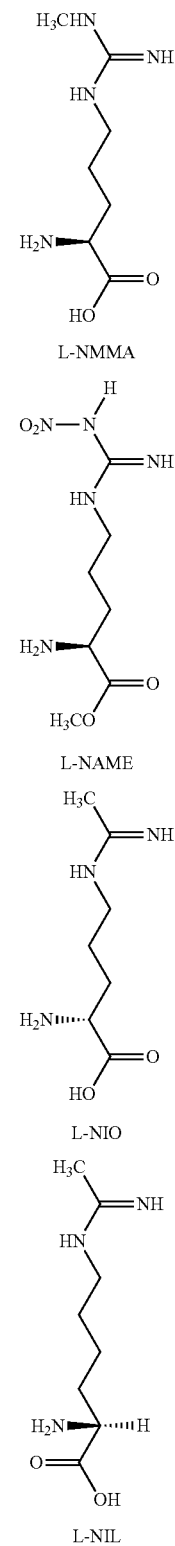

L-NMMA

L-NAME

L-NIO

L-NIL

-continued

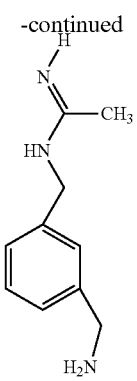
1400W

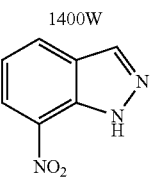
7-NI

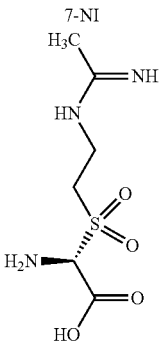
GW273629

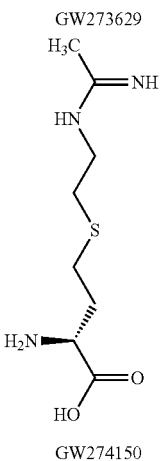
GW274150

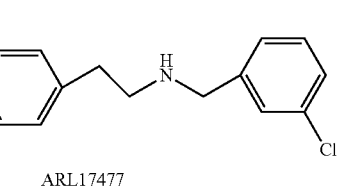
ARL17477

(Deshpande et al., 2012).

Such as MDP can be synthesized in many variations. For example, MDPs bearing only one, two, or three iNOS inhibitor groups on each peptide can be made in order to provide lower dose control. In addition, MDPs with a larger number of iNOS inhibitor groups (e.g., seven to eight iNOS inhibitor functional groups per peptide) could be synthesized to provide increased iNOS inhibitory activity. As such, many sequence variations as well as alternative areas on the peptide backbone on which to display iNOS inhibitory function groups (e.g., directly on the N or C terminus) are possible. In MDPs bearing more than one iNOS inhibitor group, the various iNOS inhibitor groups may all be of the same iNOS inhibitor group or may be different iNOS inhibitor groups.

Over the course of the past decade, a versatile portfolio of MultiDomain Peptides (MDPs), which are a family of rationally designed peptides that self-assemble in aqueous solution to form nanofibrous networks capable of mimicking the extracellular matrix (ECM), have been developed (Moore & Hartgerink, 2017; Aulisa et al., 2009). MDP self-assembly is driven by a central amphiphilic core of alternating hydrophobic (often leucine) and hydrophilic (often serine) amino acids, and anti-parallel j-sheet networks form as a result of peptide-backbone hydrogen bonding. When buffers containing multivalent counterions are added (such as phosphate ions in PBS), these synthesized MDPs form crosslinked and highly entangled nanofibers, resulting in soft ECM-like hydrogels ideal for use as injectable biomaterials (FIGS. 1B-D) (Aulisa et al., 2009). The chemistry and functionality of these nanofibrous peptide biomaterials can be highly customized for various extended drug delivery applications, including cancer immunotherapy (Kumar et al., 2015; Li et al., 2016; Wickremasinghe et al., 2014; Leach et al., 2018).

By way of example, the chemical structure of a peptide hydrogel was transformed such that it could mimic the bioactivity of the drug L-NIL, thereby converting the scaffold itself into a pharmacologic agent. The immunomodulatory drug L-NIL has a chemical structure derived from the natural amino acid lysine. The L-NIL acetamidine functional group, like lysine's amine, critically retains a positive charge at physiological pH. This cationic charge was predicted to allow for control of the self-assembly of a custom L-NIL acetamidine-based multidomain peptide via charge repulsion, a critical aspect of the MDP design. Here, it is shown that the "L-NIL-MDP" hydrogel possesses unique chemical and mechanical properties that make it an advantageous immunotherapy delivery platform, as it shows inherent drug bioactivity, remains in its implanted location for up to three weeks, and can create a durable systemic affect observable in reduced serum VEGF levels in a murine melanoma tumor model. Furthermore, the cationic material design could allow for the non-covalent importation of other bioactive agents within the hydrogel, similar to other hydrogels used to deliver potent immunotherapy drugs such as STING agonists (Leach et al., 2018). However, what was previously only a carrier vehicle for the loading of exogenous drugs can now display its own inherent axis of therapeutic action that will easily facilitate combination therapy designs in the future.

L-NIL-MDP can be synthesized in many variations. For example, L-NIL-MDPs bearing only one, two, or three L-NIL drug units on each peptide can be made in order to provide lower dose control. In addition, MDPs with a larger number of L-NIL groups (e.g., seven to eight L-NIL functional groups per peptide) could be synthesized to provide increased L-NIL activity. As such, many sequence variations as well as alternative areas on the peptide backbone on which to display L-NIL function groups (e.g., directly on the N or C terminus) are possible.

L-NIL-MDP is an effective, bioactive carrier material for immunotherapies in an established tumor model, requiring only a single intratumoral injection of SynerGel for full elimination of 4-5 mm tumors. The cationic properties of the L-NIL-MDP hydrogel allow it to extend the release of anionic cyclic dinucleotides, with significantly greater controlled release compared to various other hydrogel systems. The combination of the L-NIL-MDP hydrogel with its inherent iNOS inhibition and the controlled release of STING agonist immunotherapy successfully increased the survival of MOC1-tumor burdened mice. The L-NIL-MDP biomaterial can be used as an alternative to treatment strategies that utilize the small molecule drug L-NIL. These formulations will continue to be designed for long-lasting, immune cell-infiltrated biomaterial immunotherapy at the tumor site, allowing for transformation of the local immunosuppressive microenvironment to a more treatment-responsive tumor.

II. STING AND STING AGONISTS

Stimulator of interferon genes (STING), also known as transmembrane protein 173 (TMEM173) and MPYS/MITA/ERIS, is a protein that in humans is encoded by the TMEM173 gene. STING plays an important role in innate immunity. STING induces type I interferon production when cells are infected with intracellular pathogens, such as viruses, mycobacteria and intracellular parasites. Type I interferon, mediated by STING, protects infected cells and nearby cells from local infection by binding to the same cell that secretes it (autocrine signaling) and nearby cells (paracrine signaling). STING is expressed in hematopoietic cells in peripheral lymphoid tissues, including T lymphocytes, NK cells, myeloid cells and monocytes. It has also been shown that STING is highly expressed in lung, ovary, heart, smooth muscle, retina, bone marrow and vagina. STING has been shown to bind directly to cyclic di-GMP, and this recognition leads to the production of cytokines, such as type I interferon.

Cyclic dinucleotides (CDNs) have been described as having immunomodulatory properties that could be exploited in an immunotherapy treatment. This immunomodulatory activity is typically the induction of cytokines and/or activation of immune cells in vitro or in vivo. Examples of cyclic dinucleotides include c-AIMP, (3',2')c-AIMP, (2',2')c-AIMP, (2',3')c-AIMP, c-AIMP(S), c-(dAMP-dIMP), c-(dAMP-2'FdIMP), c-(2'FdAMP-2'FdIMP), (2',3')c-(AMP-2'FdIMP), c-[2'FdAMP(S)-2'FdIMP(S)] and c-[2'FdAMP(S)-2'FdIMP(S)](POM)$_2$ or a pharmaceutically acceptable salt or prodrug thereof. Particularly, the cyclic dinucleotide is selected from the group consisting of: c-AIMP, c-(2'FdAMP-2'FdIMP), c-AIMP(S), c-[2'FdAMP(S)-2'FdIMP(S)] and c-[2'FdAMP(S)- 2'FdIMP(S)](POM)$_2$.

III. IMMUNOMODULATORY AGENTS

Immunomodulatory agents include immune checkpoint inhibitors, agonists of co-stimulatory molecules, and antagonists of immune inhibitory molecules. The immunomodulatory agents may be drugs, such as small molecules, recombinant forms of ligand or receptors, or antibodies, such as human antibodies (e.g., International Patent Publication WO2015/016718; Pardoll, Nat Rev Cancer, 12(4): 252-264, 2012; both incorporated herein by reference). Known inhibitors of immune checkpoint proteins or analogs thereof may be used, in particular chimerized, humanized, or human forms of antibodies may be used. As the skilled person will know, alternative and/or equivalent names may be in use for certain antibodies mentioned in the present disclosure. Such alternative and/or equivalent names are interchangeable in the context of the present disclosure. For example, it is known that lambrolizumab is also known under the alternative and equivalent names MK-3475 and pembrolizumab.

Co-stimulatory molecules are ligands that interact with receptors on the surface of the immune cells, e.g., CD28, 4-1BB, OX40 (also known as CD134), ICOS, and GITR. As an example, the complete protein sequence of human OX40 has Genbank accession number NP_003318. In some embodiments, the immunomodulatory agent is an anti-OX40 antibody (e.g., a human antibody, a humanized antibody, or a chimeric antibody), an antigen binding fragment thereof, an immunoadhesin, a fusion protein, or oligopeptide. Anti-human-OX40 antibodies (or VH and/or VL domains derived therefrom) suitable for use in the present methods can be generated using methods well known in the art. Alternatively, art recognized anti-OX40 antibodies can be used. An exemplary anti-OX40 antibody is PF-04518600 (see, e.g., WO 2017/130076). ATOR-1015 is a bispecific antibody targeting CTLA4 and OX40 (see, e.g., WO 2017/182672, WO 2018/091740, WO 2018/202649, WO 2018/002339).

Another co-stimulatory molecule that can be targeted in the methods provided herein is ICOS, also known as CD278. The complete protein sequence of human ICOS has Genbank accession number NP_036224. In some embodiments, the immune checkpoint inhibitor is an anti-ICOS antibody (e.g., a human antibody, a humanized antibody, or a chimeric antibody), an antigen binding fragment thereof, an immunoadhesin, a fusion protein, or oligopeptide. Anti-human-ICOS antibodies (or VH and/or VL domains derived therefrom) suitable for use in the present methods can be generated using methods well known in the art. Alternatively, art recognized anti-ICOS antibodies can be used. Exemplary anti-ICOS antibodies include JTX-2011 (see, e.g., WO 2016/154177, WO 2018/187191) and GSK3359609 (see, e.g., WO 2016/059602).

Yet another co-stimulatory molecule that can be targeted in the methods provided herein is glucocorticoid-induced tumour necrosis factor receptor-related protein (GITR), also known as TNFRSF18 and AITR. The complete protein sequence of human GITR has Genbank accession number NP_004186. In some embodiments, the immunomodulatory agent is an anti-GITR antibody (e.g., a human antibody, a humanized antibody, or a chimeric antibody), an antigen binding fragment thereof, an immunoadhesin, a fusion protein, or oligopeptide. Anti-human-GITR antibodies (or VH and/or VL domains derived therefrom) suitable for use in the present methods can be generated using methods well known in the art. Alternatively, art recognized anti-GITR antibodies can be used. An exemplary anti-GITR antibody is TRX518 (see, e.g., WO 2006/105021).

Immune checkpoint proteins that may be targeted by immune checkpoint blockade include adenosine A2A receptor (A2AR), B7-H3 (also known as CD276), B and T lymphocyte attenuator (BTLA), CCL5, CD27, CD38, CD8A, CMKLR1, cytotoxic T-lymphocyte-associated protein 4 (CTLA-4, also known as CD152), CXCL9, CXCR5, HLA-DRB1, HLA-DQA1, HLA-E, killer-cell immunoglobulin (KIR), lymphocyte activation gene-3 (LAG-3, also known as CD223), Mer tyrosine kinase (MerTK), NKG7, programmed death 1 (PD-1), programmed death-ligand 1 (PD-L1, also known as CD274), PDCD1LG2, PSMB10, STAT1, T cell immunoreceptor with Ig and ITIM domains (TIGIT), T-cell immunoglobulin domain and mucin domain 3 (TIM-3), and V-domain Ig suppressor of T cell activation (VISTA, also known as C10orf54). In particular, immune checkpoint inhibitors targeting the PD-1 axis and/or CTLA-4 have received FDA approval broadly across diverse cancer types.

In some embodiments, a PD-1 binding antagonist is a molecule that inhibits the binding of PD-1 to its ligand binding partners. In a specific aspect, the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, a PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or an oligopeptide. Exemplary antibodies are described in U.S. Pat. Nos. 8,735,553, 8,354,509, and 8,008,449, all of which are incorporated herein by reference. Other PD-1 axis antagonists for use in the methods provided herein are known in the art, such as described in U.S. Patent Application Publication Nos. 2014/0294898, 2014/022021, and 2011/0008369, all of which are incorporated herein by reference.

In some embodiments, a PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence)). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PD-L2-Fc fusion soluble receptor described in WO2010/027827 and WO2011/066342.

Another immune checkpoint protein that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA-4 is similar to the T-cell co-stimulatory protein, CD28, and both molecules bind to CD80 and CD86, also called B7-1 and B7-2 respectively, on antigen-presenting cells. CTLA-4 transmits an inhibitory signal to T cells, whereas CD28 transmits a stimulatory signal. Intracellular CTLA-4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide. Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in U.S. Pat. No. 8,119,129; PCT Publn. Nos. WO 01/14424, WO 98/42752, WO 00/37504 (CP675, 206, also known as tremelimumab; formerly ticilimumab); U.S. Pat. No. 6,207,156; Hurwitz et al. (1998) *Proc Natl Acad Sci USA*, 95(17): 10067-10071; Camacho et al. (2004) *J Clin Oncology*, 22(145): Abstract No. 2505 (antibody CP-675206); and Mokyr et al. (1998) *Cancer Res*, 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001/014424, WO2000/037504, and U.S. Pat. No. 8,017,114; all incorporated herein by reference.

An exemplary anti-CTLA-4 antibody is ipilimumab (also known as 10DI, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2, and CDR3 domains of the VL region of ipilimumab. In another embodiment, the antibody competes for binding with and/or binds to the same epitope on CTLA-4 as the above-mentioned antibodies. In another embodiment, the antibody has an at least about 90% variable region amino acid sequence identity with the above-mentioned antibodies (e.g., at least about 90%, 95%, or 99% variable region identity with ipilimumab). Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

Another immune checkpoint protein that can be targeted in the methods provided herein is lymphocyte-activation gene 3 (LAG-3), also known as CD223. The complete protein sequence of human LAG-3 has the Genbank accession number NP-002277. LAG-3 is found on the surface of activated T cells, natural killer cells, B cells, and plasmacytoid dendritic cells. LAG-3 acts as an "off" switch when bound to MHC class II on the surface of antigen-presenting cells. Inhibition of LAG-3 both activates effector T cells and inhibitor regulatory T cells. In some embodiments, the immune checkpoint inhibitor is an anti-LAG-3 antibody (e.g., a human antibody, a humanized antibody, or a chimeric antibody), an antigen binding fragment thereof, an immunoadhesin, a fusion protein, or oligopeptide. Anti-human-LAG-3 antibodies (or VH and/or VL domains derived therefrom) suitable for use in the present methods can be generated using methods well known in the art. Alternatively, art recognized anti-LAG-3 antibodies can be used. An exemplary anti-LAG-3 antibody is relatlimab (also known as BMS-986016) or antigen binding fragments and variants thereof (see, e.g., WO 2015/116539). Other exemplary anti-LAG-3 antibodies include TSR-033 (see, e.g., WO 2018/201096), MK-4280, and REGN3767. MGD013 is an anti-LAG-3/PD-1 bispecific antibody described in WO 2017/019846. FS118 is an anti-LAG-3/PD-L1 bispecific antibody described in WO 2017/220569.

Another immune checkpoint protein that can be targeted in the methods provided herein is V-domain Ig suppressor of T cell activation (VISTA), also known as C10orf54. The complete protein sequence of human VISTA has the Genbank accession number NP_071436. VISTA is found on white blood cells and inhibits T cell effector function. In some embodiments, the immune checkpoint inhibitor is an anti-VISTA3 antibody (e.g., a human antibody, a humanized antibody, or a chimeric antibody), an antigen binding fragment thereof, an immunoadhesin, a fusion protein, or oligopeptide. Anti-human-VISTA antibodies (or VH and/or VL domains derived therefrom) suitable for use in the present methods can be generated using methods well known in the art. Alternatively, art recognized anti-VISTA antibodies can be used. An exemplary anti-VISTA antibody is JNJ-61610588 (also known as onvatilimab) (see, e.g., WO 2015/097536, WO 2016/207717, WO 2017/137830, WO 2017/175058). VISTA can also be inhibited with the small molecule CA-170, which selectively targets both PD-L1 and VISTA (see, e.g., WO 2015/033299, WO 2015/033301).

Another immune checkpoint protein that can be targeted in the methods provided herein is CD38. The complete protein sequence of human CD38 has Genbank accession number NP_001766. In some embodiments, the immune checkpoint inhibitor is an anti-CD38 antibody (e.g., a human antibody, a humanized antibody, or a chimeric antibody), an antigen binding fragment thereof, an immunoadhesin, a fusion protein, or oligopeptide. Anti-human-CD38 antibodies (or VH and/or VL domains derived therefrom) suitable for use in the present methods can be generated using methods well known in the art. Alternatively, art recognized anti-CD38 antibodies can be used. An exemplary anti-CD38 antibody is daratumumab (see, e.g., U.S. Pat. No. 7,829,673).

Another immune checkpoint protein that can be targeted in the methods provided herein is T cell immunoreceptor with Ig and ITIM domains (TIGIT). The complete protein sequence of human TIGIT has Genbank accession number NP_776160. In some embodiments, the immune checkpoint inhibitor is an anti-TIGIT antibody (e.g., a human antibody, a humanized antibody, or a chimeric antibody), an antigen binding fragment thereof, an immunoadhesin, a fusion protein, or oligopeptide. Anti-human-TIGIT antibodies (or VH and/or VL domains derived therefrom) suitable for use in the present methods can be generated using methods well known in the art. Alternatively, art recognized anti-TIGIT antibodies can be used. An exemplary anti-TIGIT antibody is MK-7684 (see, e.g., WO 2017/030823, WO 2016/028656).

Other immune inhibitory molecules that can be targeted for immunomodulation include STAT3 and indoleamine 2,3-dioxygenase (IDO). By way of example, the complete protein sequence of human IDO has Genbank accession number NP_002155. In some embodiments, the immunomodulatory agent is a small molecule IDO inhibitor. Exemplary small molecules include BMS-986205, epacadostat (INCB24360), and navoximod (GDC-0919).

IV. PHARMACEUTICAL FORMULATIONS

The provided multidomain peptides can be combined with a pharmaceutically acceptable carrier or vehicle for administration to human or animal subjects. In some embodiments, more than one multidomain peptide or peptide analog can be combined to form a single preparation. The multidomain peptides or peptide analogs can be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and nonaqueous sterile injection solutions which may contain anti-oxidants, buffers, bacteriostats and solutes; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition.

In certain, embodiments, unit dosage formulations are those containing a dose or unit, or an appropriate fraction thereof, of the administered ingredient. It should be understood that, in addition to the ingredients particularly mentioned above, formulations encompassed herein may include other agents commonly used by one of ordinary skill in the art.

The pharmaceutical compositions provided herein may be administered through different routes, such as parenteral, intraperitoneal, intramuscular, subcutaneous, intradermal, submucosal, intramucosal, and intratumoral. It may be desirable to administer the pharmaceutical compositions locally to the area in need of treatment. This may be achieved by, for example, and not by way of limitation, local or regional infusion or perfusion during surgery, injection, or implant. In one embodiment, administration can be by direct injection at the site (or former site) of a tissue that is to be treated.

The amount of the pharmaceutical compositions that will be effective depends on the nature of the disorder or condition to be treated, as well as the stage of the disorder or condition. Effective amounts can be determined by standard clinical techniques. The precise dose to be employed in the formulation will also depend on the route of administration, and should be decided according to the judgment of the health care practitioner and each subject's circumstances.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the subject undergoing therapy.

The pharmaceutical compositions of the present disclosure can be administered at about the same dose throughout a treatment period, in an escalating dose regimen, or in a loading-dose regime (e.g., in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art. The volume of administration will vary depending on the route of administration. Those of ordinary skill in the art will know appropriate volumes for different routes of administration.

V. METHODS OF TREATMENT

The present invention provides methods of treating a cancer patient with L-NIL-MDP as provided herein. Such treatment may also be in combination with another therapeutic regime, such as chemotherapy or immunotherapy.

The term "subject" or "patient" as used herein refers to any individual to which the subject methods are performed. Generally the patient is human, although as will be appreciated by those in the art, the patient may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of patient.

"Treatment" and "treating" refer to administration or application of a therapeutic agent to a subject or performance of a procedure or modality on a subject for the purpose of obtaining a therapeutic benefit of a disease or health-related condition. For example, a treatment may include administration chemotherapy, immunotherapy, radiotherapy, performance of surgery, or any combination thereof.

The methods described herein are useful in treating cancer. Generally, the terms "cancer" and "cancerous" refer to or describe the physiological condition in mammals that is typically characterized by unregulated cell growth. More specifically, cancers that are treated in connection with the methods provided herein include, but are not limited to, solid tumors, metastatic cancers, or non-metastatic cancers. In certain embodiments, the cancer may originate in the lung, kidney, bladder, blood, bone, bone marrow, brain, breast, colon, esophagus, duodenum, small intestine, large intestine, colon, rectum, anus, gum, head, liver, nasopharynx, neck, ovary, pancreas, prostate, skin, stomach, testis, tongue, or uterus.

The cancer may specifically be of the following histological type, though it is not limited to these: neoplasm, malignant; carcinoma; non-small cell lung cancer; renal cancer; renal cell carcinoma; clear cell renal cell carcinoma; lymphoma; blastoma; sarcoma; carcinoma, undifferentiated; meningioma; brain cancer; oropharyngeal cancer; nasopharyngeal cancer; biliary cancer; pheochromocytoma; pancreatic islet cell cancer; Li-Fraumeni tumor; thyroid cancer; parathyroid cancer; pituitary tumor; adrenal gland tumor; osteogenic sarcoma tumor; neuroendocrine tumor; breast cancer; lung cancer; head and neck cancer; prostate cancer; esophageal cancer; tracheal cancer; liver cancer; bladder cancer; stomach cancer; pancreatic cancer; ovarian cancer; uterine cancer; cervical cancer; testicular cancer; colon cancer; rectal cancer; skin cancer; giant and spindle cell carcinoma; small cell carcinoma; small cell lung cancer; papillary carcinoma; oral cancer; oropharyngeal cancer; nasopharyngeal cancer; respiratory cancer; urogenital cancer; squamous cell carcinoma; lymphoepithelial carcinoma; basal cell carcinoma; pilomatrix carcinoma; transitional cell carcinoma; papillary transitional cell carcinoma; adenocarcinoma; gastrointestinal cancer; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma with squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; lentigo maligna melanoma; acral lentiginous melanoma; nodular melanoma; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; an endocrine or neuroendocrine cancer or hematopoietic cancer; pinealoma, malignant; chordoma; central or peripheral nervous system tissue cancer; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; B-cell lymphoma; malignant lymphoma; Hodgkin's disease; Hodgkin's; low grade/follicular non-Hodgkin's lymphoma; paragranuloma; malignant lymphoma, small lymphocytic; malignant lymphoma, large cell, diffuse; malignant lymphoma, follicular; mycosis fungoides; mantle cell lymphoma; Waldenstrom's macroglobulinemia; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; chronic lymphocytic leukemia (CLL); acute lymphoblastic leukemia (ALL); Hairy cell leukemia; chronic myeloblastic leukemia; and hairy cell leukemia.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the invasiveness of a tumor, reduction in the growth rate of the cancer, or prevention of metastasis. Treatment of cancer may also refer to prolonging survival of a subject with cancer.

Likewise, an effective response of a patient or a patient's "responsiveness" to treatment refers to the clinical or therapeutic benefit imparted to a patient at risk for, or suffering from, a disease or disorder. Such benefit may include cellular or biological responses, a complete response, a partial response, a stable disease (without progression or relapse), or a response with a later relapse. For example, an effective response can be reduced tumor size or progression-free survival in a patient diagnosed with cancer.

Regarding neoplastic condition treatment, depending on the stage of the neoplastic condition, neoplastic condition treatment involves one or a combination of the following therapies: surgery to remove the neoplastic tissue, radiation therapy, and chemotherapy. Other therapeutic regimens may be combined with the administration of the anticancer agents, e.g., therapeutic compositions and chemotherapeutic agents. For example, the patient to be treated with such anti-cancer agents may also receive radiation therapy and/or may undergo surgery.

For the treatment of disease, the appropriate dosage of a therapeutic composition will depend on the type of disease to be treated, as defined above, the severity and course of the disease, previous therapy, the patient's clinical history and response to the agent, and the discretion of the physician. The agent may be suitably administered to the patient at one time or over a series of treatments.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. A tissue, tumor, or cell can be contacted with one or more compositions or pharmacological formulation(s) comprising one or more of the agents or by contacting the tissue, tumor, and/or cell with two or more distinct compositions or formulations. Also, it is contemplated that such a combination therapy can be used in conjunction with radiotherapy, surgical therapy, or immunotherapy.

Administration in combination can include simultaneous administration of two or more agents in the same dosage form, simultaneous administration in separate dosage forms, and separate administration. That is, the subject therapeutic composition and another therapeutic agent can be formulated together in the same dosage form and administered simultaneously. Alternatively, subject therapeutic composition and another therapeutic agent can be simultaneously administered, wherein both the agents are present in separate formulations. In another alternative, the therapeutic agent can be administered just followed by the other therapeutic agent or vice versa. In the separate administration protocol, the subject therapeutic composition and another therapeutic agent may be administered a few minutes apart, or a few hours apart, or a few days apart.

An anti-cancer first treatment may be administered before, during, after, or in various combinations relative to a second anti-cancer treatment. The administrations may be in intervals ranging from concurrently to minutes to days to weeks. In embodiments where the first treatment is provided to a patient separately from the second treatment, one would generally ensure that a significant period of time did not expire between the time of each delivery, such that the two compounds would still be able to exert an advantageously combined effect on the patient. In such instances, it is contemplated that one may provide a patient with the first therapy and the second therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below L-NIL-MDP is "A" and another anti-cancer therapy is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A B/A/B/A B/A/A/B A/A/A/B B/A/A/A A/B/A/A A/A/B/A

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy.

A. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gamma1I and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DFMO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

B. Immunotherapy

The skilled artisan will understand that additional immunotherapies may be used in combination or in conjunction with methods of the invention. In the context of cancer treatment, immunotherapeutics, generally, rely on the use of immune effector cells and molecules to target and destroy cancer cells. Rituximab (Rituxan®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., Mycobacterium bovis, Plasmodium falciparum, dinitrochlorobenzene, and aromatic compounds (U.S. Pat. Nos. 5,801,005 and 5,739, 169; Hui and Hashimoto, Infection Immun., 66(11):5329-5336, 1998; Christodoulides et al., Microbiology, 144(Pt 11):3027-3037, 1998); cytokine therapy, e.g., interferons α, β, and γ, IL-1, GM-CSF, and TNF (Bukowski et al., Clinical Cancer Res., 4(10):2337-2347, 1998; Davidson et al., J. Immunother., 21(5):389-398, 1998; Hellstrand et al., Acta Oncologica, 37(4):347-353, 1998); gene therapy, e.g., TNF, IL-1, IL-2, and p53 (Qin et al., Proc. Natl. Acad. Sci. USA, 95(24):14411-14416, 1998; Austin-Ward and Villaseca, Revista Medica de Chile, 126(7):838-845, 1998; U.S. Pat. Nos. 5,830,880 and 5,846,945); and monoclonal antibodies, e.g., anti-CD20, anti-ganglioside GM2, and anti-p185 (Hanibuchi et al., Int. J. Cancer, 78(4):480-485, 1998; U.S. Pat. No. 5,824,311). It is contemplated that one or more anti-cancer therapies may be employed with the antibody therapies described herein.

In some embodiment, the immune therapy could be adoptive immunotherapy, which involves the transfer of autologous antigen-specific T cells or other immune cells (e.g., natural killer "NK" cells and NK T cells) generated ex vivo. The T cells used for adoptive immunotherapy can be generated either by expansion of antigen-specific T cells or redirection of T cells through genetic engineering. Isolation and transfer of tumor specific T cells has been shown to be successful in treating melanoma. Novel specificities in T cells have been successfully generated through the genetic transfer of transgenic T cell receptors or chimeric antigen receptors (CARs). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. CARs have successfully allowed T cells to be redirected against antigens expressed at the surface of tumor cells from various malignancies including lymphomas and solid tumors.

In one embodiment, the present application provides for a combination therapy for the treatment of cancer wherein the combination therapy comprises adoptive T cell therapy and/or a checkpoint inhibitor. In one aspect, the adoptive T cell therapy comprises autologous and/or allogenic T-cells. In another aspect, the autologous and/or allogenic T-cells are targeted against tumor antigens. Checkpoint inhibitors are discussed in greater detail above.

C. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

D. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present invention, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with certain aspects of the present invention to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present invention to improve the treatment efficacy.

VI. KITS

Kits are envisioned containing peptides or hydrogels of the present invention. The kit may comprise reagents required for the formation of or the delivery of the hydrogel. The kit may also comprise a suitable container means, which is a container that will not react with components of the kit, such as an eppendorf tube, a syringe, a bottle, or a tube. The container may be made from sterilizable materials such as plastic or glass. The kit may further include an instruction sheet that outlines the procedural steps of the methods, such as the same procedures as described herein or are otherwise known to those of ordinary skill.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials & Methods for Examples 2-5

Peptide synthesis, L-NIL-MDP reaction, and product purification. Peptide synthesis reagents were purchased from EMD Chemicals (Philadelphia, PA). A combination of manual synthesis and an Apex Focus XC (Aapptec) automatic synthesizer was used to synthesize the multi-domain peptides $K_2(SL)_6K_2$ (SEQ ID NO: 2; K2-MDP), $E_2(SL)_6E_2$ (SEQ ID NO: 4; E2-MDP), $R_2(SL)_6R_2$ (SEQ ID NO: 6; R2-MDP) and the precursor to the L-NIL-MDP, $K^{Mmt}_2(SL)_6K^{Mmt}_2$ (SEQ ID NO: 3), where Mmt represents acid-labile monomethoxytrityl protecting groups on the lysine side-chains. All peptides were synthesized according to standard F-MOC chemistry using solid-phase peptide synthesis methods previously published (Dong et al., 2007). All peptides were N-terminally acetylated and C-terminally amidated.

The following method was used to convert $K^{Mmt}_2(SL)_6K^{Mmt}_2$ (SEQ ID NO: 3) on low-loading MBHA resin to the L-NIL-MDP before TFA cleavage (FIGS. 2A-C). Deprotection of the lysine side-chains was achieved by removal of the Mmt protecting groups with four successive 15-minute washes of AcOH/TFE/DCM (1:2:7), washing until the yellow color of released trityl cation was no longer observed. After washing, a reaction mixture was added containing 12 equivalents ethyl acetimidate-HCl and 24 equivalents DiEA in DCM, and the mixture was shaken for 3 hours. The reaction was then drained, a second reaction mixture added, shaken for 2 hours, followed by a third fresh reaction mixture for 1-2 hours. This sequence was done to ensure maximum conversion of the lysine side-chains to L-NIL functional groups.

Cleavage of all peptides was then achieved by shaking for 3 hours with TFA and protecting scavengers, in a 2:1:1:18 ratio of Milli-Q (MQ) $H_2O$: tri-isopropylsilane (TIPS): anisole: TFA. Rotary evaporation was used to remove excess TFA, and trituration with cold diethyl ether yielded crude peptide that was purified by dialysis against Milli-Q water using 100-500 Da MWCO dialysis tubing (Spectra/Por, Spectrum Laboratories Inc., Rancho Dominguez, CA). Purified peptide solutions were adjusted to pH 7.2-7.4, after which they were sterile filtered using 0.2 m filters and lyophilized to powder for storage and use in experiments. All peptides were analyzed by Autoflex MALDI-TOF MS (Bruker Instruments, Billerica, MA) for confirmation of expected peptide mass and purity.

Hydrogel preparation and loading. All chemicals not otherwise specified were purchased from Sigma-Aldrich (Sigma-Aldrich, St. Louis, MO). For preparation of all sterile K2-MDP, L-NIL-MDP, E2-MDP, and R2-MDP hydrogels, 2 wt. % (20 mg/mL) peptide solutions were made by dissolving lyophilized peptide mass in sterile 298 mM sucrose.

Sterile 1× Hank's Balanced Salt Solution (HBSS, Fisher Scientific, Hampton, NH) was used to initiate gelation in cationic MDPs (K2-MDP, L-NIL-MDP, and R2-MDP), while a separate solution of 45 mM $Mg(Cl)_2$ in 1× HBSS was used with the anionic E2-MDP, calculated to achieve 22.5 mM (4 mol eq.) $Mg^{2+}$ upon final dilution with peptide. To form all hydrogels, 2 wt. % peptide solutions were diluted 1:1 with 1× HBSS, or 1× HBSS+45 mM $Mg^{2+}$ depending on peptide gelation requirements, for final formulations containing 1 wt. % peptide (10 mg/mL, approximately 5-6 mM), 0.5× HBSS, and 149 mM sucrose.

Circular dichroism (CD). Peptide samples were prepared at 0.1 wt. % in MQ $H_2O$ (diluted from 1 wt. % hydrogels in HBSS and sucrose) for CD analysis on a Jasco J-810 spectropolarimeter (Jasco Inc., Easton, MD). Scanning experiments were performed from 250-180 nm with a 0.1 nm pitch, using an accumulation of 5-10 scans to acquire averaged spectra with reduced noise. The 0.1 wt. % peptide solutions were loaded into 0.1 mm or 0.01 mm glass cuvettes. Diagnostic peaks for β-sheet secondary structure identification were as follows: minimum near 216±2 nm and maxima near 196±2 nm.

Attenuated total reflectance Fourier transform infrared spectroscopy (ATR FT-IR). Peptide samples (10 μL of 1 wt. % peptide solution) were dried under nitrogen on a Golden Gate diamond window of an ATR stage for 4-24 hours as necessary to remove water. IR spectra were then collected on a Jasco FT/IR-660 plus spectrometer (Jasco Inc., Easton, MD) at 1 $cm^{-1}$ resolution with 64 scans accumulation, and the background was collected and subtracted to minimize the contribution of water in the resulting spectra. Relevant peaks in the 1750-1450 $cm^{-1}$ range were plotted and analyzed to determine the secondary structure of the peptides.

Oscillatory rheology. Peptide hydrogels were analyzed for their mechanical properties by oscillatory rheology using a TA Instruments AR-G2 rheometer (TA Instruments, New Castle, DE). Samples of 150 μL of 1 wt. % MDP hydrogels were prepared 24 hours prior to use for rheology, to allow full equilibration of the material. Gel samples were then transferred from a cut syringe onto the rheometer stage equipped with a 12 mm stainless-steel parallel plate set to a 1000 m gap height. The following program was used to monitor the storage modulus (G') and loss modulus (G") under various conditions as has been previously published (Li & Hartgerink, 2017). Strain sweep analysis was performed using an applied strain of 0.01-200% at a frequency of 1 rad/s. Frequency sweep analysis was performed under 1% strain at 0.1-100 rad/s. Shear recovery analysis was performed by subjecting the peptide sample to 1% strain for 20 min, then 200% for 1 min, and finally 1% for 20 min, allowing for disruption of the hydrogel and monitoring of G' and G" recovery.

Transmission electron microscopy (TEM). Peptide nanostructure was studied by transmission electron microscopy (TEM). For TEM, all samples were prepared via negative staining on Quantifoil R1.2/1.3 holey carbon films on copper mesh grids. Peptide samples were prepared at concentrations ranging from 0.1 wt. %-0.01 wt. %, and 10 μL from each solution were spotted onto individual grids. Excess peptide solution was blotted after being allowed to adsorb for 1 min. The sample grids were negative stained for 5 min using a 2 wt. % phosphotungstic acid (PTA) solution in MQ $H_2O$ prepared at pH 7 and sterile filtered. Excess PTA solution was wicked off the grids before drying overnight. Prepared samples were imaged at 120 kV and 40,000× magnification using a JEOL 2010 TEM microscope (JEOL USA Inc., Peabody, MA).

Cell culture. For in vitro experiments, mouse RAW 264.7 cells (ATCC TIB-71) were grown in DMEM media supplemented with 10% Heat-Inactivated Fetal Bovine Serum (HI-FBS), L-glutamine, sodium pyruvate, and 1% penicillin-streptomycin. Cells were cultured at 37° C. with 5% $CO_2$ and subcultured using scraping.

For 2-D culture live-dead viability studies, peptide hydrogels were pipetted into 0.4 $cm^2$ wells of Lab-Tek 16 well glass chamber slides (Thermo Fischer, Rochester, NY). Gels were pipetted to produce 70 μL pucks with a thickness of 1.75 mm. The gels were carefully pipetted into the bottom of each well and tapped before shear recovery to create flat gel profiles. After pipetting, the samples were allowed to shear recover for 5-10 min before adding 200 μL cell media and 10,000 RAW 264.7 cells. For each experiment time point (days 1 and 3) separate slides with duplicate gels were created. The cell media was changed every 2 days, taking care to not disturb or dislodge the gel material.

At each desired time point the following procedure was used to stain the cells for live-dead analysis. Live-dead staining solution was prepared in DPBS (Thermo Fisher Scientific, Rockford, IL) with 2 μM Calcein AM (Life Technologies), 4 μM Ethidium homodimer (Life Technologies), and 5 μg/mL Hoechst 33342 (BD Biosciences, San Jose, CA). Cell media was removed from the top of the hydrogel samples, which were then washed with PBS. Samples were then stained with 100 μL of prepared solution by incubating at 37° C. with 5% $CO_2$ for 60 min while protected from light. After staining, the gels were removed from the glass chamber slides and placed in PBS before immediately imaging by confocal. Gels were analyzed by z-stack imaging using a Nikon A1 Confocal Microscope with a 40× water objective (405 nm blue channel laser, 488 nm green channel laser, 561 nm red channel laser). Image processing was done using NIS Elements, and Imaris Cell Counting software was used to quantify live-dead percentages.

iNOS knockdown in vitro Greiss assay. To evaluate the iNOS knockdown efficacy of various materials, the following procedure was used to test % iNOS inhibition of RAW 264.7 cells stimulated with Lipopolysaccharide (LPS, Thermo Fisher Scientific, Rockford, IL) and recombinant mouse IFN-7 (Biolegend, San Diego, CA). RAW macrophages were prepared at a stock concentration of $2.5×10^6$ cells/mL, and plated at $2.5×10^5$ cells per well in 24-well plates. For samples testing the efficacy of 2-D surface cell culture, 200 μL of MDP hydrogels was applied to evenly coat the surface of each well before addition of cells. Each experimental condition was performed in triplicate. The following controls were included in every experiment, 1) media alone, 2) stimulated cells alone, and 3) unstimulated cells alone. To each well, stimulation media or normal media was then added based on experimental requirement. Stimulation media was prepared with LPS (final concentration 1 μg/mL) and IFN-γ (final concentration 100 U/mL). For samples testing material efficacy in solution (e.g. free L-NIL), after 6 hrs of incubation at 37° C. with 5% $CO_2$ the desired concentration of inhibitor was added to achieve a range of concentrations between 1 μM and 1 mM.

In all cases after 24 hours from time of stimulation, samples of cell media were collected from each well after mixing media by pipetting before collection. Media samples were placed into a 96-well plate and centrifuged at 5000 rpm for 10 min. Supernatants were removed and placed in a new clear 96-well plate, and samples were immediately analyzed using a colorimetric Greiss Assay (Cayman Chemical, Ann Arbor, MI) to assess nitrite levels (Bryan & Grisham, 2007). Color was allowed to develop for 10 min following addition of Greiss reagents, and absorbance was read at 540 nm on a plate reader. Percent iNOS inhibition for each sample was calculated by first subtracting the absorbance of the media-only baseline, and then converting to a percent of maximum nitrite signal as determined by the internal standard of stimulated cells alone.

Subcutaneous experiments and histology. C57BL/6J female mice were purchased from The Jackson Laboratory at age 8-12 weeks for subcutaneous characterization experiments. Mice were housed under specific pathogen-free conditions in standard temperature and lighting conditions with free access to food and water, and experiments were conducted with approval of the Institutional Animal Care and Use Committee (IACUC) at Rice University and according to NIH guidelines. Mice were injected with 100 μL MDP hydrogels in each of four separate sites in the subcutaneous space of the dorsal flank after the skin was shaved and sterilized with alcohol. At days 3, 7, 14, and 21 the mice were euthanized and the dorsal skin around the entire implant was removed, fixed overnight in 10% neutral buffered formalin, processed and paraffin embedded, and finally sectioned at 5 m thickness for staining using standard Masson's trichrome or hematoxylin and eosin (H&E) procedures, as well as immunohistochemical analyses (e.g., anti-nitrotyrosine IHC, or α-SMA blood vessel analysis).

Evaluation of in vivo VEGF reduction using murine B16-F0 melanoma tumor model. C57BL/6J male mice were purchased from The Jackson Laboratory. Tumor inoculation was performed when mice reached 10-14 weeks of age. All experiments were performed with approval of IACUC at Baylor College of Medicine (BCM) and followed established protocols. B16-F0 melanoma cell line was purchased from American Type Culture Collection (ATCC) and maintained according to manufacturer instructions (DMEM high-glucose with 10% fetal bovine serum and 1% penicillin/streptomycin). C57BL/6J mice were injected subcutaneously (s.c.) with $3\times10^5$ B16-F0 cells in a single flank. Once tumors became palpable (day 7 post-inoculation) mice were injected intratumorally (i.t.) with either vehicle buffer control Hank's Balanced Salt Solution (HBSS), free L-NIL dissolved in HBSS at 20 mM, K2-MDP hydrogel at 1 wt. % (5.6 mM peptide), or L-NIL-MDP hydrogel at 1 wt. % (5.2 mM peptide, or approximately 20 mM L-NIL functional groups). All injections were done using 100 μL total injection volume.

Mice were euthanized 5 days following i.t. injections and tumor/blood were collected. Blood was allowed to clot prior to centrifugation (2000×g, 10 mins, room temperature) and serum was collected from the supernatant and stored at −80° C. prior to analysis. VEGF quantification of undiluted serum was performed using a mouse VEGF Quantikine ELISA kit (R&D Systems, Minneapolis, MN) following manufacturer's instructions. All individual mouse samples were run in triplicate and averaged for the final reported value per mouse. Statistical differences were evaluated using Tukey's multiple comparisons test. B16-F0 tumors were also harvested and immediately fixed overnight in 10% neutral buffered formalin, embedded in paraffin, and sectioned at 5 m thickness for histological analysis.

Example 2—Material Synthesis and Chemical Characterization

To synthesize a bioactive L-NIL-mimicking peptide nanofiber (or L-NIL-MDP), a modified solid-phase peptide synthesis method, depicted in FIGS. 2A-C, was used to maximize the chance for successful conversion of the large number of lysine side-chains of the parent peptide. Since the parent K2-MDP is designed to aggregate and self-assemble into higher-ordered structures and nanofibers, the conversion reaction to the L-NIL-MDP would have been difficult to perform in solution, due to concentration limitations and the likelihood for some of the key side-chain amines to be buried and relatively inaccessible. A reaction on solid-phase resin was therefore performed, and low-loading MBHA resin was used to maximize inter-peptide strand spacing and achieve theoretical 'infinite dilution' to facilitate side-chain accessibility and a higher conversion ratio. The synthetic scheme (FIGS. 2A-C) incorporates the use of a highly acid-labile monomethoxytrityl (Mmt) protecting group on the terminal lysine residues (FIG. 2A), allowing for the on-resin deprotection of the lysine side-chains prior to conversion. Thus, after first synthesizing $K^{Mmt}_2(SL)_6K^{Mmt}_2$ (SEQ ID NO: 3) on solid phase and acetylating the N-terminus, the lysine side-chains were deprotected using 10% acetic acid (FIG. 2B) and synthetically converted to the L-NIL moiety using an acetimidation reaction of the nucleophilic amines (FIG. 2C), modified from literature procedures (Moore et al., 1994).

After this on-resin conversion process, the modified peptide was cleaved from the solid-phase and recovered in solution, with MALDI-MS analysis showing successful conversion of the peptide to the primarily fully-modified species (FIG. 3A). Critical to the final design is that the L-NIL-MDP retains the cationic properties of the original lysine-based MDP, with the converted L-NIL acetamidine moieties bearing positive charges at physiological pH akin to canonical lysine or arginine amino acid side-chains. This maintains the ability to control MDP self-assembly and hydrogel formation by charge repulsion and ionic crosslinking.

Similar to previously designed cationic MDPs, hydrogelation of the L-NIL-MDP is controlled by the addition of multivalent negative ions (e.g., phosphate anions in PBS or HBSS buffers) or pH variation. In characterizing the material, its self-assembly, secondary structure, nanostructure, and viscoelastic properties were compared to the parent material K2-MDP, with the hypothesis that the process of chemical conversion to L-NIL-MDP should not significantly affect the final peptide material's physical properties (FIGS. 3A-F). The L-NIL-MDP was shown to possess a β-sheet secondary structure, as confirmed by minima near 216±2 nm and maxima near 196±2 nm in the circular dichroism (CD) spectra for both K2-MDP and L-NIL-MDP (FIG. 3C). Furthermore, infrared spectroscopy (ATR-FT-IR) confirmed the secondary structure to be an anti-parallel β-sheet, with characteristic amide I absorbances observed at 1695-1696 $cm^{-1}$ and 1618-1620 $cm^{-1}$ for both parent and converted peptide (FIG. 3D). Transmission electron microscopy (TEM) analysis of the self-assembled nanostructure showed the formation of highly similar nanofibers for both MDPs, with the L-NIL-MDP nanofibers potentially showing slightly reduced persistence length (FIGS. 3E-F). Finally, when prepared at 1 wt. % (5.2 mM) in an aqueous buffer containing sucrose for cell compatibility and phosphate anions for crosslinking (HBSS), the L-NIL-MDP forms a compliant hydrogel with a storage modulus (G') of approximately 260-300 Pa, a loss modulus (G") of approximately 20-25 Pa, and a shear recovery of ~86% of its initial storage modulus 1 minute after a high strain event such as injection through a needle (FIG. 3B). For comparison, the parent K2-MDP hydrogel has been reported to have a G' in the range of approximately 200-500 Pa with a shear recovery of ~82% after 1 minute (Aulisa et al., 2009). These results demonstrate that the converted material has retained thixotropic mechanical properties ideal for hydrogel syringe injectability, and overall material characterization confirmed that the L-NIL-MDP retains the same secondary structure, nanostructure, and bulk material properties as the parent K2-MDP. Therefore, any resulting biological effects of the chemically modified peptide cannot be ascribed to differences in supramolecular or material properties, but rather must be due to the new chemical functionality and bioactivity provided by the acetamidine conversion.

Example 3—Evaluation of Material Bioactivity In Vitro

As an essential step in the development of any new biomaterial, the L-NIL-MDP hydrogel was evaluated in various biological assays to determine how it interacts with living systems. First, the material's biocompatibility in vitro was compared to other MDP hydrogels (e.g., $K_2(SL)_6K_2$ (SEQ ID NO: 2), $R_2(SL)_6R_2$ (SEQ ID NO: 6), or $E_2(SL)_6E_2$ (SEQ ID NO: 5) MDPs) (Aulisa et al., 2009). RAW 264.7 macrophages were utilized in all in vitro studies as NO is a key macrophage product for various cellular functions and activities, and RAW 264.7 is a murine cell line widely used in iNOS-related experiments in the literature (Nathan & Hibbs, 1991; MacMicking et al., 1997; Aldridge et al., 2008). Live-dead analysis of RAW macrophages cultured for one to three days on 1 wt. % hydrogel surfaces showed that the L-NIL-MDP was compatible for cell growth (approx. 95% cell survival after three days), facilitating the attachment and proliferation of macrophages on the hydrogel comparable to K2-MDP, R2-MDP, and E2-MDP (FIG. 4). It was noted that the highest degrees of cell attachment and proliferation were observed for the cationic MDPs (L-NIL-MDP, K2-MDP, and R2-MDP), while the anionic E2-MDP showed poorer cell survival and proliferation rates likely due to inhibition of cell attachment by the negative carboxylic acid functional groups displayed by the material. This is consistent with various other studies that have demonstrated the ability of cationic moieties or materials (such as poly-lysine) to facilitate cell attachment, while negative materials often do not (Schneider et al., 2004; Kim et al., 2011; Lam et al., 2014).

Figure 5:
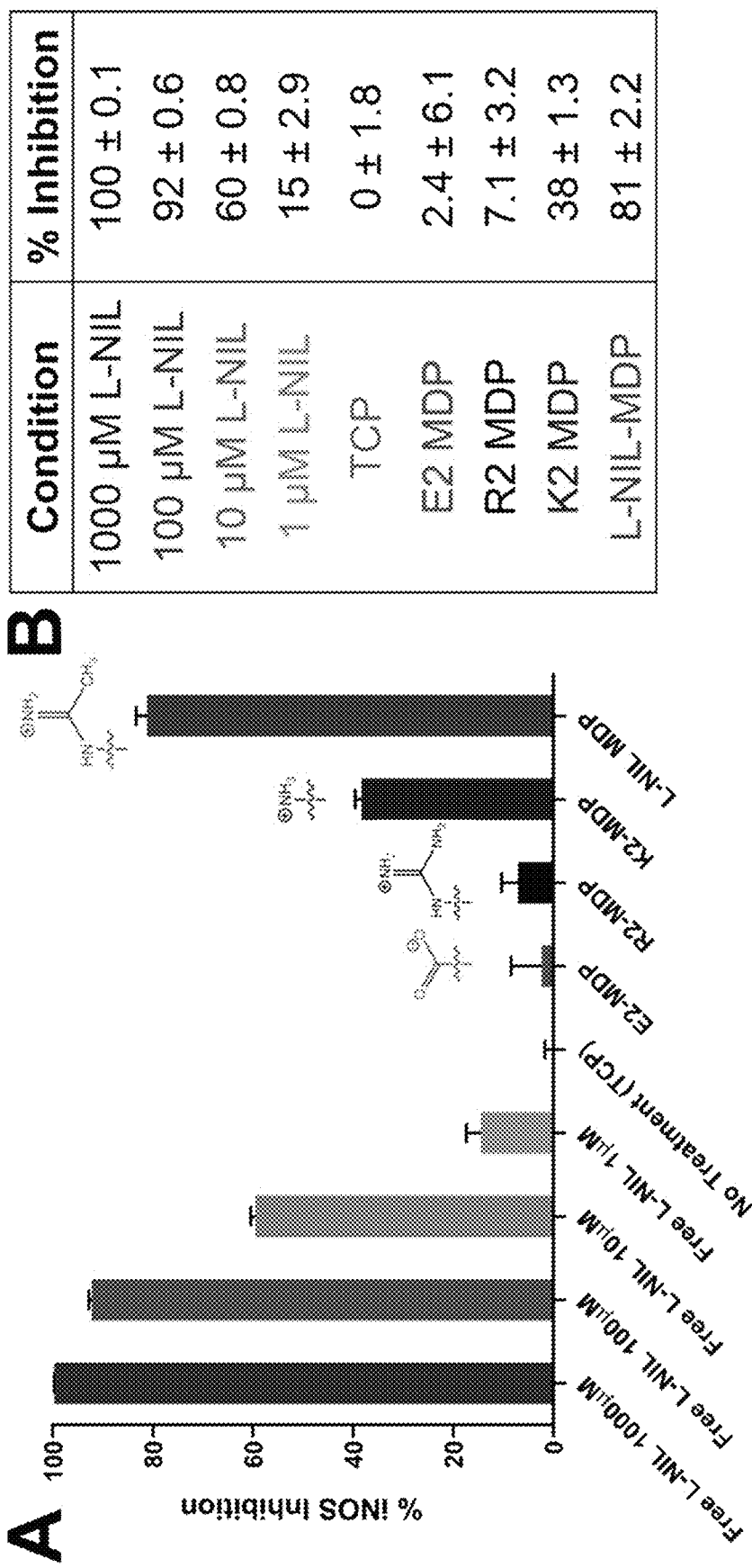
FIGS. 5A-B. Greiss assay results used to evaluate iNOS knockdown efficacy of various materials.

Evaluating bioactivity is critical to studying any system that has changed the structure or availability of a drug. The conversion of a small-molecule drug to a chemical motif displayed on a larger scaffold in no way guarantees superior drug persistence (or even any drug activity at all), as changing the size or chemical structure of a molecule can fundamentally change how it interacts with its biological environment. To begin evaluating the pharmacological activity of the L-NIL-MDP, an in vitro iNOS knockdown assay was performed to compare the efficacy of different MDP hydrogels to free L-NIL drug in solution as a positive control. RAW 264.7 macrophages were cultured on various material surfaces, comparing the effects of different MDP hydrogels to tissue culture plastic alone (or TCP) or free L-NIL in solution in 24-well plates. All cells were stimulated with LPS and IFN-7 to upregulate iNOS activity and promote the release of detectable iNOS products into the media (i.e., nitrites), and media was removed 24 hours from the start of the experiment and assessed using a colorimetric Griess assay to determine the extent of relative iNOS inhibition by each material. The L-NIL-MDP was shown to be the most effective surface-culture material tested compared to TCP, K2-MDP, R2-MDP, and E2-MDP, exhibiting over 80% iNOS inhibition of RAW macrophages cultured on the hydrogel (FIGS. 5A-B). This is comparable to the level of inhibition achieved when using 100 μM of free L-NIL in solution (FIG. 5B). However, it must be stated that in this static in vitro system which tests only the first 24 hours of activity, fluid flow and free diffusion into larger environments that are present in vivo are not occurring, and therefore the true advantages of an implantable and durable hydrogel (compared to a freely diffusible small-molecule) are not fully realized.

In comparing the activity of the L-NIL-MDP to other MDP hydrogels tested, it is interesting to note that the parent K2-MDP displays some inherent level of iNOS inhibition comparable to <10 μM free L-NIL (FIG. 5B). This is likely because L-NIL (N6-[1-iminoethyl]-L-lysine) is chemically derived from lysine based on the original literature synthesis (Moore et al., 1994), and therefore the lysine-rich K2-MDP was observed to display basal levels of activity due to its close chemical relation to L-NIL, though this activity is nearly 10-fold less than the L-NIL-MDP in terms of comparison to free L-NIL concentration. This only further reinforces the strengths of displaying the L-NIL drug moiety on a lysine-based peptide scaffold, suggesting that even the few unreacted lysine residues within the L-NIL-MDP material (FIG. 3A) can still display basal iNOS inhibitory activity. For the R2-MDP, simple structural comparison would suggest that the arginine guanidinium side-chain would show relatively similar iNOS inhibition to L-NIL or the L-NIL-MDP, due to its similarity to the drug's acetamidine moiety. Yet in contrast to the L-NIL-MDP or even the K2-MDP, the R2-MDP showed little to no iNOS inhibition. This can be attributed to the fact that arginine is the natural substrate for iNOS in the synthesis of nitric oxide (NO), and therefore in this system it likely acts as an agonist to the enzyme (Tang et al., 2015). Finally, the glutamic-acid based E2-MDP similarly shows little to no iNOS inhibition likely due to complete structural mismatch. Most importantly, this assay was the first to demonstrate that the L-NIL-MDP does not eliminate the bioactivity of L-NIL, but rather it displays a potent ability to inhibit iNOS activity in cell populations that interact with the hydrogel material.

Example 4—Histological Material Evaluation and Immune Response Profiling

Evaluation of material biocompatibility, degradation, and immune response profile in vivo was performed by histological analysis of hydrogel implants injected subcutaneously in healthy mice. L-NIL-MDP hydrogel implants were injected as 100 μL boluses underneath the skin and extracted 3, 7, 14, and 21 days later to study material persistence and degradation, as well as the host immune response (FIGS.

6A-L). At the day 3 timepoint (FIGS. 6A-C) a high density of cellular infiltration, mostly in the periphery of the hydrogel implant, was observed by cells that morphologically resemble innate immune cell populations, such as monocytes, macrophages, and granulocytic cells. This represents an initial acute inflammatory reaction by the host to the foreign material that is consistent with previous immune cell profiling of other subcutaneously injected MDP hydrogels by flow cytometry (Lopez-Silva et al., 2020). However, over the course of 7-21 days this initially large and uneven cellular infiltrate resolves into a homogenous cell infiltrate that is observed deeper into the core of the hydrogel (FIGS. 6D-L), as indicated by the fact that the local density of cell nuclei per $mm^2$ within the hydrogel bolus is observed to decrease over three weeks of implantation as the inflammatory reaction resolves. This demonstrates that the material does not cause a chronic inflammatory reaction after injection but is biocompatible and facilitates cellular infiltration and remodeling of the hydrogel implant over 1 to 3 weeks.

Figure 6:
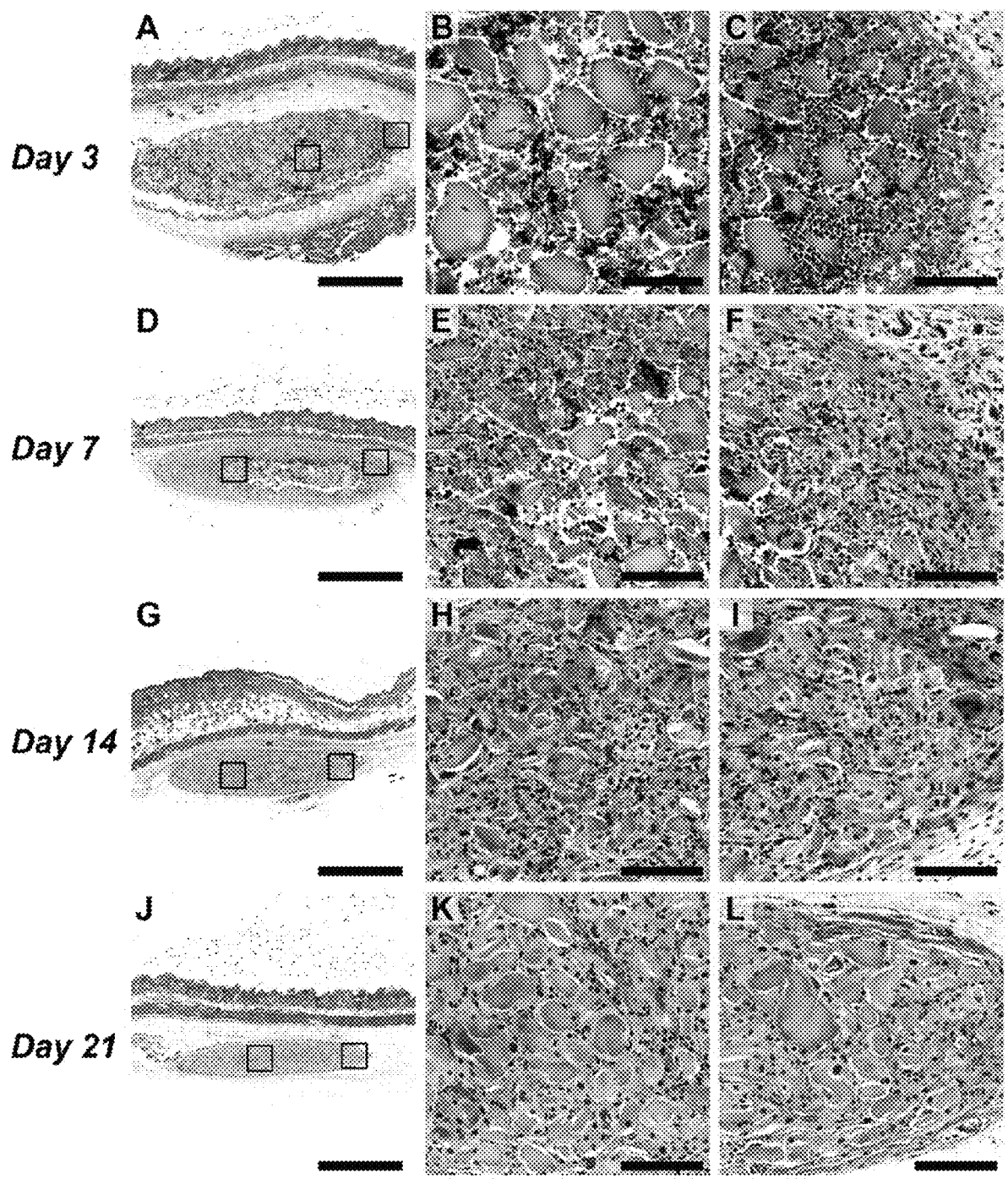
FIGS. 6A-L. Histological analysis of L-NIL-MDP hydrogel implants extracted 3-21 days post subcutaneous injection in mice (Masson's trichrome stained).

In general, the hydrogel bolus is also observed to steadily decrease in overall size with each passing week (FIGS. 6A-J), marking the natural biodegradation and remodeling of the material that can also be observed by increasing local collagen deposition (shown in blue) within and around the implant. These histology data show a degradation profile that is slower than other classes of MDPs studied in prior investigations, such as fast-degrading anionic or neutral MDPs (Lopez-Silva et al., 2020), as the L-NIL-MDP hydrogel implants are still observable even 3 weeks post injection. In the case of the L-NIL-MDP, which was created specifically for extended immunotherapy availability and release, this slow degradation and remodeling rate is ideal, for the hydrogel can persist in its injected location for over three weeks and continue to perform its pharmacologic function. This hypothesis is supported by the observation that at every timepoint, including the longest timepoint studied (day 21), large islets of what appear to be pristine, non-infiltrated L-NIL-MDP hydrogel are still present and have not yet been degraded by interacting cells (FIGS. 6J-L). Overall, these results show that the degradation process occurs over a 3-4 week period, ideal for creating a long-term therapeutic effect.

Immunohistochemistry staining was performed on hydrogel implant tissue sections to further study in vivo properties of the L-NIL-MDP compared to related cationic MDPs. Anti-nitrotyrosine immunostaining was used to assess relative levels of nitrosylation of tyrosine within and around the subcutaneously injected hydrogel implants as a marker of iNOS inhibition (FIGS. 7A-H). It is known that the formation of nitric oxide (NO) and other nitrogen oxides in vivo can lead to observable post-translation modifications of peptides and proteins (Ischiropoulos, 2003). For example, surface-exposed 3-nitrotyrosine can be used as a marker of cell or tissue inflammation and damage by reactive nitrogen and oxygen species such as NO (Ahsan, 2013). The higher the local levels of iNOS activity, the greater should be the density of nitrosylated tyrosine. Therefore, visualization of nitrotyrosine levels by targeted antibodies can serve as a general indication of in vivo iNOS activity, or in the case of the L-NIL-MDP, local iNOS inhibition.

Figure 7:
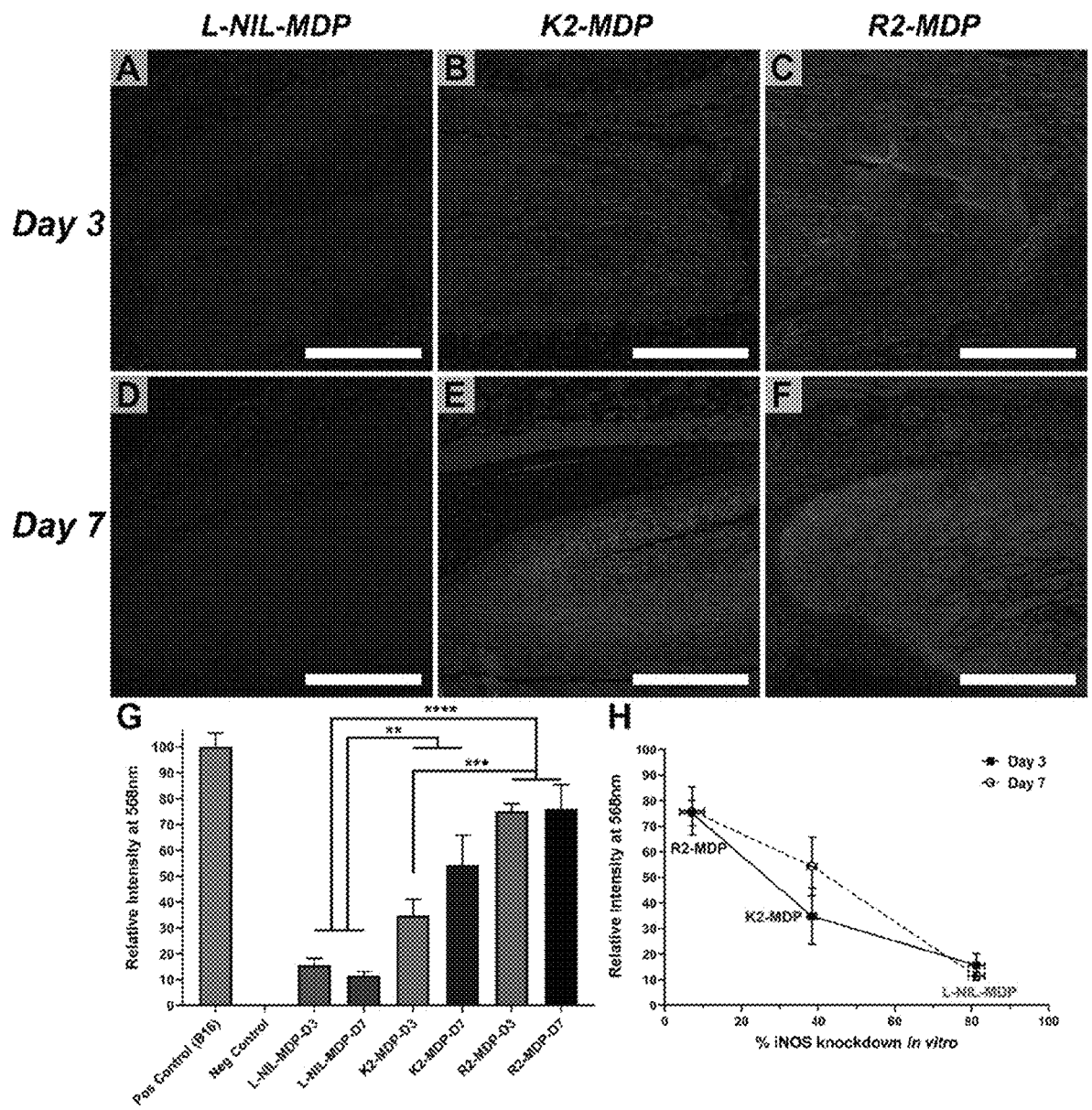
FIGS. 7A-H. Anti-nitrotyrosine immunostaining of subcutaneously injected MDP hydrogels to evaluate effects of relative inhibition of iNOS in vivo, using red 568 nm secondary antibody reactive to anti-nitrotyrosine primary and DAPI for nuclei counterstain.

As shown in FIGS. 7A-H, nitrotyrosine staining intensity shown in red was significantly lower in the L-NIL-MDP hydrogel implants compared to other cationic MDPs such as K2-MDP and R2-MDP. This result was striking as all three cationic hydrogel materials have been shown to result in high levels of cellular infiltration indicative of similar initial immune reactions by histology (Lopez-Silva et al., 2020). Therefore, the nitrotyrosine intensity differences observed here cannot be attributed to differences in cellular density. This result is most dramatic in the day 7 post-injection images shown in FIGS. 7D-F, as nitrosylation of tyrosine residues is a cumulative phenomenon that is known to increase with time of exposure to nitrosylating species. Therefore, it is even more striking that the L-NIL-MDP maintains low nitrotyrosine levels in and around the implant for an extended period of time, even into the skin and muscle layer above the hydrogel bolus (FIGS. 7A,D). This suggests durable iNOS inhibition from a single subcutaneous injection, significantly reducing reactive nitrogen species in the surrounding environment and protecting labile species such as tyrosine from nitrosylation over time. Isotype control tests using rabbit IgG in place of rabbit anti-nitrotyrosine primary showed little to no non-specific staining of anti-rabbit 568 nm secondary antibody, validating the significant staining intensity differences observed between materials.

Furthermore, staining intensity increased in inverse correlation to previously evaluated iNOS inhibition efficacy in vitro for each material (FIGS. 7G-H), showing excellent agreement between two separate studies. The R2-MDP showed the lowest iNOS inhibition in vitro (FIGS. 5A-B) and conversely the highest nitrotyrosine staining in vivo (FIGS. 7A-H), the K2-MDP showed both moderate iNOS inhibition and nitrotyrosine intensity, and finally the L-NIL-MDP showed both the greatest degree of iNOS inhibition among the tested cationic hydrogels, as well as the lowest degree of nitrotyrosine staining in vivo. These highly correlating results demonstrate that the L-NIL-MDP hydrogel displays the desired pharmacological activity in various biological systems, validating the system design and experimental hypothesis.

Figure 8:
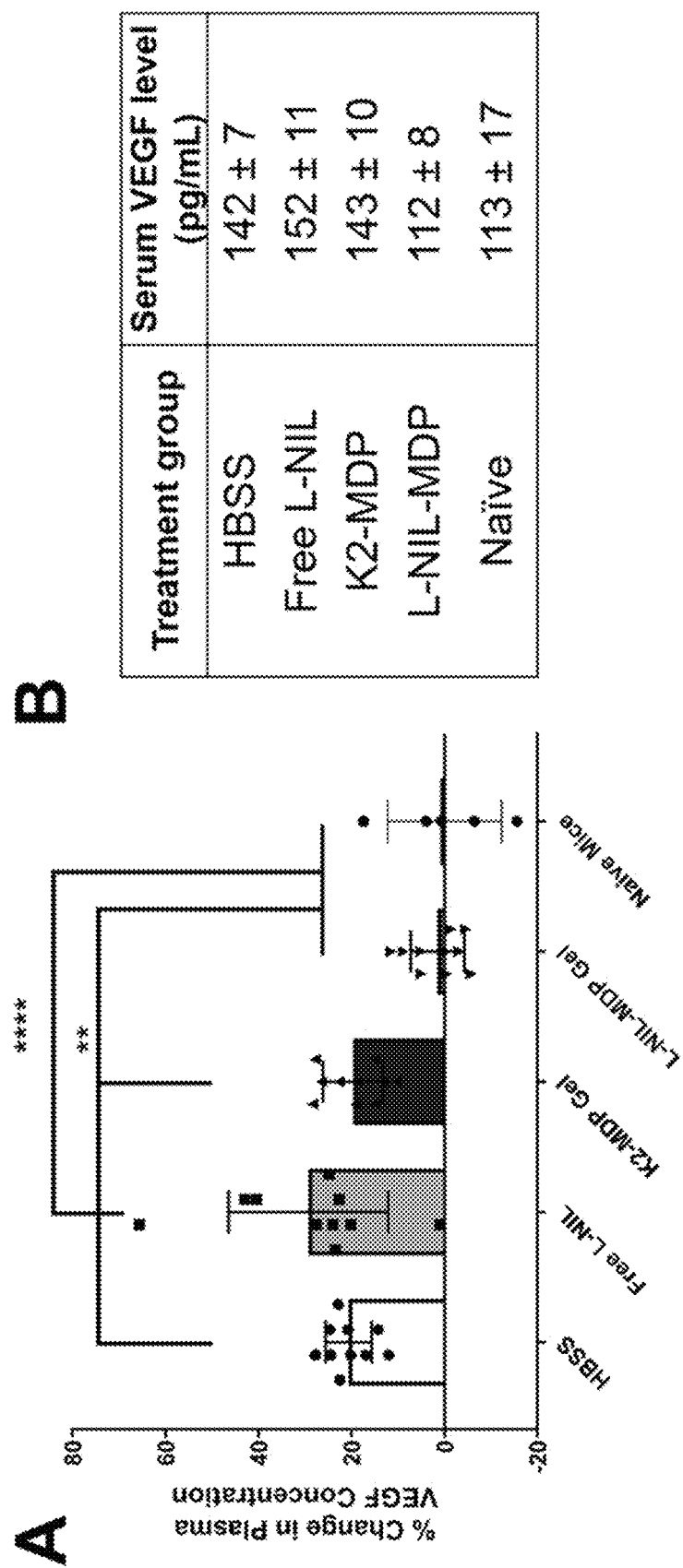
FIGS. 8A-B. Vascular endothelial growth factor (VEGF) serum levels in mice bearing B16-F0 melanoma tumors.

Example 5—Extended In Vivo Systemic Effects of L-NIL-MDP in a Melanoma Murine Model As has been stated before, the goal of this work was to generate an inherently immunotherapeutic biomaterial that could induce a durable and extended biological response. The hypothesis proposed that a design-compatible drug moiety could be used within a peptide hydrogel to improve treatment duration and efficacy compared to the original small-molecule. Therefore, validation of this new biomaterial was sought in a relevant disease model by performing intratumoral injections in mice bearing established B16-F0 melanoma tumors to evaluate material efficacy in reducing systemic VEGF levels compared to free L-NIL drug injections. Aberrant iNOS activity and NO production observed in various cancer models have been shown to increase VEGF secretion and tumor vascularization, such that inhibition or genetic knockdown of iNOS can decrease VEGF levels, ultimately leading to reduced tumor angiogenesis and slowed tumor growth (Jenkins et al., 1995; Ambs et al., 1998; Yamaguchi et al., 2002). ELISA quantification of undiluted serum from mice injected intratumorally with either HBSS buffer control, K2-MDP hydrogel, L-NIL-MDP hydrogel, or free L-NIL drug (at an equimolar concentration to total L-NIL drug moieties in the 1 wt. % L-NIL-MDP hydrogel) showed that only the L-NIL-MDP significantly reduced systemic VEGF levels (FIGS. 8A-B). Not only did the L-NIL-MDP hydrogel show significantly reduced circulating VEGF levels compared to free L-NIL or K2-MDP, but this effect was observed 5 days after injection of materials, demonstrating the prolonged nature of the systemic response that is not observed when an equimolar dose of free L-NIL drug is administered. Furthermore, while VEGF levels in tumor bearing mice were typically elevated 20% above naive levels (at approximately 140-150 pg/mL, FIG. 8B), VEGF levels in the L-NIL-MDP treatment group were reduced back to basal levels observed in naive mice (around 110 μg/mL). This shows a potent effect not achieved with free L-NIL drug, and further establishes that the L-NIL-MDP does not overly inhibit the iNOS-VEGF pathway to levels that could be deleteriously low. These results demonstrate that the L-NIL-MDP material allows for a uniquely durable and controlled therapeutic response that can affect tumor biology in vivo. Significantly, this systemic affect was observed with only a single injection of hydrogel material compared to the typical need for repeated administration of free L-NIL in other studies (Hanoteau et al., 2019).

Figure 9:
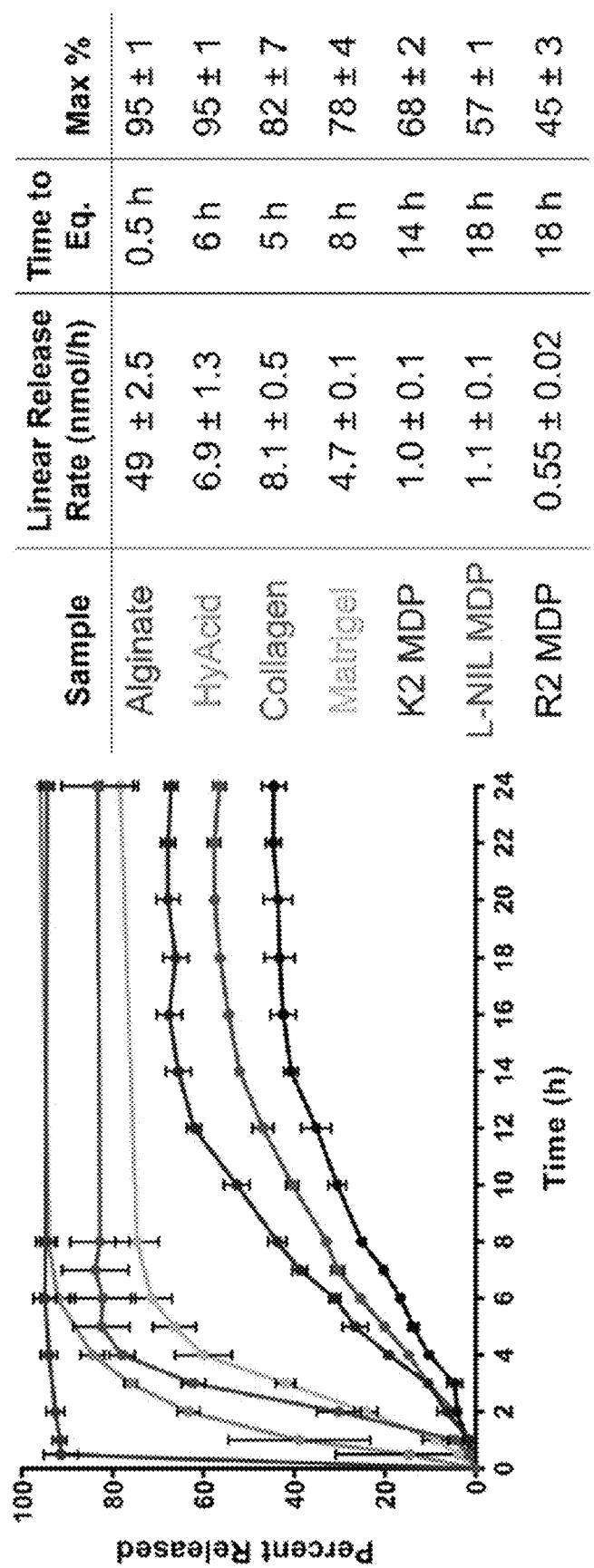
FIG. 9. Drug release kinetics data comparing the ability of the L-NIL-MDP hydrogel to load and control the release of STING agonist ML RR-S2 CDA (CDN) to the rates of other materials. Plot of percent of CDN released over time is shown in the left panel. Quantification of the linear release rate (nmol/h), time to equilibrium, and minimum percent are shown in the right panel.
Figure 10:
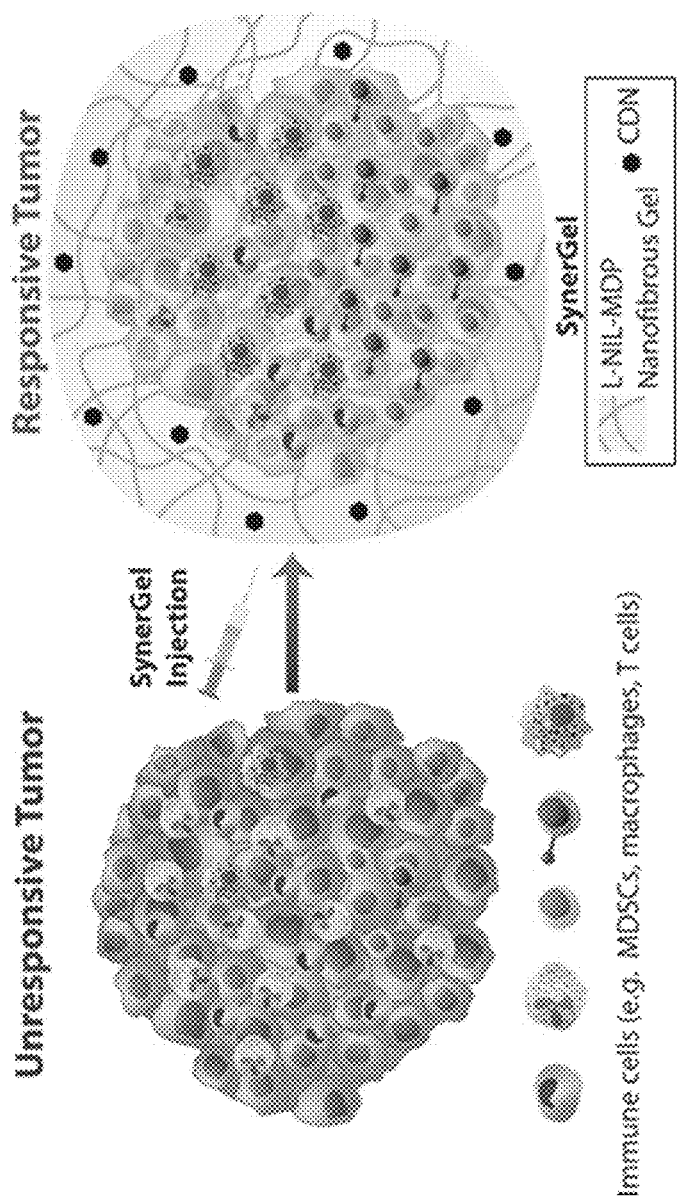
FIG. 10. Graphical representation of biomaterial-facilitated immunotherapy. The biomaterial delivery vehicle combines inherent iNOS inhibition with controlled delivery of a STING agonist, allowing for immune-mediated elimination of established treatment-resistant tumors.

While there was no favorable effect on tumor growth reduction observed in this focused monotherapy experiment, this was expected as iNOS inhibition via L-NIL has not demonstrated significant treatment efficacy as a monotherapy in more established tumor models (Hanoteau et al., 2019; Jayaraman et al., 2014). However, it was imperative to establish the L-NIL-MDP biomaterial's independent activity and function as a newly designed and synthesized therapeutic agent. The inherent bioactive properties of the L-NIL-MDP hydrogel can be used as a delivery vehicle in combination therapy approaches for intratumoral treatments, combining durable iNOS inhibition from the MDP hydrogel with other immunotherapy or chemoradiotherapy regimens that are typically used in conjunction with L-NIL (Hanoteau et al., 2019). For example, L-NIL-MDP achieves comparable or even better controlled release of the STING agonist ML RR-S2 CDA (CDN) than K2 MDP (a.k.a. STINGel) (FIG. 9).

Example 6—Materials and Methods for Examples 7-9

Peptide synthesis. All MDPs used in this study were synthesized by solid phase peptide synthesis with amidated C-termini and acetylated N-termini. The L-NIL-MDP was synthesized by on-resin side chain deprotection of acid-labile monomethoxytrityl (Mmt) protecting groups, followed by conversion of free lysine side chains to the L-NIL acetamidine functional group by reaction with excess ethyl acetimidate-HCl and DIEA as described previously (Leach et al., 2019). However, in previously reported syntheses, deprotection of the Mmt groups was performed using 10% acetic acid in TFE/DCM, but in this study, use of 1% TFA in DCM provided superior deprotection speed and higher percent conversion and was used throughout. For confirmation of successful synthesis, all peptides were analyzed by matrix-assisted laser desorption/ionization time of flight mass spectrometry (MALDI-TOF MS) using an Autoflex Bruker instrument (FIGS. 15A-D). For more detailed peptide synthesis methods of the multidomain peptides (MDPs) $K_2(SL)_6K_2$ (SEQ ID NO: 2), $O_5(SL)_6O_5$ (SEQ ID NO: 4), $E_2(SL)_6E2$ (SEQ ID NO: 5), and the L-NIL-MDP, please refer to our previous publications (Leach et al., 2019; Lopez-Silva et al., 2019; Lopez-Silva et al., 2020).

Hydrogel preparation and loading. All chemicals not otherwise specified were purchased from Sigma-Aldrich (Sigma-Aldrich, St. Louis, MO). All sterile K2-MDP, L-NIL-MDP, E2-MDP, and 05-MDP hydrogels were prepared first at 2 wt. % (20 mg/mL) stock peptide solutions by adding sterile 298 mM sucrose to lyophilized peptide mass, using vortexing and sonication to aid dissolution. Full dissolution of peptide mass usually occurred over 1-3 hours. Stock cyclic dinucleotide ML RR-S2 CDA (CDN) (MedChem Express, Monmouth Junction, NJ) was initially prepared at 2.67 μg/L in endotoxin-free $H_2O$ or sterile 1× HBSS (3.64 mM, 4-fold higher than the final dose of 0.91 mM, 0.67 ug/uL, with a target dosage of 20 μg CDN in 30 μL of hydrogel). Concentration of CDN stocks was confirmed by UV-Vis. Formulations of collagen hydrogel were prepared according to the provided kit protocol (ECM675, EMD Millipore, Temecula, CA). Hyaluronic acid gel formulations were prepared according to the provide kit protocol (HyStem® Scaffold Kit, HYSC010, Sigma-Aldrich). Sodium alginate (ICN218295, MP Biomedicals, Irvine, CA) hydrogels were prepared by crosslinking 1 wt. % aqueous alginate with 0.1M $CaCl_2$). Matrigel formulations were made using the provided protocol (Corning® Matrigel®, 47743-715, VWR, Radnor, PA). Sterile 1× HBSS (Fisher Scientific, Hampton, NH) was used to form hydrogels for cationic MDPs (K2-MDP, L-NIL-MDP), and another solution of 45 mM $MgCl_2$ in 1× HBSS was used with the anionic E2-MDP. To form all CDN drug-loaded hydrogels, 2 wt. % peptide solutions were diluted 1:1 with 1× HBSS+2× CDN (1.82 mM CDN), or 1× HBSS+45 mM $Mg^{2+}$+2× CDN based on the cationic or anionic nature of the peptide requirements for gelation. Final formulations contained 1 wt. % peptide (10 mg/mL, approximately 5-6 mM), 0.5× HBSS, 1× CDN (0.91 mM) and 149 mM sucrose. The neutral 05-MDP hydrogel was diluted to 1 wt. % with 1× HBSS+2× CDN and hydrogelation was triggered by ultrasonication as described previously (Lopez-Silva et al., 2019). Prepared gel formulations for in vivo experiments were slowly loaded using Monoject 300 μL Insulin syringes (Covidien, Mansfield, MA) to avoid bubble formation (centrifuging down bubbles formed in hydrogels as necessary), and loaded syringes were allowed to equilibrate for ~30 min before injection.

Drug release kinetics. For release kinetics studies of CDN release from various hydrogel formulations, aliquots of CDN-loaded gel (30 μL each) were deposited into 96 well Falcon® flat bottom plates (Becton Dickinson Labware, Franklin Lakes, NJ). 30 μL gel was pipetted to generate a cylindrical puck in each well for each experiment. The pipetted gels were allowed to shear recover for approximately 5-10 min before adding 200 μL of the relevant buffer to the top of the gels (1× HBSS for all MDPs, 1× DPBS for collagen, Matrigel, 1× HBSS with 0.1 M $CaCl_2$) for alginate, etc. according to the gelation requirements of the material). The addition of buffer was defined as t=0 for the beginning of release kinetics experiments. Table 1 summarizes the material conditions and preparation methods used for various comparative CDN delivery kinetics studies.

TABLE 1

Summary of tested hydrogel systems for drug release kinetics studies

| Sample | Material Concentration | CDN Concentration | Gelation Method | Syringe Injectable Gel |
|---|---|---|---|---|
| Alginate | 10 mg/mL | 1× (0.91 mM) | in situ $Ca^{2+}$ ionic crosslinking | No |

TABLE 1-continued

Summary of tested hydrogel systems for drug release kinetics studies

| Sample | Material Concentration | CDN Concentration | Gelation Method | Syringe Injectable Gel |
|---|---|---|---|---|
| HyAcid | 8 mg/mL | 0.8× | Thiol + PEG-DA covalent crosslinking | No |
| Collagen | 4 mg/mL | 1× | Heat induced crosslinking | Gels in situ |
| Matrigel | 10.8 mg/mL | 1× | Heat induced crosslinking | Gels in situ |
| K2 MDP | 10 mg/mL | 1× | $PO_4^{3-}$ ionic charge shielding/crosslinking | Yes |
| L-NIL MDP | 10 mg/mL | 1× | $PO_4^{3-}$ ionic charge shielding/crosslinking | Yes |
| E2 MDP | 10 mg/mL | 1× | $Mg^{2+}$ ionic charge shielding/crosslinking | Yes |

A Nanodrop 2000C Spectrophotometer (Thermo Scientific) was used to measure drug release by UV absorbance at 259 nm for CDN ML RR-S2 CDA, using an extinction coefficient of 24,000 $M^{-1}cm^{-1}$ (259 nm). Absorbance measurements were obtained by removing 1 L from the top of the liquid buffers above the loaded gels, over time measuring the increase in absorbance. Over the course of the first 24 hours, release of CDN was measured usually every 1-2 hours and converted to total percent released, with additional measurements also made every 24 hours for up to a week to establish when equilibrium had been reached.

Oscillatory rheology. The mechanical properties of the studied peptide hydrogels were analyzed by oscillatory rheology, using a TA Instruments AR-G2 rheometer (TA Instruments, New Castle, DE). MDP hydrogel samples 150 µL in volume (at 1 wt. %) were prepared 1 day before rheological testing and allowed to equilibrate in a cut syringe. Hydrogels were then transferred from the syringe to the rheometer stage, and the rheometer was equipped with a 12 mm stainless-steel parallel plate with 1000 m gap height. As published previously, the following program was used to analyze the storage modulus (G') and loss modulus (G") under various instrument conditions (Li & Hartgerink, 2017). Analysis of strain sweep used 0.01-200% applied strain at 1 rad/s frequency. Analysis of frequency sweep used 1% strain at 0.1-100 rad/s. Analysis of shear recovery was performed by subjecting the hydrogel to 1% strain for 20 min, then 200% for 1 min, and lastly 1% for 20 min. This process allowed for shear disruption of the hydrogel sample and timed monitoring of G' and G" recovery post shear.

Cell culture. The murine oral cancer cell line, MOC1 was provided by Dr. Ravindra Uppaluri (Dana-Farber Cancer Institute, Harvard University, Boston, MA) and maintained as previously described (Judd et al., 2012). For in vitro experiments, mouse MOC1 cells were cultured at 37° C. with 5% $CO_2$ in media routinely used for maintaining this cell line (Judd et al., 2012). For live-dead viability studies done using 2-D culture, peptide hydrogel 70 µL in volume (thickness approximately 1.75 mm) were pipetted into the wells of Lab-Tek 16 well chamber slides (Thermo Fisher, Rochester, NY). The gels were pipetted carefully into the bottom of the wells, and the plates were gently tapped down onto the bench top before shear recovery to flatten the pipetted gels and facilitate uniform spreading of the material. After pipetting, time was allowed for the samples to shear recover (5-10 min) before the addition of 200 µL cell media and 5,000 MOC1 cells. Each time point (days 1, 3, 7) had separate slides prepared with duplicate gels. Cell media was replaced every 2 days, carefully pipetting to avoid dislodging the gel material. Live-dead analysis was performed using the procedure previously described (Leach et al., 2019), using 2 µM Calcein AM (Thermo Fisher), 4 µM Ethidium homodimer (Thermo Fisher), and 5 g/mL Hoechst 33342 (BD Biosciences, San Jose, CA) in DPBS. Z-stack imaging with a Nikon A1 Confocal Microscope equipped with 40× water objective was used to image gels. Image processing was done with NIS Elements (Nikon Instruments, Melville, NY), and Imaris Cell Counting software (Bitplane, Concord, MA) was used to quantify live-dead percentages.

Subcutaneous experiments and histology. Female mice (C57BL/6J), purchased at age 8-12 weeks from The Jackson Laboratory, were used for subcutaneous experiments. Housing for all mice was specific pathogen-free conditions, with standard temperature and lighting conditions and free access to provided food and water. All animal experiments were conducted according to NIH guidelines and with approval from Rice University's Institutional Animal Care and Use Committee (IACUC). Mice were anesthetized using standard practice isoflurane (2% carried by oxygen) and maintained on a nose cone with 2% isoflurane. Subcutaneous experiments were performed by injecting mice with 100 µL MDP hydrogels in each of four localized sites in the dorsal flank subcutaneous space after hair was removed from the skin by shaving and the area was presterilized with swabs of 70% isopropyl alcohol. The mice were humanely euthanized by $CO_2$ asphyxiation while anesthetized at days 3 and 7, and the dorsal skin directly surrounding the hydrogel implant was removed. The skin and implant samples were then fixed overnight in 10% neutral buffered formalin, before being processed and paraffin embedded. Paraffin blocks were sectioned at 5 m thickness using a microtome, and staining was performed using standard Masson's trichrome kits.

MOC orthotopic murine model of oral cancer. MOC1 tumors were established by injecting 2×$10^6$ cells (70%:30% cells: Matrigel®Matrix) into the maxillary vestibule of the left oral cavity in C57BL/6J mice. Once MOC1 tumors were established (4-5 mm diameter, typically requiring 5 days of growth), 30 µl of SynerGel or controls were injected into the oral tumor site. Tumor growth was monitored by tumor size measurements (in diameter) taken at least two times per week using digital calipers to measure the longest dimension (single dimension). Data was then analyzed for Kaplan-Meier survival and tumor growth curves. All protocols were in accordance with the guidelines for humane treatment of laboratory animals by the National Institutes of Health, the Animal Welfare Committee and the Center for Laboratory Animal Medicine and Care (CLAMC) at the University of Texas Health Science Center at Houston. Excessive tumor burden, defined as tumor diameter reaching 12 mm, tumor ulceration, or a weight loss of greater than 20% were factors that were considered for all endpoints in tumor growth and survival data.

Statistical methods. Statistical analyses were performed using Prism 7.0 (GraphPad, San Diego, CA). Statistical analyses for Kaplan-Meier survival curves were performed using the Log-rank/Mantel-Cox test. Statistical significance for tumor growth curves was determined by a two-way ANOVA test followed by selected comparison using Tukey's multiple comparison tests with multiple comparison correction. All p values were two-sided and p values less than 0.05 were considered significant.

Example 7—Cyclic Dinucleotide Release Kinetics from Multidomain Peptides and Commercially Available Hydrogels Biomaterial-based drug delivery is a rapidly growing area of research, demonstrating the ability of designer materials to control the release and presentation of bioactive signals and improve therapeutic efficacy (Kearney & Mooney, 2013; Bookstaver et al., 2018; Gu & Mooney, 2016; Lopez-Silva et al., 2020). The use of biomaterials has shown particular promise in cancer immunotherapy applications (Leach et al., 2018). In a murine model of head and neck squamous cell carcinoma (HNSCC), the inventors reported on STINGel as a cationic peptide hydrogel that could control the delivery of cyclic dinucleotides (CDN), which are immunotherapy agents that act as Stimulator of Interferon Genes (STING) agonists (Leach et al., 2018). STINGel resulted in significantly enhanced intratumoral treatment efficacy with only a single injection into early oral tumors (6-fold higher survival compared to treatment with drug alone).

It is well known that many current immunotherapy strategies are hindered by the toxicity of systemically delivered immunomodulators which often require high doses and frequent re-dosing, increasing the possibility of immune-related adverse events (Wang et al., 2019; Xing et al., 2019). Injectable, drug-carrying biomaterials offer one method of overcoming these limitations, allowing for focused dose delivery, localized response, and reduced off-target effects (Leach et al., 2019). This study expands the work on the use of multidomain peptide (MDP) hydrogels for advanced immunotherapeutic applications. MDPs are a class of easily synthesized biomaterials designed to self-assemble into nanofibrous networks via supramolecular interactions, including hydrophobic packing, β-sheet hydrogen bonding, electrostatic charge repulsion, and ionic crosslinking (Dong et al., 2007; Moore et al., 2017). MDPs can incorporate a large variety of residues and still result in nanofibers and hydrogels (Lopez-Silva et al., 2019), and can be made using the general formula of $X_m(Hp)_nX_m$, where 'X' can be any charged or sterically repulsive residue (e.g. E, D, R, K, or even hydroxyproline [O]), 'H' is a hydrophobic residue (e.g. L, I, V, A), 'p' is a polar residue (e.g. S, T, N, Q), 'm' can be 1-5 residues in length, and 'n' 4-7 residues. Part of the study described herein was to compare the drug delivery properties of a number of MDP designs with a focus on charge chemistry (testing the effects of different substitutions at the X positions).

The pro-tumorigenic enzyme inducible nitric oxide synthase (iNOS) drives the induction and functional activation of immunosuppressive tumor-infiltrating myeloid-derived suppressor cells; polarizes macrophages towards the tumor-promoting M2 phenotype; and regulates $CD4^+$ T cell differentiation (Jayaraman et al., 2012; Lu et al., 2015; Jayaraman et al., 2014). The anti-tumor immunomodulatory activity of iNOS inhibition have been further described as a component of immunotherapy approaches in combination with chemoradiotherapy (Hanoteau et al., 2019) and checkpoint inhibitor-based radio-immunotherapy (Newton et al., 2019). These findings suggest that the ability to modulate iNOS activity directly at the tumor site would be beneficial for cancer immunotherapy. The synthesis and characterization of a novel drug-mimicking biomaterial termed the L-NIL-MDP is described above in Examples 1-5 (Leach et al., 2019). L-NIL, or N6-(1-iminoethyl)-L-lysine, is a potent small molecule inhibitor of iNOS (Moore et al., 1994). An L-NIL-mimicking MDP hydrogel can be readily synthesized with durable L-NIL activity, generating an iNOS-inhibiting gel that would remain in vivo for weeks after only a single injection (Leach et al., 2019; Moore et al., 1994). Furthermore, the L-NIL-MDP showed an extended ability to reduce tumor vascular endothelial growth factor (VEGF) levels, a key modulator of immune function (Jayaraman et al., 2012). These unique properties suggested the L-NIL-MDP biomaterial would be an excellent vehicle candidate for immunotherapies.

The primary goal in this study was to investigate the efficacy of the drug-mimicking L-NIL-MDP biomaterial in a challenging model of HNSCC. Successful treatment of established HNSCC tumors by immunotherapy is a significant challenge, one the inventors sought to address using biomaterials for extended and focused therapy delivery. Herein, the results from the first experiments with cyclic dinucleotide STING agonist-loaded L-NIL-MDP, termed SynerGel, are described. The ability to extend the release of CDNs compared to other common biomaterials and different MDP designs, influence the local immune response in vivo, and treat established solid tumors with only a single intratumoral injection of this dual-function biomaterial system are demonstrated.

Whether the drug-mimicking L-NIL-MDP hydrogel could effectively load and control the delivery of CDN immune agonists compared to other biomaterials was investigated. As shown in FIGS. 11A-D, a study was performed comparing various types of in-house synthesized MDP hydrogels (see Example 6 for synthesis methods) and commercially available hydrogels for their CDN release properties. CDNs possess negatively charged thiophosphates that link the molecules' nucleotides, which, it was hypothesized, could favorably interact with positively charged materials via intermolecular hydrogen bonding and electrostatic charge pairing, resulting in significantly different CDN release rates between chemically diverse materials. Different hydrogel systems were prepared at similar drug loading concentrations (0.9 mM) and material concentrations by weight according to manufacture instructions for purchased materials. The differences observed in release kinetics were thought to be primarily attributed to the presence or absence of favorable chemical interactions between CDN drug molecules and the biomaterial vehicles.

Figure 11:
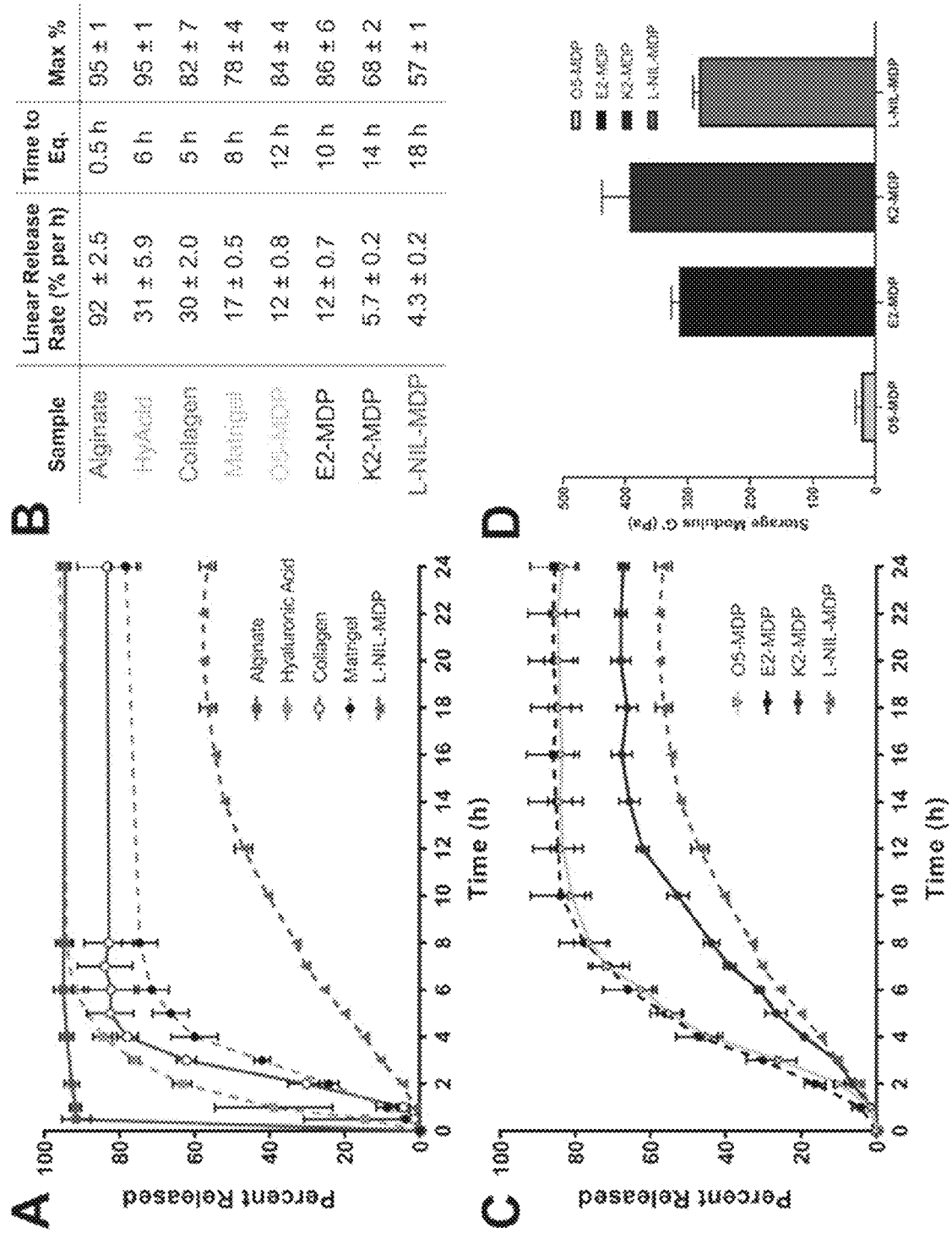
FIGS. 11A-D. CDN release kinetics from MDP and commercially available hydrogels.

The results show that the highly anionic polysaccharide alginate and hyaluronic acid hydrogels showed the fastest CDN release rates and released the greatest percentage of loaded CDN (~95%), suggesting a lack of favorable interactions and likely charge repulsion with the negative CDN payload (FIG. 11A). Collagen and Matrigel hydrogels (derived from extracellular matrix components) also showed relatively fast CDN release, and all four control hydrogels showed significantly faster release compared to SynerGel. SynerGel (based on the L-NIL-MDP) demonstrated between 4- and 20-fold slower release in the initial linear phase, taking 18 hours to reach equilibrium in this in vitro model (FIG. 11C). Furthermore, as has been observed previously for the STINGel (based on the K2-MDP), SynerGel reached a biased equilibrium in this model (only ever reaching ~60% observed CDN release), providing further evidence of favorable material-to-drug interactions that hold drug payload within the hydrogel for extended periods of time. It also is interesting to note that all tested MDPs (the anionic E2-MDP, neutral 05-MDP, and cationic STINGel K2-MDP and SynerGel L-NIL-MDP) showed slower (i.e., better, more controlled) CDN release profiles than any of the commercially available hydrogel systems (FIG. 11C), with the tested MDPs ranging from 10-18 h to reach equilibrium, and the commercial systems ranging from 0.5-8 h. It was hypothesized that this may be due to known physical material differences, such as the smaller average peptide fiber size and pore size of synthetic MDPs compared to the large fiber and pore sizes of the tested biologically derived materials (Lopez-Silva et al., 2020; Moore & Hartgerink, 2017).

In comparing only the synthetic MDPs (FIG. 11C), L-NIL-MDP-based SynerGel showed a similar yet slightly slower release profile compared to the lysine-based K2-MDP used in previous STINGel studies (Leach et al., 2018), which was expected due to its similarly cationic acetamidine side-chains. SynerGel also had an approximately 3-fold slower release rate than hydroxyproline-based 05-MDP and glutamate-based E2-MDP. Interestingly the anionic E2-MDP and charge-neutral 05-MDP showed nearly identical release profiles to each other, despite differences in side-chain chemistry and significant differences in bulk material rheological strength (FIG. 11D). Indeed, despite 05-MDP being a relatively weak and compliant hydrogel and E2-MDP showing similar strength to the other cationic MDPs, clearly bulk material strength did not influence small molecule CDN diffusion, but rather the presence (or absence) of favorable intermolecular interactions governs the observed release kinetic profiles.

Example 8—In Vitro and In Vivo Characterization of L-NIL-MDP Hydrogel

Figure 12:
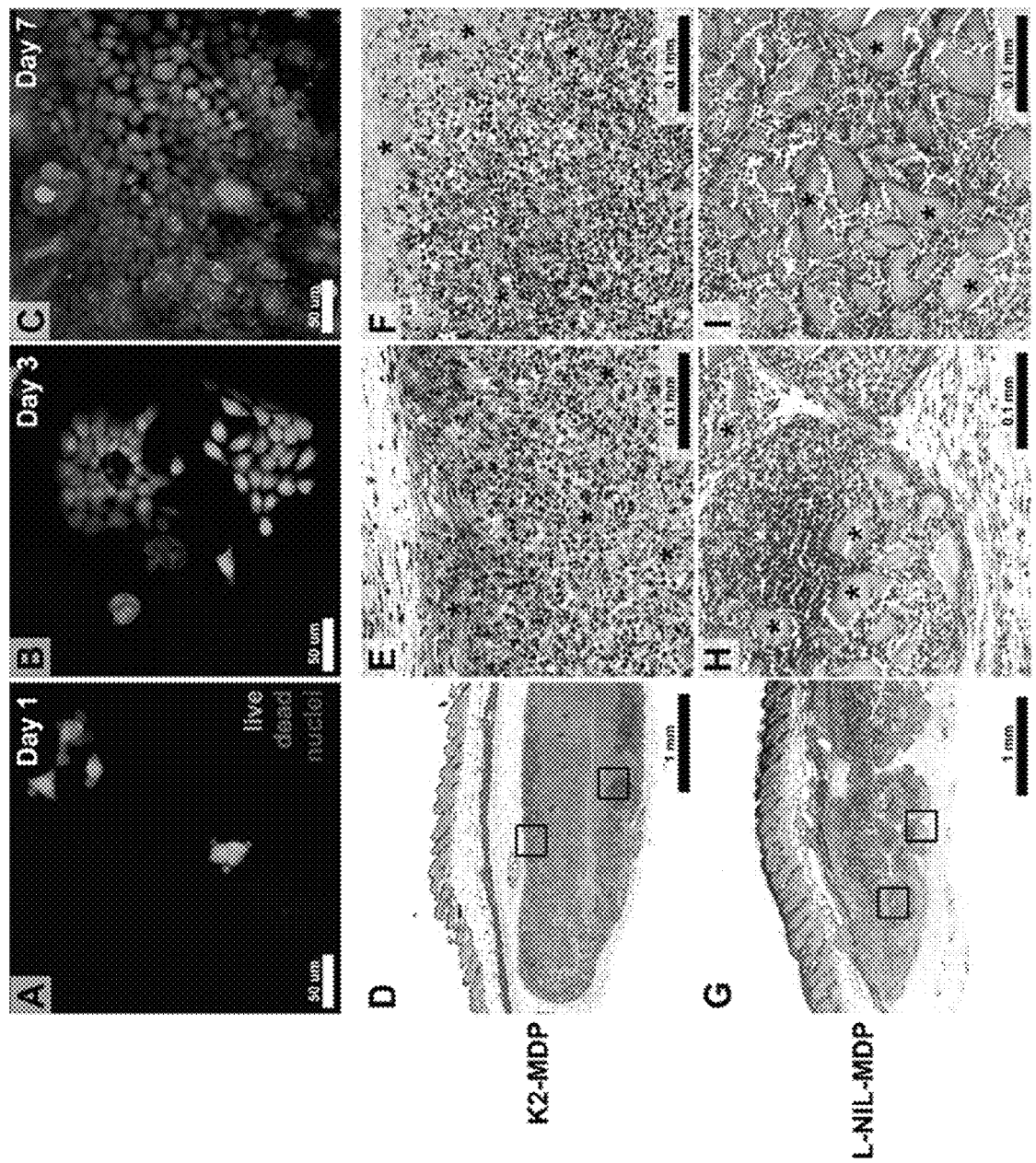
FIGS. 12A-I. In vitro and in vivo characterization of L-NIL-MDP hydrogel.

Next, how unloaded L-NIL-MDP (as the biomaterial component of SynerGel) interacted with biological systems, both in vitro and in vivo, was characterized in order to directly compare it to the K2-MDP previously used in STINGel formulations. Murine oral cancer cells (MOC1) cultured on L-NIL-MDP showed high viability according to live-dead assays and were able to proliferate on the hydrogel over 7 days (FIGS. 12A-C), growing from the low density seeding of only a few cells on the hydrogel surface (FIG. 12A) to larger clumps (FIG. 12B) and finally large communities that covered the entire hydrogel surface (FIG. 12C). This demonstrated that the L-NIL drug-mimicking scaffold was biocompatible and not directly cytotoxic to cancer cells, but facilitated cell attachment and growth which is consistent with other cationic hydrogel materials we have studied.

Subcutaneous injections of hydrogels in the dorsal flank of healthy mice allowed for a basic characterization of the host immune response to the materials, with Masson's trichome stained histology images shown in FIGS. 12D-I. As expected, the K2-MDP, which has been previously characterized (Moore et al., 2018), showed homogenous cellular infiltration of immune cells (FIGS. 12E-F) known to be primarily monocytes and macrophages (as first responders participating in an acute immune response to the biomaterial) (Lopez-Silva et al., 2020). However, it was interesting to observe that the L-NIL-MDP showed a much less homogenous cellular infiltration at early time points (day 3 post injection). Cell nuclei were instead observed to be more concentrated in pools and channels around large islets of undegraded hydrogel throughout the implant (FIGS. 2H-I), suggesting a distinct immune response to this material compared to K2-MDP. Prior studies have shown L-NIL-MDP hydrogels degrade much slower in vivo, and are observable out to 21 days post injection (Leach et al., 2019). It was hypothesized that this slower degradation profile may influence the way interacting immune cells (such as macrophages) infiltrate and remodel the material. Consequently, the material's iNOS inhibitory activity may influence the normal function of macrophages (which are high expressors of iNOS) in ways not yet understood. However, these results also confirmed the biocompatibility of unloaded SynerGel in vivo, showing that the hydrogel can interact with and be infiltrated by immune cells, which is a critical element of any immunotherapy-based approach.

Figure 13:
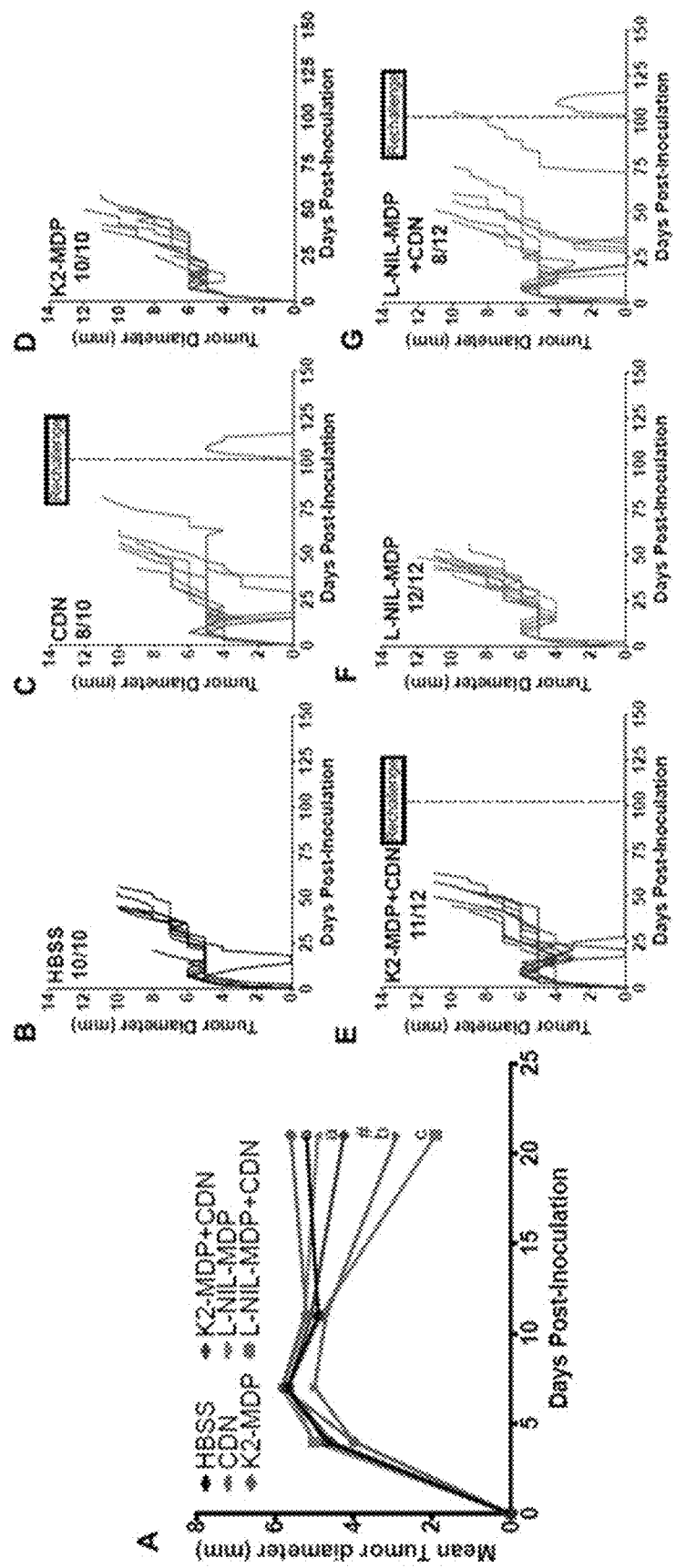
FIGS. 13A-G. Tumor growth curves in controls and SynerGel treated animals.
Figure 14:
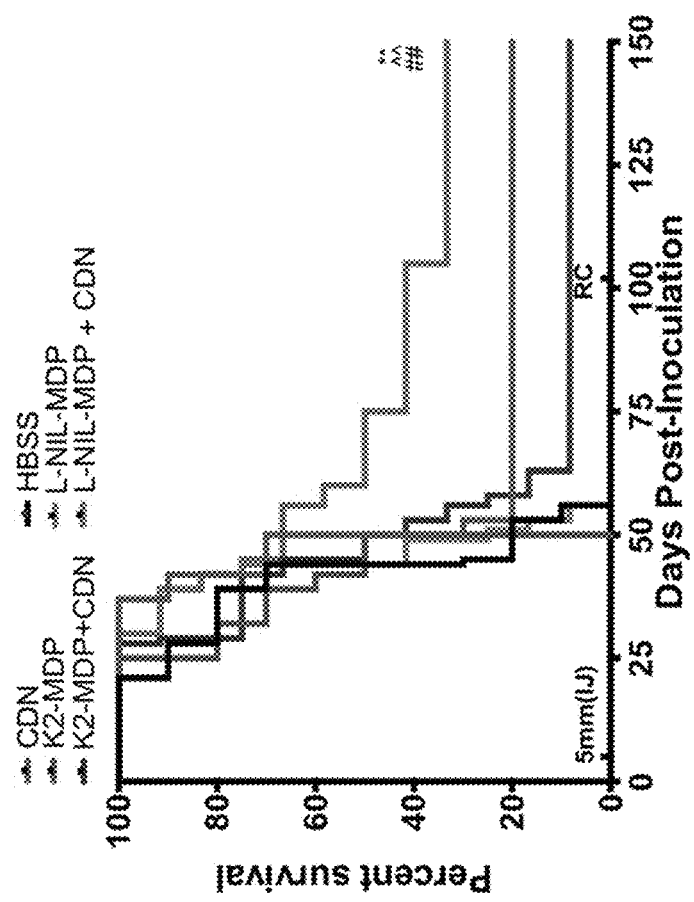
FIG. 14. Survival curves for controls and SynerGel treated mice bearing established MOC1 oral tumors. Kaplan-Meier curves of the different experimental groups is based on euthanasia timepoints due to tumor burden. Intratumoral injections were given when tumors were at 4-5 mm, represented on the x-axis as 5 mm(IJ). Survivor rechallenge (RC) was done at post-day 100 time point. L-NIL-MDP+CDN (SynerGel) treated mice had improved survival. SynerGel increased survivorship from 20% to 33% compared to CDN alone. Log-rank test; **, $p<0.01$ vs. HBSS; ^^, $p<0.01$ vs. K2-MDP; ##, $p<0.01$ vs. L-NIL-MDP.
Figure 15:
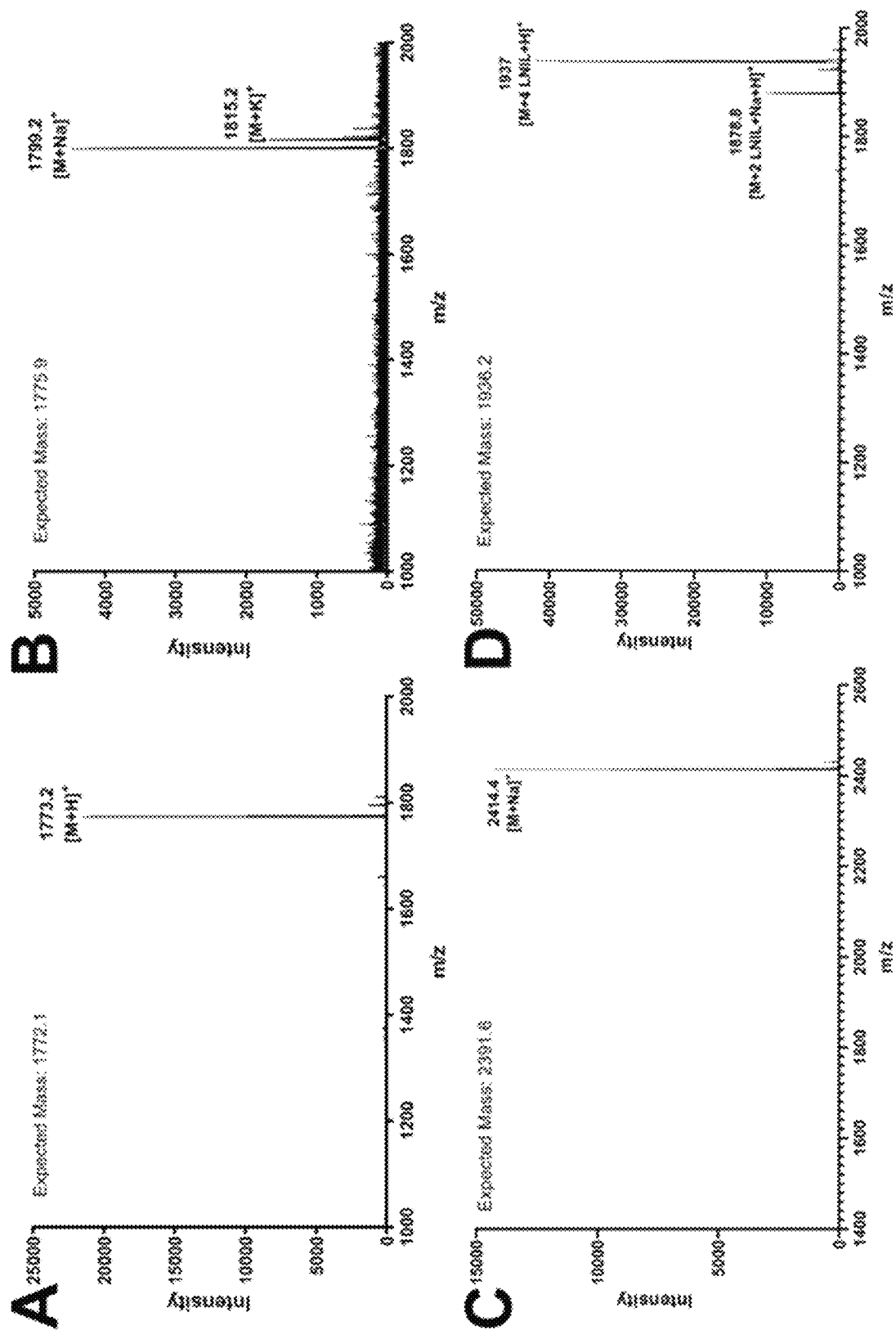
FIGS. 15A-D. MALDI-TOF mass spectroscopy spectra for synthesized MDPs.

Example 9—Efficacy of CDN-Loaded L-NIL-MDP (SynerGel) in a Murine Model of HNSCC The efficacy of STINGel (K2-MDP hydrogel loaded with CDN) in a non-palpable murine model of HPV-associated HNSCC, MOC2-E6E7, was previously reported. In this current study, the efficacy of L-NIL-MDP hydrogel loaded with CDN (SynerGel) compared to STINGel was evaluated in MOC1, a murine model of non-HPV-associated HNSCC which does not express ectopically generated viral antigens. FIGS. 13 and 14 show the results from tumor treatment efficacy studies in C57BL/6 mice bearing established (4-5 mm diameter) MOC1 tumors in the oral cavity. Growth of MOC1 tumors in mice treated with HBSS, CDN alone, K2-MDP, K2-MDP+CDN (STINGel), L-NIL-MDP or L-NIL-MDP+CDN (SynerGel) was investigated to compare SynerGel's anti-tumor efficacy with these treatment groups. Following treatments with SynerGel, decreased tumor growth was observed in MOC1 tumor-bearing mice compared to STINGel (FIG. 13A). Individual tumor growth curves over the course of study and including a secondary MOC1 rechallenge after day 100 post-tumor inoculation indicate SynerGel (L-NIL-MDP+CDN) to be a more effective biomaterial-based immunotherapy as compared to STINGel (K2-MDP+CDN) (FIGS. 13B-G).

Survival was significantly increased when the L-NIL-MDP+CDN (median survival, 67.5 days) treatment group is compared to HBSS (median survival, 44 days); L-NIL-MDP (median survival, 44 days) and K2-MDP (median survival, 46 days) (FIG. 14). Additionally, L-NIL-MDP+CDN was the only group to display statistically significant improvement in median survival over HBSS control. Treatment with L-NIL-MDP+CDN resulted in 33% of mice surviving to the 150-day endpoint compared to 20% for CDN alone and 8% for STINGel. These data suggest L-NIL-MDP+CDN (SynerGel) had better anti-tumor efficacy than the control groups and was more effective than STINGel in the treatment of MOC1-bearing mice, illustrating the potential of L-NIL-MDP as a platform for biomaterial-based immunotherapies.

Successful immunotherapeutic targeting of established HNSCC tumors remains a challenge. Elimination of established MOC1 tumors has typically required multiple injections of CDN (Moore et al., 2016). The successful treatment of early, HPV-associated MOC2-E6E7 tumors with STINGel was previously reported (Leach et al., 2018). However, in this study, more established, non-HPV associated MOC1 tumors were relatively unaffected by single intratumoral STINGel injections. Several reasons may contribute to the differences in outcome. Established oral tumors are known to create an immunosuppressive tumor immune microenvironment (TIME), driving resistance to standard immunotherapy by suppressing the immune system's ability to recognize and eliminate cancerous cells, also known as immune escape (Bonomi et al., 2014; Moy et al., 2017). Therefore, established MOC1 oral tumors are likely more challenging to treat than the non-palpable MOC2-E6E7 oral tumors. Furthermore, MOC1 tumors lack any ectopically expressed antigens, such as the E6/E7 HPV viral proteins, which may help drive a robust, specific, anti-tumor immune response (Leach et al., 2018).

Additional mechanisms of resistance may be present in the MOC1 tumor microenvironment. The immunosuppressive MOC1 TIME is likely reducing the efficacy of CDN and STINGel treatments, which are mainly designed to enhance effector immune mechanisms. However, MOC1 tumors are highly infiltrated by immunosuppressive cell types such as myeloid derived suppressor cells (MDSCs) (Judd et al., 2012). The strong presence of inhibitory immunocytes in the MOC1 tumor microenvironment (Sun et al., 2019) informed the rational design of SynerGel, replacing the K2-MDP hydrogel component in STINGel with a second generation, drug-mimicking L-NIL-MDP hydrogel. L-NIL has been shown to reverse MDSC-mediated immunosuppression through modulation of tumor-induced inflammation, as iNOS is overexpressed in nearly every solid tumor type where it supports the development of a profoundly immunosuppressive TIME (Samadi et al., 2015; Grimm et al., 2013; Sikora et al., 2010). These results support the hypothesis that biomaterial-based iNOS inhibition combined with STING activation (SynerGel) can effectively treat established tumors, successfully overcoming a tumor immune microenvironment non-responsive to traditional immunotherapy.

Figure 16:
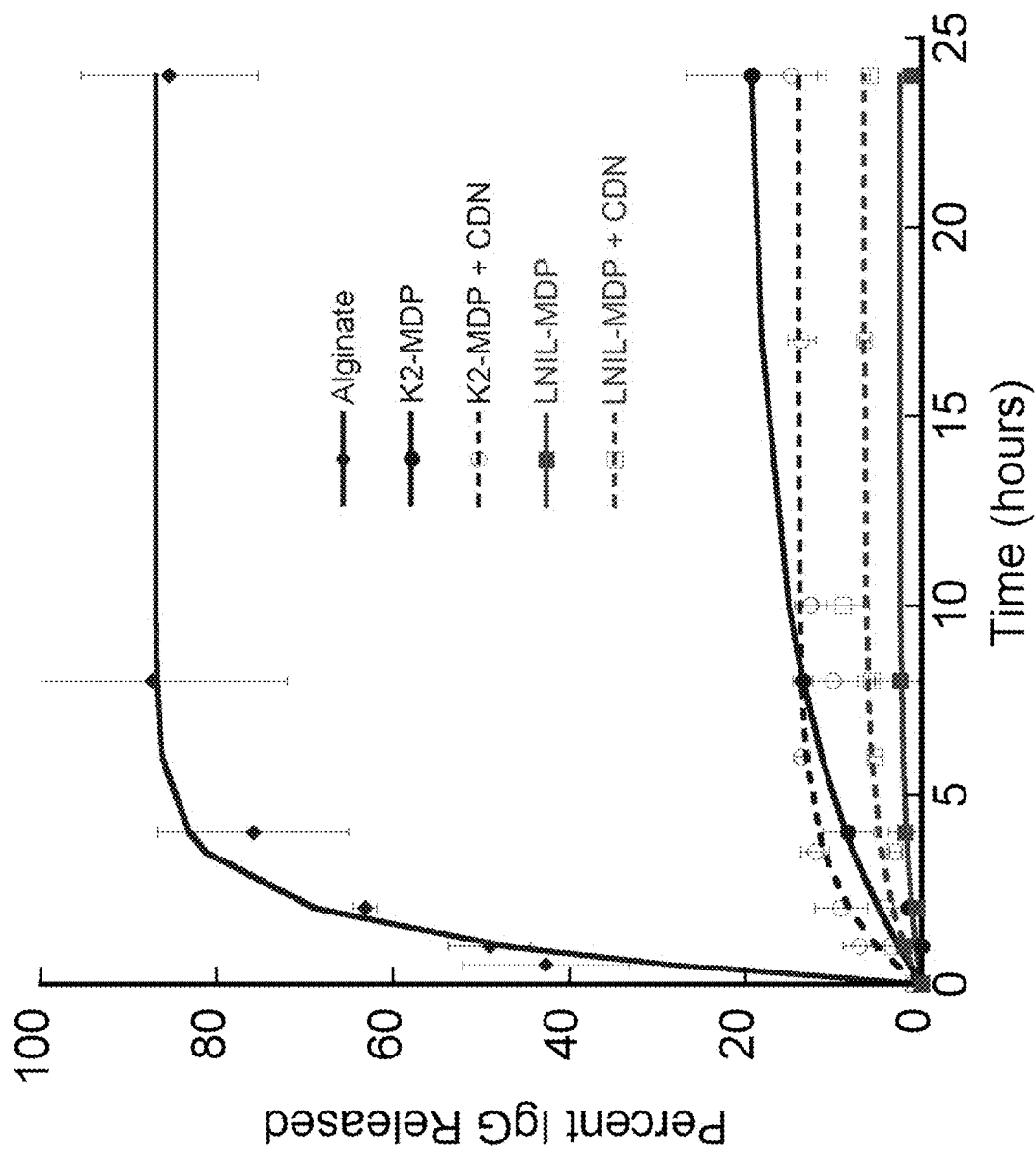
FIG. 16. IgG release kinetics from MDP and commercially available hydrogels. Drug release profiles of IgG from various hydrogels systems, comparing commercially available alginate to synthesized MDPs $K_2(SL)_6K_2$(SEQ ID NO: 2; STINGel) and L-NIL-MDP (SynerGel), loaded with either IgG only or IgG in combination with CDN.

Example 10—IgG Release Kinetics from Multidomain Peptides and Commercially Available Hydrogels Whether the drug-mimicking L-NIL-MDP hydrogel could effectively load and control the delivery of IgG compared to other biomaterials was investigated. As shown in FIG. 16, a study was performed comparing various types of in-house synthesized MDP hydrogels and commercially available hydrogels for their IgG release properties. The results show that L-NIL-MDP is able to control the release of IgG more effectively than a commercially available hydrogel control (Alginate) and also better than the previously developed K2-MDP (the peptide portion of STINGel). Furthermore, co-loading the L-NIL-MDP with CDN (cyclic dinucleotide) does not markedly alter the release kinetics of IgG (dotted lines). This indicates that the L-NIL-MDP hydrogel can be used for dual delivery of IgG biologics simultaneously with small molecule drugs, such as CDN.

Figure 17:
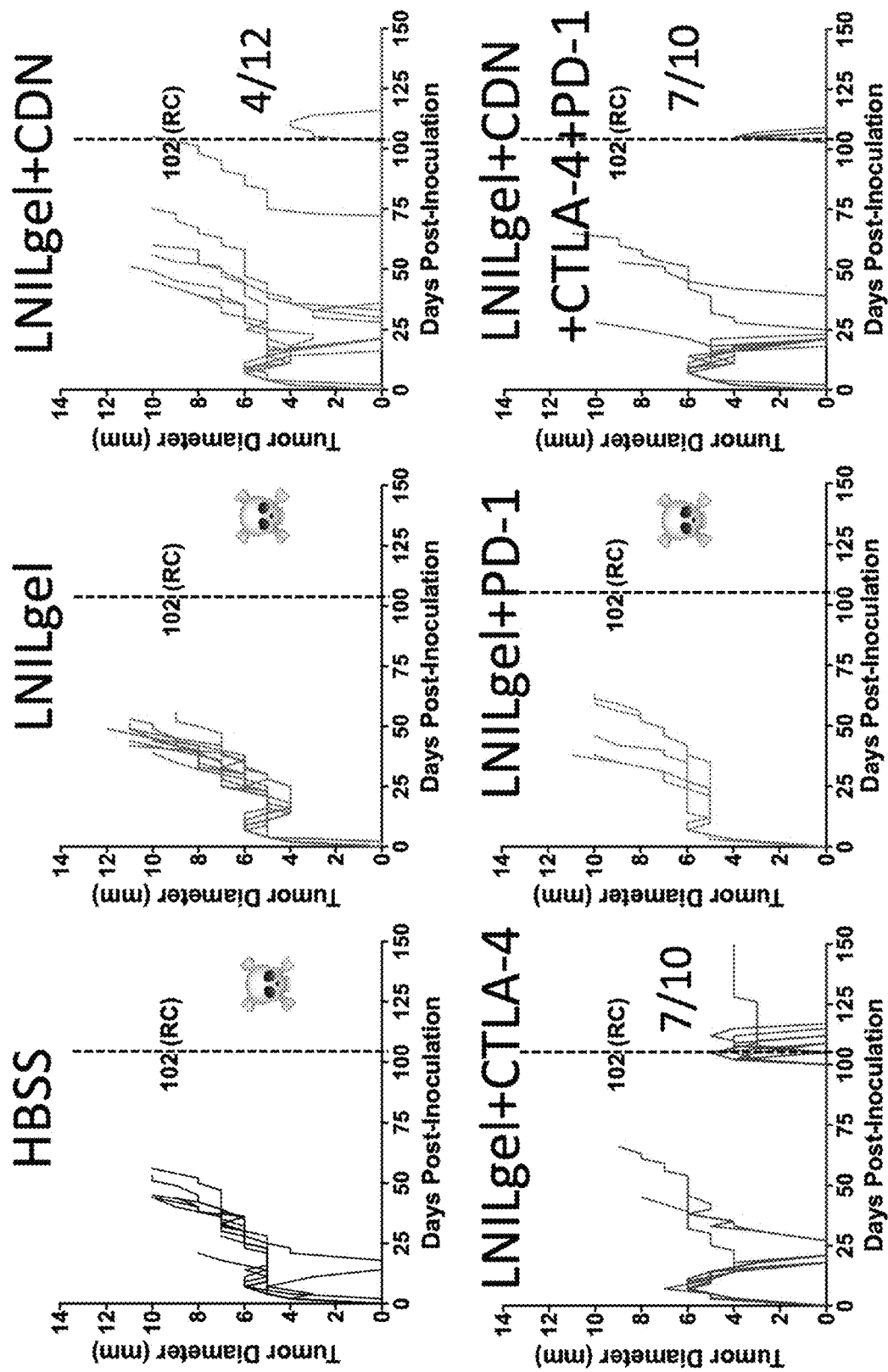
FIG. 17. Tumor growth curves in controls and animals treated with anti-CTLA-4/PD-1 and/or CDN-loaded L-NIL-MDP. Individual tumor growth curves for controls and treated mice bearing established MOC1 oral tumors over course of study. 8-9 week-old male and female C57BL/6J mice were inoculated in the left maxillary oral vestibule with MOC1 tumor cells. MOC1 tumors were allowed to grow to a well-established size of 5-6 mm in diameter (at least 100 mm$^3$). At that time point, control (buffer, HBSS) or L-NIL hydrogels loaded with or without 1) cyclic dinucleotide, 2) anti-PD-1 monoclonal antibody, and/or anti-CTLA-4 monoclonal antibody with a total volume of 30 µL were injected into the tumor. Animals surviving to day 102 were re-challenged with MOC1 tumor cells but were given no further treatment, to assess immunologic memory.
Figure 18:
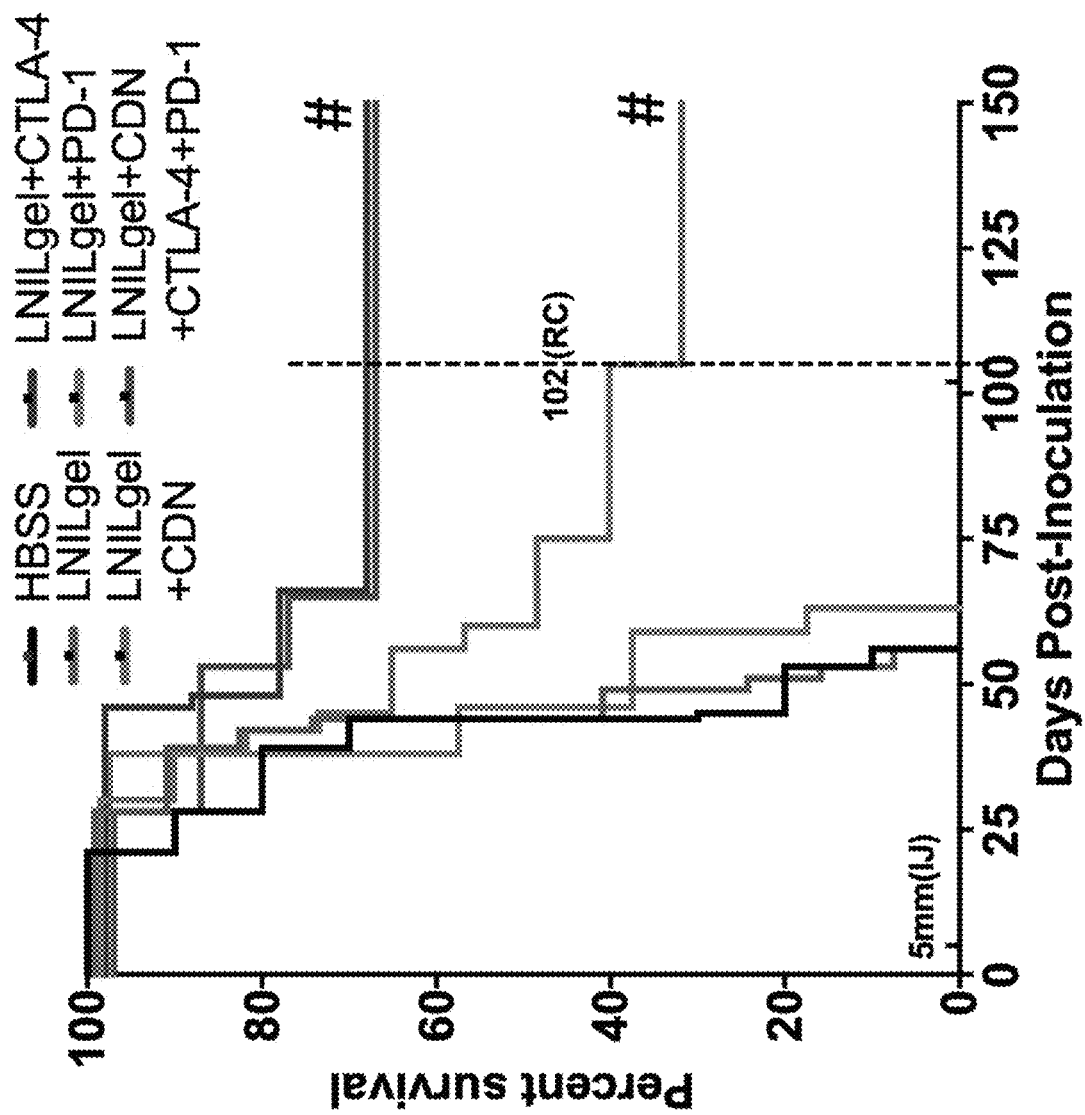
FIG. 18. Survival curves for controls and anti-CTLA-4/PD-1 and/or CDN-loaded L-NIL-MDP treated mice bearing established MOC1 oral tumors. Kaplan-Meier curves of the different experimental groups is based on euthanasia timepoints due to tumor burden. Intratumoral injections were given when tumors were at 5-6 mm, represented on the x-axis as 5 mm(IJ). Survivor rechallenge (RC) was done at post-day 102 time point.

Example 11—Efficacy of Anti-CTLA-4/PD-1 and/or CDN-Loaded L-NIL-MDP in a Murine Model of HNSCC In this study, the efficacy of L-NIL-MDP hydrogel loaded with CDN (SynerGel) compared to L-NIL-MDP loaded with anti-CTLA4 and anti-PD-1, alone or in combination with CDN, was evaluated in MOC1, a murine model of non-HPV-associated HNSCC which does not express ectopically generated viral antigens. FIGS. 17 and 18 show the results from tumor treatment efficacy studies in C57BL/6 mice bearing established (5-6 mm diameter) MOC1 tumors in the oral cavity. Growth of MOC1 tumors in mice treated with HBSS, L-NIL-MDP hydrogel alone, L-NIL-MDP+CDN (SynerGel), L-NIL-MDP+anti-CTLA-4, L-NIL-MDP+anti-PD-1 or L-NIL-MDP+CDN+anti-CTLA-4+anti-PD-1 was investigated. Following treatments with SynerGel, L-NIL-MDP+anti-CTLA-4, and L-NIL-MDP+CDN+anti-CTLA-4+anti-PD-1, decreased tumor growth was observed in MOC1 tumor-bearing mice compared to L-NIL-MDP hydrogel alone (FIG. 17). Individual tumor growth curves over the course of study and including a secondary MOC1 rechallenge after day 102 post-tumor inoculation indicate SynerGel (L-NIL-MDP+CDN), L-NIL-MDP+anti-CTLA-4, and L-NIL-MDP+CDN+anti-CTLA-4+anti-PD-1 to be effective biomaterial-based immunotherapies (FIG. 17).

Survival was significantly increased when the L-NIL-MDP+CDN treatment group is compared to HBSS (median survival, 44 days). Survival was even further increased when the L-NIL-MDP+anti-CTLA-4 and L-NIL-MDP+CDN+anti-CTLA-4+anti-PD-1 treatment groups were compared with the L-NIL-MDP+CDN treatment group (FIG. 18). Notably, the L-NIL-MDP+CDN group had 4 of 12 survivors, while the L-NIL-MDP+CTLA-4 group and the L-NIL-MDP+CDN+anti-CTLA-4+anti-PD-1 groups both had 7 of 10 survivors to 150 days. Of the 19 animals surviving to day 100, 18 showed immunological memory.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ahsan, "3-Nitrotyrosine: A biomarker of nitrogen free radical species modified proteins in systemic autoimmunogenic conditions," Human Immunology, 74:1392-1399, 2013.

Aldridge et al., "Lipopolysaccharide-stimulated RAW 264.7 macrophage inducible nitric oxide synthase and nitric oxide production is decreased by an omega-3 fatty acid lipid emulsion," J. Surg. Res., 149:296-302, 2008.

Ambs et al., "p53 and vascular endothelial growth factor regulate tumor growth of NOS2-expressing human carcinoma cells," Nature Medicine, 4:1371, 1998.

Aulisa et al., "Self-assembly of multidomain peptides: sequence variation allows control over cross-linking and viscoelasticity," Biomacromolecules, 10:2694-2698, 2009.

Berzofsky et al., "Progress on new vaccine strategies for the immunotherapy and prevention of cancer," The Journal of Clinical Investigation, 113:1515-1525, 2004.

Bonomi et al., "The Role of Inflammation in Head and Neck Cancer." In Inflammation and Cancer, Aggarwal, B. B.; Sung, B.; Gupta, S. C., Eds. Springer Basel: Basel, 2014; pp 107-127.

Bookstaver et al., "Improving Vaccine and Immunotherapy Design Using Biomaterials," Trends in Immunology, 39:135-150, 2018.

Brudno et al., "Replenishable drug depot to combat post-resection cancer recurrence," Biomaterials, 178:373-382, 2018.

Bryan & Grisham, "Methods to detect nitric oxide and its metabolites in biological samples," Free Radical Biology and Medicine, 43:645-657, 2007.

Chen & Mellman, "Oncology Meets Immunology: The Cancer-Immunity Cycle," Immunity, 39:1-10, 2013.

Collier & Segura, "Evolving the use of peptides as components of biomaterials," Biomaterials, 32:4198-4204, 2011.

Cui et al., "Self-assembly of peptide amphiphiles: From molecules to nanostructures to biomaterials," Peptide Science, 94:1-18, 2010.

Dellacherie et al., "Macroscale biomaterials strategies for local immunomodulation," Nature Reviews Materials, 4:379-397, 2019.

Deshpande et al., "Nitric oxide modulators: An emerging class of medicinal agents," Indian J. Pharm. Sci., 74:487-497, 2012.

Dong et al., "Self-Assembly of Multidomain Peptides: Balancing Molecular Frustration Controls Conformation and Nanostructure," Journal of the American Chemical Society, 129:12468-12472, 2007.

Fukumura et al., "Predominant role of endothelial nitric oxide synthase in vascular endothelial growth factor-induced angiogenesis and vascular permeability," Proceedings of the National Academy of Sciences, 98:2604-2609, 2001.

Fukumura et al., "The role of nitric oxide in tumour progression," Nature Reviews Cancer, 6:521, 2006.

Grimm et al., "Molecular Pathways: Inflammation-Associated Nitric-Oxide Production as a Cancer-Supporting Redox Mechanism and a Potential Therapeutic Target," Clin. Cancer Res., 19:5557, 2013.

Gu & Mooney, "Biomaterials and emerging anticancer therapeutics: engineering the microenvironment," Nat. Rev. Cancer, 16:56-66, 2016.

Hanahan & Weinberg, "Hallmarks of Cancer: The Next Generation," Cell, 144:646-674, 2011.

Hanoteau et al., "Tumor microenvironment modulation enhances immunologic benefit of chemoradiotherapy," Journal for ImmunoTherapy of Cancer, 7:10, 2019.

Housman et al., "Drug resistance in cancer: an overview," Cancers, 6:1769-1792, 2014.

Ischiropoulos, "Biological selectivity and functional aspects of protein tyrosine nitration," Biochemical and Biophysical Research Communications, 305:776-783, 2003.

Jayaraman et al., "Tumor-Expressed Inducible Nitric Oxide Synthase Controls Induction of Functional Myeloid-Derived Suppressor Cells through Modulation of Vascular Endothelial Growth Factor Release," The Journal of Immunology, 188:5365, 2012.

Jayaraman et al., "iNOS Expression in CD4+ T Cells Limits Treg Induction by Repressing TGFβ1: Combined iNOS Inhibition and Treg Depletion Unmask Endogenous Antitumor Immunity," Clinical Cancer Research, 20:6439-6451, 2014.

Jenkins et al., "Roles of nitric oxide in tumor growth," Proceedings of the National Academy of Sciences, 92:4392-4396, 1995.

Judd et al., "Comparative Analysis of Tumor-Infiltrating Lymphocytes in a Syngeneic Mouse Model of Oral Cancer," Otolaryng. Head Neck, 147:493-500, 2012.

Kearney & Mooney, "Macroscale delivery systems for molecular and cellular payloads," Nat. Mater., 12:1004, 2013.

Kim et al., "Enhancement of neuronal cell adhesion by covalent binding of poly-d-lysine," Journal of Neuroscience Methods, 202:38-44, 2011.

Kumar et al., "Drug-triggered and cross-linked self-assembling nanofibrous hydrogels," Journal of the American Chemical Society, 137:4823-4830, 2015.

Lam et al., "Cationic surface charge combined with either vitronectin or laminin dictates the evolution of human embryonic stem cells/microcarrier aggregates and cell growth in agitated cultures," Stem Cells Dev, 23:1688-1703, 2014.

Leach et al., "STINGel: Controlled release of a cyclic dinucleotide for enhanced cancer immunotherapy," Biomaterials, 163:67-75, 2018.

Leach et al., "Advances in immunotherapy delivery from implantable and injectable biomaterials," Acta Biomaterialia, 88:15-31, 2019.

Leach et al., "Drug-Mimicking Nanofibrous Peptide Hydrogel for Inhibition of Inducible Nitric Oxide Synthase," ACS Biomater. Sci. Eng., 5:6755-6765, 2019.

Li et al., "'Missing Tooth' Multidomain Peptide Nanofibers for Delivery of Small Molecule Drugs," Biomacromolecules, 17:2087-2095, 2016.

Li & Hartgerink, "Covalent Capture of Aligned Self-Assembling Nanofibers," Journal of the American Chemical Society, 139:8044-8050, 2017.

Lopez-Silva et al., "Self-Assembling Multidomain Peptides: Design and Characterization of Neutral Peptide-Based Materials with pH and Ionic Strength Independent Self-Assembly," ACS Biomater. Sci. Eng., 5:977-985, 2019.

Lopez-Silva et al., "Chemical functionality of multidomain peptide hydrogels governs early host immune response," Biomaterials, 231:119667, 2020.

Lu et al., "Myeloid cell-derived inducible nitric oxide synthase suppresses M1 macrophage polarization," Nat. Commun., 6:6676, 2015.

MacMicking et al., "Nitric Oxide and Macrophage Function," Annual Review of Immunology, 15:323-350, 1997.

Mannick et al., "S-Nitrosylation of mitochondrial caspases," The Journal of Cell Biology, 154:1111-1116, 2001.

Moore et al., "L-N6-(1-Iminoethyl)lysine: A Selective Inhibitor of Inducible Nitric Oxide Synthase," J. Med. Chem., 37:3886-8, 1994.

Moore et al., "Established T Cell-Inflamed Tumors Rejected after Adaptive Resistance Was Reversed by Combination STING Activation and PD-1 Pathway Blockade," Cancer Immunol Res, 4:1061-1071, 2016.

Moore et al., "Nanofibrous peptide hydrogel elicits angiogenesis and neurogenesis without drugs, proteins, or cells," Biomaterials, 161:154-163, 2018.

Moore & Hartgerink, "Self-Assembling Multidomain Peptide Nanofibers for Delivery of Bioactive Molecules and Tissue Regeneration," Accounts of Chemical Research, 50:714-722, 2017.

Moy et al., "Biological mechanisms of immune escape and implications for immunotherapy in head and neck squamous cell carcinoma," Eur. J. Cancer, 76:152-166, 2017.

Nathan & Hibbs, "Role of nitric oxide synthesis in macrophage antimicrobial activity," Current Opinion in Immunology, 3:65-70, 1991.

Newton et al., "Immune microenvironment modulation unmasks therapeutic benefit of radiotherapy and checkpoint inhibition," J. Immunother. Cancer, 7:216, 2019.

Samadi et al., "A multi-targeted approach to suppress tumor-promoting inflammation," Seminars in Cancer Biology, 35:S151-S184, 2015.

Schneider et al., The effect of hydrogel charge density on cell attachment," Biomaterials, 25:3023-3028, 2004.

Sikora et al., "Targeted inhibition of inducible nitric oxide synthase inhibits growth of human melanoma in vivo and synergizes with chemotherapy," Clinical Cancer Research, 16:1834, 2010.

Sun et al., "Inhibiting myeloid-derived suppressor cell trafficking enhances T cell immunotherapy," JCI Insight, 4:e126853, 2019.

Tang et al., "Mechanistic studies of inactivation of inducible nitric oxide synthase by amidines," Biochemistry, 54:2530-2538, 2015.

Wang & Mooney, "Biomaterial-assisted targeted modulation of immune cells in cancer treatment," Nature Materials, 17:761-772, 2018.

Wang et al., "Immune Checkpoint Inhibitor Toxicity in Head and Neck Cancer: From Identification to Management," Frontiers in Pharmacology, 10:1254, 2019.

Wickremasinghe et al., "Two-Step Self-Assembly of Liposome-Multidomain Peptide Nanofiber Hydrogel for Time-Controlled Release," Biomacromolecules, 15:3587-3595, 2014.

Xing et al., "Incidence rates of immune-related adverse events and their correlation with response in advanced solid tumours treated with NIVO or NIVO+IPI: a systematic review and meta-analysis," J. Immunother. Cancer, 7:341, 2019.

Yamaguchi et al., "Glioma tumourgenicity is decreased by iNOS knockout: experimental studies using the C6 striatal implantation glioma model," British Journal of Neurosurgery, 16:567-572, 2002.

Zhang & Xu, "Metastatic melanoma cells escape from immunosurveillance through the novel mechanism of releasing nitric oxide to induce dysfunction of immunocytes," Melanoma Research, 11:559-567, 2001.

What is claimed is:

1. A peptide comprising a first domain, a second domain, and a third domain; wherein the first and third domain are each $X_m$ and m is 1-3; wherein the first domain is positioned at the N-terminal end of the second domain; wherein the third domain is positioned at the C-terminal end of the second domain; wherein the second domain comprises (Ser-Leu)$_6$; and wherein X is an amino acid having a side chain of N6-(1-iminoethyl)-lysine (L-NIL).

2. The peptide of claim 1, wherein the peptide is N-terminally acetylated.

3. The peptide of claim 1, wherein the peptide is C-terminally amidated.

4. A hydrogel comprising a plurality of peptides according to claim 1.

5. The hydrogel of claim 4, wherein the hydrogel is biocompatible.

6. The hydrogel of claim 4, wherein the hydrogel remains intact at pH 3-11.

7. The hydrogel of claim 4, wherein the hydrogel remains intact at physiological pH.

8. The hydrogel of claim 4, further comprising a cyclic dinucleotide (CDN), an immune checkpoint inhibitor, and/or an anti-cancer drug.

9. The hydrogel of claim 4, wherein the CDN is dithio-$(R_P,R_P)$-[cyclic[A(2',5')pA(3',5')p]], 2'2'-cGAMP, 2'3'-cGAMP, 3'3'-cGAMP, c-di-AMP, 2'3'-c-di-AMP, 2'3'-c-di-AM(PS)2, c-di-GMP, c-di-UMP, or c-di-IMP.

10. The hydrogel of claim 8, wherein the immune checkpoint inhibitor is a PD-L1 antibody, a PD-1 antibody, or a CTLA4 antibody.

* * * * *

UNITED STATES PATENT AND TRADEMARK OFFICE
CERTIFICATE OF CORRECTION

PATENT NO. : 12,251,449 B2
APPLICATION NO. : 17/127512
DATED : March 18, 2025
INVENTOR(S) : Jeffrey Hartgerink et al.

Page 1 of 1

It is certified that error appears in the above-identified patent and that said Letters Patent is hereby corrected as shown below:

In the Claims

In Claim 9, Column 50, Line 51, delete "claim 4", and insert --claim 8-- therefor.

Signed and Sealed this
Second Day of September, 2025

Coke Morgan Stewart
*Acting Director of the United States Patent and Trademark Office*